United States Patent
Gibson et al.

(10) Patent No.: US 10,640,498 B2
(45) Date of Patent: May 5, 2020

(54) COMPOUNDS

(71) Applicant: MISSION THERAPEUTICS LIMITED, Cambridge (GB)

(72) Inventors: Karl Richard Gibson, Sandwich (GB); Alison Jones, Cambridge (GB); Mark Ian Kemp, Cambridge (GB); Andrew Madin, Cambridge (GB); Martin Lee Stockley, Cambridge (GB); Gavin Alistair Whitlock, Sandwich (GB); Michael D. Woodrow, Cambridge (GB)

(73) Assignee: MISSION THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 16/070,936

(22) PCT Filed: Feb. 16, 2017

(86) PCT No.: PCT/GB2017/050403
§ 371 (c)(1),
(2) Date: Jul. 18, 2018

(87) PCT Pub. No.: WO2017/141036
PCT Pub. Date: Aug. 24, 2017

(65) Prior Publication Data
US 2019/0055232 A1 Feb. 21, 2019

(30) Foreign Application Priority Data

Feb. 18, 2016 (GB) .................................. 1602854.0

(51) Int. Cl.
| | | |
|---|---|---|
| C07D 417/12 | (2006.01) |
| C07D 401/14 | (2006.01) |
| C07D 401/06 | (2006.01) |
| C07D 401/12 | (2006.01) |
| C07D 403/06 | (2006.01) |
| C07D 403/14 | (2006.01) |
| C07D 413/12 | (2006.01) |
| C07D 417/14 | (2006.01) |
| C07D 471/04 | (2006.01) |
| C07D 487/04 | (2006.01) |
| C07D 487/10 | (2006.01) |
| C07D 403/12 | (2006.01) |
| C07D 413/04 | (2006.01) |
| C07D 413/06 | (2006.01) |

(52) U.S. Cl.
CPC ......... *C07D 417/12* (2013.01); *C07D 401/06* (2013.01); *C07D 401/12* (2013.01); *C07D 401/14* (2013.01); *C07D 403/06* (2013.01); *C07D 403/12* (2013.01); *C07D 403/14* (2013.01); *C07D 413/04* (2013.01); *C07D 413/06* (2013.01); *C07D 413/12* (2013.01); *C07D 417/14* (2013.01); *C07D 471/04* (2013.01); *C07D 487/04* (2013.01); *C07D 487/10* (2013.01)

(58) Field of Classification Search
None
See application file for complete search history.

(56) References Cited

U.S. PATENT DOCUMENTS

2017/0247365 A1* 8/2017 Jones .................. C07D 487/04

FOREIGN PATENT DOCUMENTS

| WO | 0177073 A1 | 10/2001 |
|---|---|---|
| WO | 2013030218 A1 | 3/2013 |
| WO | 2016/046530 A1 | 3/2016 |
| WO | 2016156816 A1 | 10/2016 |
| WO | 2017/009650 A1 | 1/2017 |
| WO | 2017/093718 A1 | 6/2017 |
| WO | 2017/109488 A1 | 6/2017 |
| WO | 2017103614 A1 | 6/2017 |
| WO | 2017/149313 A1 | 9/2017 |
| WO | 2017/158381 A1 | 9/2017 |
| WO | 2017/158388 A1 | 9/2017 |
| WO | 2017/163078 A1 | 9/2017 |
| WO | 2018060689 A1 | 4/2018 |
| WO | 2018060691 A1 | 4/2018 |

(Continued)

OTHER PUBLICATIONS

"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
Wang et al., J. Immunol. 2007, 179, pp. 5958-5965.*
The International Search Report and Written Opinion, dated Apr. 4, 2017, in the corresponding PCT Appl. No. PCT/GB2017/050403.
Falgueyret et al., "Novel, Nonpeptidic Cyanamides as Potent and Reversible Inhibitors of Human Cathepsins K and L," J. Med. Chem. 2001, 44, 94-104.

(Continued)

*Primary Examiner* — Alicia L Otton

(57) ABSTRACT

The present invention relates to novel compounds of formula (I) and methods for the manufacture of inhibitors of deubiquitylating enzymes (DUBs). In particular, the invention relates to the inhibition of ubiquitin C-terminal hydrolase 30 or ubiquitin specific peptidase 30 (USP30). The invention further relates to the use of DUB inhibitors in the treatment of conditions involving mitochondrial dysfunction and in the treatment of cancer.

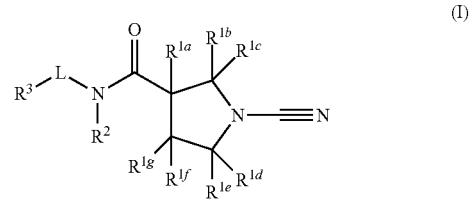

(I)

17 Claims, 1 Drawing Sheet

(56) References Cited

FOREIGN PATENT DOCUMENTS

| | | | |
|---|---|---|---|
| WO | 2018060742 | A1 | 4/2018 |
| WO | 2018065768 | A1 | 4/2018 |

OTHER PUBLICATIONS

Laine et al., "Discovery of Novel Cyanamide-Based Inhibitors of Cathepsin C," ACS Med. Chem. Lett. 2011, 2, 142-147.

Komander et al., "Breaking the chains: structure and function of the deubiguitinases," Nat Rev Mol Cell Biol. Aug. 2009;10(8):550-63.

Rydzewski et al, "Peptidic 1-Cyanopyrrolidines: Synthesis and SAR of a Series of Potent, Selective Cathepsin Inhibitors", Bioorganic & Medicinal Chemistry 10 (2002) 3277-3284.

Deaton et al, "Novel and potent cyclic cyanamide-based cathepsin K inhibitors", Bioorganic & Medicinal Chemistry Letters 15 (2005) 1815-1819.

Oballa et al, "A generally applicable method for assessing the electrophilicity and reactivity of diverse nitrile-containing compounds", Bioorganic & Medicinal Chemistry Letters 17 (2007) 998-1002.

Zapf et al, "Covalent Inhibitors of Interleukin-2 Inducible T Cell Kinase (Itk) with Nanomolar Potency in a Whole-Blood Assay", J. Med. Chem. 2012, 55, 10047-10063.

Nakamura et al, "Regulation of Mitochondrial Morphology by USP30, a Deubiquitinating Enzyme Present in the Mitochondrial Outer Membrane", Molecular Biology of the Cell, vol. 19, 1903-1911, May 2008.

Bingol et al, "The mitochondrial deubiquitinase USP30 opposes parkin-mediated mitophagy", Nature vol. 510, 370-375, 2014.

Liang et al, "USP30 deubiquitylates mitochondrial Parkin substrates and restricts apoptotic cell death", EMBO Reports, 1-10, 2015; DOI 10.15252/embr.201439820.

Ward et al., "Quantitative Chemical Proteomic Profiling of Ubiquitin Specific Proteases in Intact Cancer Cells," ACS Chem. Biol. 2016, 11, 3268-3272.

* cited by examiner

Figure 1 USP30 kinetic assay for high throughput screening of compounds using an isopeptide linked substrate
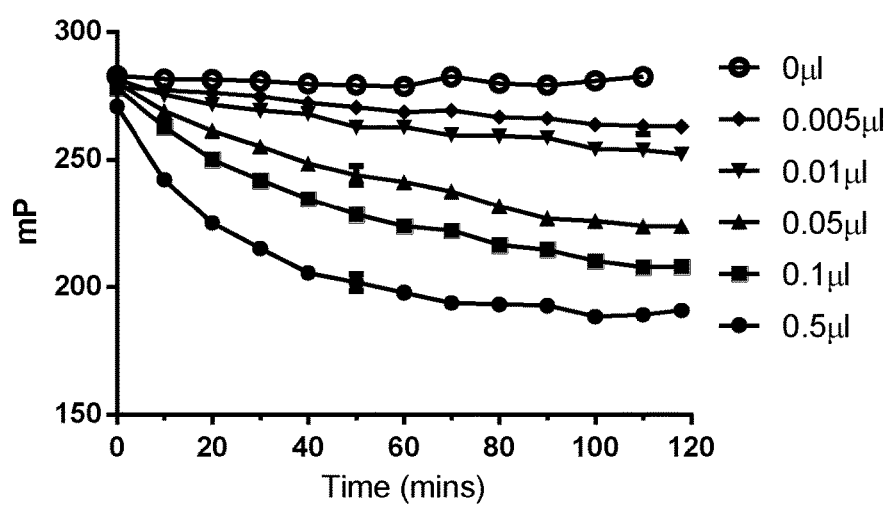

COMPOUNDS

CROSS-REFERENCE TO RELATED APPLICATIONS

This application is a National Stage Application of PCT/GB2017/050403 filed Feb. 16, 2017, which claims priority from UK Patent Application No. 1602854.0, filed on Feb. 18, 2016. The priority of said PCT and UK Patent Application are claimed. Each of the prior mentioned applications is hereby incorporated by reference herein in its entirety.

The present invention relates to novel compounds and methods for the manufacture of inhibitors of deubiquitylating enzymes (DUBs). In particular, the invention relates to the inhibition of ubiquitin C-terminal hydrolase 30 or ubiquitin specific peptidase 30 (USP30). The invention further relates to the use of DUB inhibitors in the treatment of conditions involving mitochondrial dysfunction and in the treatment of cancer.

BACKGROUND TO THE INVENTION

The listing or discussion of an apparently prior-published document in this specification should not necessarily be taken as an acknowledgement that the document is part of the state of the art or is common general knowledge.

Ubiquitin is a small protein consisting of 76 amino acids that is important for the regulation of protein function in the cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterised by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders, and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently, deubiquitylating enzymes remained elusive. USP30 is a 517 amino acid protein which is found in the mitochondrial outer membrane. It is the sole deubiquitylating enzyme bearing a mitochondrial addressing signal and has been shown to deubiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction can be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunctions in a very large number of aging processes and pathologies including but not limited to, neurodegenerative diseases (e.g. Parkinson's disease (PD), Alzheimer's disease, Huntington's disease, Amylotrophic Lateral Sclerosis (ALS), multiple sclerosis), cancer, diabetes, metabolic disorders, cardio-vascular diseases, psychiatric diseases (e.g. Schizophrenia), and osteoarthritis.

For example, Parkinson's disease affects around 10 million people worldwide (Parkinson's Disease Foundation) and is characterised by the loss of dopaminergic neurons in the substantia nigra. The exact mechanisms underlying PD are unclear; however mitochondrial dysfunction is increasingly appreciated as a key determinant of dopaminergic neuronal susceptibility in PD and is a feature of both familial and sporadic disease, as well as in toxin-induced Parkinsonism. Parkin is one of a number of proteins that have been implicated with early onset PD. While most PD cases are linked to defects in alpha-synuclein, 10% of Parkinson's cases are linked to specific genetic defects, one of which is in the ubiquitin E3 ligase parkin. Parkin and the protein kinase PTEN-induced putative kinase 1 (PINK1) collaborate to ubiquitylate mitochondrial membrane proteins of damaged mitochondria resulting in mitophagy. Dysregulation of mitophagy results in increased oxidative stress, which has been described as a characteristic of PD. Inhibition of USP30 could therefore be a potential strategy for the treatment of PD. For example, PD patients with parkin mutations leading to reduced activity could be therapeutically compensated by inhibition of USP30.

It has been reported that depletion of USP30 enhances mitophagic clearance of mitochondria and also enhances parkin-induced cell death. USP30 has also been shown to regulate BAX/BAK-dependent apoptosis independently of parkin over expression. Depletion of USP30 sensitises cancer cells to BH-3 mimetics such as ABT-737, without the need for parkin over expression. Thus, an anti-apoptotic role has been demonstrated for USP30 and USP30 is therefore a potential target for anti-cancer therapy.

The ubiquitin-proteasome system has gained interest as a target for the treatment of cancer following the approval of the proteasome inhibitor bortezomib (Velcade®) for the treatment of multiple myeloma. Extended treatment with bortezomib is limited by its associated toxicity and drug resistance. However, therapeutic strategies that target specific aspects of the ubiquitin-proteasome pathway upstream of the proteaseome, such as DUBs, are predicted to be better tolerated. Thus, there is a need for compounds and pharmaceutical compositions to inhibit DUBs such as USP30 for the treatment of indications where DUB activity is observed, including, although not limited to, conditions involving mitochondrial dysfunction and cancer.

SUMMARY OF THE INVENTION

In accordance with a first aspect of the invention there is provided a compound of formula (I)

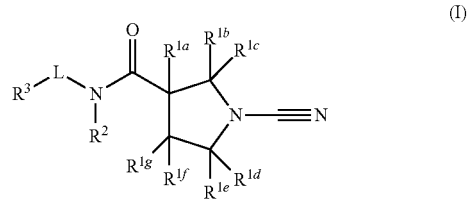

or a pharmaceutically acceptable salt thereof, wherein:
$R^{1b}$, $R^{1c}$, $R^{1d}$ and $R^{1e}$ each independently represent hydrogen or an optionally substituted $C_1$-$C_6$ alkyl, or $R^{1b}$ is linked to $R^{1c}$ or $R^{1a}$ to form an optionally substituted cycloalkyl ring, or $R^{1e}$ is linked to $R^{1d}$ or $R^{1f}$ to form an optionally substituted cycloalkyl ring;

$R^{1a}$, $R^{1f}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ is linked to $R^{1b}$ to form an optionally substituted cycloalkyl ring, or $R^{1a}$ or $R^{1g}$ is linked to $R^2$ to form an optionally further substituted ring, or $R^{1f}$ is linked to $R^{1e}$ or $R^{1g}$ to form an optionally substituted cycloalkyl ring;

$R^2$ represents optionally substituted $C_1$-$C_3$ alkyl or together with $R^3$ forms an optionally substituted 5 to 10 membered monocyclic or bicyclic ring, or $R^2$ together with $R^{1g}$ or $R^{1a}$ forms an optionally further substituted ring;

$R^3$ represents an optionally substituted 5 to 10 membered monocyclic or bicyclic heteroaryl or aryl ring or $R^3$ together with $R^2$ forms an optionally substituted 5 to 10 membered monocyclic or bicyclic ring;

L represents a covalent bond or an optionally substituted $C_1$-$C_3$ alkylene.

$R^3$ or the ring formed by $R^2$ and $R^3$ may be substituted with one or more of -$Q^1$-$(R^4)_n$, wherein each occurrence of -$Q^1$-$(R^4)_n$ is the same or different, wherein;

n is 0 or 1;

$Q^1$ represents halogen, cyano, oxo, nitro, —$OR^5$, —$SR^5$, —$NR^5R^6$, —$CONR^5R^6$, —$NR^5COR^6$, —$NR^5CONR^6R^7$, —$COR^5$, —$C(O)OR^5$, —$SO_2R^5$, —$SO_2NR^5R^6$, —$NR^5SO_2R^6$, —$NR^5SO_2NR^6R^7$, —$NR^5C(O)OR^6$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —SO—, —$SO_2$—, —CO—, —C(O)O—, —$CONR^5$—, —$NR^5$—, —$NR^5CO$—, —$NR^5CONR^6$—, —$SO_2NR^5$—, $NR^5SO_2$—, —$NR^5SO_2NR^6$—, —$NR^5C(O)O$—, —$NR^5C(O)OR^6$—, optionally substituted $C_1$-$C_6$ alkylene, optionally substituted —$C_1$-$C_6$ alkyleneoxy, or optionally substituted —$C_2$-$C_6$ alkenylene, wherein the optional substituents for the alkyl, alkoxy, alkenyl, alkylene, alkyleneoxy and alkenylene are selected from halogen, deutero, hydroxyl, thiol, cyano, amino, nitro and $SF_5$;

$R^4$ is an optionally substituted 3 to 10 membered monocyclic or bicyclic ring, wherein the optional substituents are selected from halogen, cyano, oxo, nitro, —$OR^8$, —$SR^8$, —$NR^8R^9$, —$CONR^8R^9$, $NR^8COR^9$, —$NR^8CONR^9R^{10}$, —$COR^8$, —$C(O)OR^8$, —$SO_2R^8$, —$SO_2NR^8R^9$, —$NR^8SO_2R^9$, $NR^8SO_2NR^9R^{10}$, —$NR^8C(O)OR^9$, optionally substituted —$C_1$-$C_6$ alkyl, optionally substituted —$C_1$-$C_6$ alkoxy, optionally substituted —$C_2$-$C_6$ alkenyl, optionally substituted $C_2$-$C_6$ alkynyl, optionally substituted heterocyclyl, optionally substituted cycloalkyl, optionally substituted heteroaryl, optionally substituted aryl, -$Q^2$-R, -$Q^2$-$NR^8CONR^9R^{10}$, -$Q^2$-$NR^8R^9$, -$Q^2$-$COR^8$, -$Q^2$-$NR^8COR^9$, -$Q^2$-$NR^8C(O)OR^9$, -$Q^2$-$SO_2R^8$, $Q^2$-$CONR^8R^9$, -$Q^2$-$CO_2R^8$, -$Q^2$-$SO_2NR^8R^9$, -$Q^2$-$NR^8SO_2R^9$ and -$Q^2$-$NR^8SO_2NR^9R^0$, wherein $Q^2$ represents a covalent bond, an oxygen atom, a sulphur atom, —SO—, —$SO_2$—, —CO—, or optionally substituted $C_1$-$C_6$ alkylene, optionally substituted —$C_1$-$C_6$ alkyleneoxy or optionally substituted $C_2$-$C_6$ alkenylene, and wherein $R^8$, $R^9$ and $R^{10}$ each independently represent hydrogen, optionally substituted $C_1$-$C_6$ alkyl, optionally substituted heterocyclyl, optionally substituted heteroaryl, optionally substituted aryl, or an optionally substituted cycloalkyl;

$R^5$, $R^6$ and $R^7$ each independently represent hydrogen optionally substituted $C_1$-$C_6$ alkyl or optionally substituted $C_1$-$C_6$ alkylene, wherein the optional substituents for the alkyl and alkylene are selected from halo, deutero, hydroxy, cyano, amino, nitro and $C_1$-$C_3$ alkoxy.

When n is 1, $R^4$ represents an optionally substituted 3 to 10 membered monocyclic or bicyclic heterocyclyl, heteroaryl, aryl or cycloalkyl ring. (When n is 0, $Q_1$ is present and $R^4$ is absent).

In one aspect, the invention also relates to pharmaceutical compositions comprising the compounds of the present invention and one or more pharmaceutically acceptable excipients.

In another aspect, the compounds of the invention are useful for the treatment of cancer.

BRIEF DESCRIPTION OF THE FIGURES

FIG. 1 is a graph showing proteolytic activity of USP30 measured using a fluorescence polarisation assay. Various volumes of purified USP30 as indicated were incubated with a TAMRA labelled peptide linked to ubiquitin via an iso-peptide bond.

DETAILED DESCRIPTION OF THE INVENTION

The definitions and explanations below are for the terms as used throughout this entire document including both the specification and the claims. Reference to compounds as described herein (e.g. a compound of Formula I), includes reference to Formula I and II including any sub-generic embodiments thereof.

Where any group of the compounds of formula I have been referred to as optionally substituted, this group may be substituted or unsubstituted. Substitution may be by one or more of the specified substituents which may be the same or different. It will be appreciated that the number and nature of substituents will be selected to avoid any sterically undesirable combinations.

In the context of the present specification, unless otherwise stated an alkyl, alkylene, alkoxy, alkenyl, or alkynyl substituent (or linker) group or an alkyl, alkenyl moiety in a substituent group may be linear or branched. Alkyl, alkylene, alkenyl and alkenylene chains may also include intervening heteroatoms such as oxygen.

$C_x$-$C_y$ alkyl refers to a saturated aliphatic hydrocarbon group having x-y carbon atoms which may be linear or branched. For example $C_1$-$C_6$ alkyl contains from 1 to 6 carbon atoms and includes $C_1$, $C_2$, $C_3$, $C_4$, $C_5$ and $C_6$. "Branched" means that at least one carbon branch point is present in the group. For example, tert-butyl and isopropyl are both branched groups. Examples of $C_1$-$C_6$ alkyl groups include methyl, ethyl, propyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, tert-butyl, n-pentyl, isopentyl, neopentyl and n-hexyl. $C_1$-$C_6$ alkyl, $C_1$-$C_4$ alkyl and $C_1$-$C_3$ alkyl within the definitions of $R^{1a}$, $R^{1b}$, $R^{1c}$, $R^{1d}$, $R^{1e}$, $R^{1f}$, $R^{1g}$, $R^2$, $R^5$, $R^6$, $R^7$, $R^8$, $R^9$, $R^{10}$, $Q^1$, and within the definition of substituents for $R^4$, may be unsubstituted or substituted with one or more of the substituents defined herein. Examples of substituted $C_1$-$C_6$ alkyl therefore include $CF_3$, $CH_2CF_3$, $CH_2CN$, $CH_2OH$ and $CH_2CH_2OH$.

A $C_x$-$C_y$ alkylene group or moiety may be linear or branched and refers to a divalent hydrocarbon group having one less hydrogen atom from $C_x$-$C_y$ alkyl as defined above.

$C_1$-$C_6$ alkylene may include intervening heteroatoms such as oxygen, and therefore includes alkyleneoxy groups. Alkyleneoxy as employed herein also extends to embodiments in which the or an oxygen atom (e.g. a single oxygen atom) is located within the alkylene chain, for example $CH_2CH_2OCH_2$ or $CH_2OCH_2$. Examples of $C_1$-$C_6$ alkylene groups include methylene, methyleneoxy, ethylene, ethyleneoxy, n-propylene, n-propyleneoxy, n-butylene, n-butyleneoxy, methylmethylene and dimethylmethylene. Unless stated otherwise, $C_1$-$C_6$ alkylene, $C_1$-$C_4$ alkylene and $C_1$-$C_3$ alkylene within the definitions of L, $R^5$, $R^6$, $R^7$, $Q^1$ and $Q^2$ may be unsubstituted or substituted with one or more of the substituents defined herein.

$C_2$-$C_6$ alkenyl refers to a linear or branched hydrocarbon chain radical containing at least two carbon atoms and at least one double bond and includes $C_2$-$C_4$ alkenyl. Examples of alkenyl groups include ethenyl, propenyl, 2-propenyl, 1-butenyl, 2-butenyl, 1-hexenyl, 2-methyl-1-propenyl, 1,2-butadienyl, 1,3-pentadienyl, 1,4-pentadienyl and 1-hexadienyl. Unless stated otherwise, $C_2$-$C_6$ alkenyl and $C_2$-$C_4$ alkenyl within the definitions of $Q^1$ and within the definition of substituents for $R^4$, may be unsubstituted or substituted with one or more of the substituents defined herein.

$C_2$-$C_6$ alkenylene refers to linear or branched hydrocarbon group having one less hydrogen atom from $C_2$-$C_6$ alkenyl as defined above. Examples of $C_2$-$C_6$ alkenylene include ethenylene, propenylene and butenylene. Unless stated otherwise, $C_2$-$C_6$ alkenylene and $C_2$-$C_4$ alkenylene within the definition of substituents for $Q^1$ and $Q^2$, may be unsubstituted or substituted with one or more of the substituents defined herein.

$C_2$-$C_6$ alkynyl refers to a linear or branched hydrocarbon chain radical containing at least two carbon atoms and at least one triple bond. Examples of alkenyl groups include ethynyl, propynyl, 2-propynyl, 1-butynyl, 2-butynyl and 1-hexynyl. Unless specified otherwise, $C_2$-$C_6$ alkynyl, within the definitions of $Q^1$ and within the definition of substituents for $R^4$, may be unsubstituted or substituted with one or more of the substituents defined herein.

$C_1$-$C_6$ alkoxy refers to a group or part of a group having an —O—$C_x$-$C_y$ alkyl group according to the definition of $C_x$-$C_y$ alkyl above. $C_1$-$C_6$ alkoxy contains from 1 to 6 carbon atoms and includes $C_1$, $C_2$, $C_3$, $C_4$, $C_5$ and $C_6$. Examples of $C_1$-$C_6$ alkoxy include methoxy, ethoxy, propoxy, isopropoxy, butoxy, pentoxy and hexoxy. Alkoxy as employed herein also extends to embodiments in which the or an oxygen atom (e.g. a single oxygen atom) is located within the alkyl chain, for example $CH_2CH_2OCH_3$ or $CH_2OCH_3$.

Thus the alkoxy may be linked through carbon to the remainder of the molecule, for example, —$CH_2CH_2OCH_3$, or alternatively, the alkoxy is linked through oxygen to the remainder of the molecule, for example —$OC_{1-6}$ alkyl. In certain instances, the alkoxy may be linked through oxygen to the remainder of the molecule but the alkoxy group contains a further oxygen atom, for example —$OCH_2CH_2OCH_3$. Unless specified otherwise, $C_1$-$C_6$ alkoxy and $C_1$-$C_3$ alkoxy within the definitions $R^{1a}$, $R^{1e}$, $R^{1f}$, $Q^1$, and within the definition of substituents for $R^4$, may be unsubstituted or substituted with one or more of the substituents defined herein. Examples of substituted $C_1$-$C_6$ alkoxy therefore include $OCF_3$, $OCHF_2$, $OCH_2CF_3$, $CH_2CH_2OCH_3$ and $CH_2CH_2OCH_2CH_3$.

The term "halogen" or "halo" refers to chlorine, bromine, fluorine or iodine atoms, in particular chlorine or fluorine atoms.

The term "oxo" means =O.

For the avoidance of doubt it will be understood that the cycloalkyl, heterocyclyl, aryl and heteroaryl rings disclosed herein and within the definitions of $R^{1a}$, $R^{1b}$, $R^{1c}$, $R^{1d}$, $R^{1e}$, $R^{1f}$, $R^{1g}$, $R^2$, $R^3$, $R^4$, $R^8$, $R^9$, $R^{10}$, and within the definition of substituents for $R^4$, do not include any unstable ring structures or, in the case of heteroaryl and heterocyclic ring systems, any 0-0, O—S or S—S bonds. The ring systems may be monocyclic or bicyclic. Bicyclic ring systems include bridged, fused and spiro ring systems. A substituent if present may be attached to any suitable ring atom which may be a carbon atom or, in the case of heteroaryl and heterocyclic ring systems, a heteroatom. Substitution on a ring may also include a change in the ring atom at the position of the substitution. For example, substitution on a phenyl ring may include a change in the ring atom at the position of substitution from carbon to nitrogen, resulting in a pyridine ring.

"Cycloalkyl" refers to a monocyclic saturated or partially unsaturated, non-aromatic ring, wherein all of the ring atoms are carbon, and having the number of ring atoms as indicated. For example $C_3$-$C_{10}$ cycloalkyl refers to a monocyclic or bicyclic hydrocarbon ring containing 3 to 10 carbon atoms. Examples of $C_3$-$C_{10}$ cycloalkyl are cyclopropyl, cyclobutyl, cyclopentyl, cyclohexyl, cycloheptyl, cyclooctyl and decahydronaphthalenyl. Bicyclic cycloalkyl groups include bridged ring systems such as bicycloheptane and bicyclooctane. Unless specified otherwise, cycloalkyl within the definitions of $R^{1a}R^{1b}$, $R^{1c}$, $R^{1d}$, $R^{1e}$, $R^{1f}$, $R^{1g}$, $R^2$, $R^8$, $R^9$, $R^{10}$, and within the definition of substituents for $R^4$, may be unsubstituted or substituted with one or more of the substituents defined herein.

An "aryl" group/moiety refers to any monocyclic or bicyclic hydrocarbon group comprising at least one aromatic group and having from 5 to 10 carbon atom ring members. Examples of aryl groups include phenyl and naphthyl. Bicyclic rings may be fused aromatic rings where both rings are aromatic, for example, naphthalenyl. Preferred aryl groups are phenyl and naphthyl, more preferably phenyl. Unless specified otherwise, aryl within the definitions of $R^3$, $R^4$, $R^8$, $R^9$, $R^{10}$, and within the definition of substituents for $R^4$, may be unsubstituted or substituted with one or more of the substituents defined herein.

"Heteroaryl" as used herein means a polyunsaturated, monocyclic or bicyclic 5 to 10 membered aromatic moiety containing at least one and up to 5 heteroatoms, particularly 1, 2 or 3 heteroatoms selected from N, O and S, and the remaining ring atoms are carbon atoms, in stable combinations known to the skilled person. Heteroaryl ring nitrogen and sulphur atoms are optionally oxidised, and the nitrogen atom(s) are optionally quaternized. A heteroaryl ring can be a single aromatic ring or a fused bicyclic ring where the bicyclic ring system can be aromatic, or one of the fused rings is aromatic and the other is at least partially saturated. In one example, a bicyclic heteroaryl is one in which the entire fused ring system is aromatic. A bicyclic heteroaryl can have the at least one heteroatom in either of the fused rings. For example, a bicyclic ring with an aromatic ring fused to a partially saturated ring may contain the at least one heteroatom in the aromatic ring or the partially saturated ring. Attachment of the bicyclic ring to the group it is a substituent of may be via either a heteroatom containing ring or a carbon only containing ring. The point of attachment of heteroaryl to the group it is a substituent of can be via a carbon atom or a heteroatom (e.g. nitrogen). Examples or heteroaryl rings include pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, dihydropyrrolopyridinyl, quinoxalinyl and dihydrobenzoxazinyl. Unless specified otherwise, heteroaryl within the definitions of $R^3$, $R^4$, $R^8$, $R^9$, $R^{10}$, and within the definition of substituents for $R^4$, may be unsubstituted or substituted with one or more of the substituents defined herein.

"Heterocyclyl" or "heterocyclic" as used herein in describing a ring means, unless otherwise stated, a monocyclic saturated or partially unsaturated, non-aromatic ring or a bicyclic saturated or partially unsaturated ring, wherein the bicyclic ring system is non-aromatic, the mono- or bicyclic ring having, for example, 3 to 10 members, where at least one member and up to 5 members, particularly 1, 2 or 3 members of the ring are heteroatoms selected from N, O and S, and the remaining ring atoms are carbon atoms, in stable combinations known to those of skill in the art. For example, $R^2$ and $R^3$ may together form a monocyclic or bicyclic heterocyclic ring which incorporates the amide nitrogen. Alternatively, $R^2$ may form a 5 or 6 membered heterocyclyl ring with $R^{1a}$ or $R^{1g}$. This 5 or 6 membered ring contains the amide functional group (—N(H)C(O)—) and is fused to the pyrrolidine core. Heterocyclic ring nitrogen and sulphur atoms are optionally oxidised, and the nitrogen atoms(s) are optionally quaternized. As used herein, the heterocyclic ring may be a fused ring to another ring system to form a bicycle, i.e. one or two of the heterocyclic ring carbons is common to an additional ring system. In instances where the heterocylcyl is a bicyclic ring, the second ring can be aromatic, e.g. a fused phenyl, pyridyl, pyrazolyl, or the like. The heterocyclyl may be linked through carbon or a heteroatom to the remainder of the molecule and in instances where the heterocylyl is a bicyclic ring, the link may be via the heteroatom containing ring or the fused ring. Examples of heterocyclyl groups include azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydropyrrolopyridinyl, dihydrobenzoxazinyl and tetrahydroisoquinolinyl. Unless specified otherwise, heterocyclyl within the definitions of $R^3$, $R^4$, $R^8$, $R^9$, $R^{10}$ and within the definition of substituents for $R^4$, may be unsubstituted or substituted with one or more of the substituents defined herein. Examples of substituted heterocyclyl rings include for example 4,5-dihydro-1H-maleimido,tetramethylenesulfoxide and hydantoinyl.

"Optionally substituted" as applied to any group means that the said group may if desired be substituted with one or more substituents (e.g., 1, 2, 3 or 4 substituents) which may be the same or different.

Examples of suitable substituents for "substituted" and "optionally substituted" $C_1$-$C_6$ alkyl (including $C_1$-$C_4$ alkyl, $C_1$-$C_3$ alkyl and $C_1$-$C_2$ alkyl) and $C_1$-$C_6$ alkoxy (including $C_1$-$C_4$ alkoxy, $C_1$-$C_3$ alkoxy and $C_1$-$C_2$ alkoxy) and $C_2$-$C_6$ alkenyl (including $C_2$-$C_4$ alkenyl) and $C_2$-$C_6$ alkynyl (including $C_2$-$C_4$ alkynyl), for example within the definitions of $R^{1a}$, $R^{1b}$, $R^{1c}$, $R^{1d}$, $R^{1e}$, $R^{1f}$, $R^{1g}$, $R^5$, $R^6$, $R^7$, $R^8$, $R^9$, $R^{10}$, $Q^1$, and within the definition of substituents for $R^2$, and $C_1$-$C_6$ alkylene (including $C_1$-$C_3$ alkylene) and $C_2$-$C_6$ alkenylene, for example within the definitions of L, $R^5$, $R^6$, $R^7$, $Q^1$ and $Q^2$, include halogen, deutero, hydroxyl, thiol, cyano, amino, nitro and $SF_5$ (a known mimetic of nitro), in particular, halogen (preferably fluorine or chlorine), hydroxyl and cyano. Other suitable substituents include $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl wherein any hydrocarbyl moiety may itself be substituted by halogen, e.g. fluorine, deutero, hydroxyl, cyano, amino, nitro or $SF_5$.

Examples of suitable substituents for all remaining "substituted" and "optionally substituted" moieties, including the cycloalkyl, heterocyclyl, aryl and heteroaryl rings within the definitions of $R^{1a}$, $R^{1b}$, $R^{1c}$, $R^{1d}$, $R^{1e}$, $R^{1f}$, $R^2$, $R^6$, $R^7$, $R^8$, ring A, and within the definition of substituents for $R^2$, include halogen, deutero, cyano, oxo, nitro, amino, hydroxy, $C_1$-$C_6$ alkyl or $C_1$-$C_3$ alkyl, $C_1$-$C_6$ alkoxy or $C_1$-$C_3$ alkoxy, aryl, heteroaryl, heterocyclyl, $C_3$-$C_6$ cycloalkyl, $C_{1-3}$ alkylamino, $C_{2-6}$ alkenylamino, di-$C_1$-$C_3$ alkylamino, $C_1$-$C_3$ acylamino, di-$C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl or any of the above in which a hydrocarbyl moiety is itself substituted by halogen, e.g. fluorine, deutero, hydroxyl, cyano, amino, nitro or $SF_5$ (a known mimetic of nitro).

Examples of suitable substituents for "substituted" and "optionally substituted" rings include in particular, fluorine, chlorine, oxo, cyano, $C_1$-$C_3$ alkyl, $C_1$-$C_3$ alkoxy, heterocyclyl, cycloalkyl, heteroary or aryl, wherein the alkyl or alkoxy is optionally substituted with one or more (e.g. one, two or three) substituents selected from halogen, deutero, hydroxyl, thiol, cyano, amino, nitro and $SF_5$.

Substituted groups thus include for example Br, Cl, F, CN, Me, Et, Pr, t-Bu, OMe, OEt, OPr, $C(CH_3)_3$, $CH(CH_3)_2$, $CF_3$, $OCF_3$, $C(O)NHCH_3$, cyclopropyl, phenyl, etc. In the case of aryl groups, the substitutions may be in the form of rings from adjacent carbon atoms in the aryl ring, for example cyclic acetals such as O—$CH_2$—O.

In substituted groups containing an oxygen atom such as hydroxy and alkoxy, the oxygen atom can be replaced with sulphur to make groups such as thio (SH) and thio-alkyl (S-alkyl). Optional substituents therefore include groups such as S-methyl. In thio-alkyl groups, the sulphur atom may be further oxidised to make a sulfoxide or sulfone, and thus optional substituents therefore includes groups such as S(O)-alkyl and $S(O)_2$-alkyl.

The term "treat" or "treating" or "treatment" includes prophylaxis and means to ameliorate, alleviate symptoms, eliminate the causation of the symptoms either on a temporary or permanent basis, or to prevent or slow the appearance of symptoms of the named disorder or condition. The compounds of the invention are useful in the treatment of humans and non-human animals.

The dose of the compound is that amount effective to prevent occurrence of the symptoms of the disorder or to treat some symptoms of the disorder from which the patient suffers. By "effective amount" or "therapeutically effective amount" or "effective dose" is meant that amount sufficient to elicit the desired pharmacological or therapeutic effects, thus resulting in effective prevention or treatment of the disorder. Prevention of the disorder is manifested by delaying the onset of the symptoms of the disorder to a medically significant extent. Treatment of the disorder is manifested by a decrease in the symptoms associated with the disorder or an amelioration of the reccurrence of the symptoms of the disorder.

Pharmaceutically acceptable salts of the compounds of the invention include but are not limited to addition salts (for example phosphates, nitrates, sulphates, borates, acetates, maleates, citrates, fumarates, succinates, methanesulphonates, benzoates, salicylates and hydrohalides), salts derived from organic bases (such as lithium, potassium and sodium), salts of amino acids (such as glycine, alanine, valine, leucine, isoleucine, cysteine, methionine and proline), inorganic bases (such as triethylamine, hydroxide, choline, thiamine and N—N'-diacetylethylenediamine). Other pharmaceutically acceptable salts include ammonium salts, substituted ammonium salts and aluminium salts. Further pharmaceutically acceptable salts include quaternary ammonium salts of the compounds of the invention.

General methods for the production of salts are well known to the person skilled in the art. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Where compounds of the invention exist in different enantiomeric and/or diastereoisomeric forms, the invention relates to these compounds prepared as isomeric mixtures or racemates whether present in an optically pure form or as mixtures with other isomers. Enantiomers differ only in their ability to rotate plane-polarized light by equal amounts in opposite directions and are denoted as the (+)/(S) or (−)/(R) forms respectively. Individual enantiomers or isomers may be prepared by methods known in the art, such as optical resolution of products or intermediates (for example chiral chromatographic separation e.g. chiral HPLC, or an asymmetric synthesis approach). Similarly where compounds of the invention exist as alternative tautomeric forms e.g. keto/enol, amide/imidic acid, the invention relates to the individual tautomers in isolation, and to mixtures of the tautomers in all proportions.

Included herein is the compound according to formula (II)

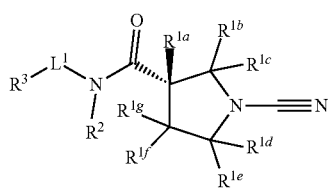

(II)

or a pharmaceutically acceptable salt thereof, wherein:
$R^{1b}$, $R^{1c}$, $R^{1d}$ and $R^{1e}$ each independently represent hydrogen or an optionally substituted $C_1$-$C_6$ alkyl, or $R^{1b}$ is linked to $R^{1c}$ or $R^{1a}$ to form an optionally substituted cycloalkyl ring, or $R^{1e}$ is linked to $R^{1d}$ or $R^{1f}$ to form an optionally substituted cycloalkyl ring;
$R^{1a}$, $R^{1f}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ is linked to $R^{1b}$ to form an optionally substituted cycloalkyl ring, or $R^{1a}$ or $R^{1g}$ is linked to $R^2$ to form an optionally further substituted ring, or
$R^{1f}$ is linked to $R^{1e}$ or $R^{1g}$ to form an optionally substituted cycloalkyl ring;
$R^2$ represents optionally substituted $C_1$-$C_3$ alkyl or together with $R^3$ forms an optionally substituted 5 to 10 membered monocyclic or bicyclic ring, or $R^2$ together with $R^{1g}$ or $R^{1a}$ forms an optionally further substituted ring;
$R^3$ represents an optionally substituted 5 to 10 membered monocyclic or bicyclic heteroaryl or aryl ring or
$R^3$ together with $R^2$ forms an optionally substituted 5 to 10 membered monocyclic or bicyclic ring;
L represents a covalent bond or an optionally substituted $C_1$-$C_3$ alkylene.

Isotopes

The compounds described herein may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. Examples of isotopes include $^2H$, $^3H$, $^{11}C$, $^{13}C$, $^{14}C$ $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$.

In an analogous manner, a reference to a particular functional group also includes within its scope isotopic variations, unless the context indicates otherwise. For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group). Deuterium may be referred to throughout as "deutero".

The isotopes may be radioactive or non-radioactive. In one embodiment, the compounds contain no radioactive isotopes. Such compounds are preferred for therapeutic use. In another embodiment, however, the compounds may contain one or more radioisotopes. Compounds containing such radioisotopes may be useful in a diagnostic context.

Certain isotopically labelled compounds of formula (I), for example, those incorporating a radioactive isotope, are useful in drug and/or substrate tissue distribution studies. The radioactive isotopes i.e. $^3H$ and $^{14}C$ are particularly useful for this purpose in view of their ease of incorporation and ready means of detection. Substitution with heavier isotopes i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^8F$, $^{15}O$ and $^{13}N$, can be useful in Positron Emission Topography (PET) studies for examining receptor occupancy. Isotopically labelled compounds of formula (I) can generally be prepared by conventional techniques known to those skilled in the art or by processes analogous to those described in the accompanying examples and preparations using an appropriate isotopically labelled reagent in place of the non-labelled reagent previously employed.

Crystalline and Amorphous Forms

The compounds of formula (I) may exist in crystalline or amorphous form and some of the crystalline forms may exist as polymorphs, which are included within the scope of the present invention. Polymorphic forms of compounds of formula (I) may be characterised and differentiated using a number of conventional analytical techniques, including, but not limited to, infra-red spectra, Raman spectra, X-ray powder diffraction, differential scanning calorimetry, thermogravimetric analysis and solid state nuclear magnetic resonance.

Accordingly, in further embodiments, the invention provides a compound according to any described embodiments in a crystalline form. The compound may be from 50% to 100% crystalline, and more particularly is at least 50% crystalline, or at least 60% crystalline, or at least 70% crystalline, or at least 80% crystalline, or at least 90% crystalline, or at least 95% crystalline, or at least 98% crystalline, or at least 99% crystalline, or at least 99.5% crystalline, or at least 99.9% crystalline, for example 100% crystalline. The compound may alternatively be in an amorphous form.

The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

The invention relates to any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

The invention relates to pharmaceutically functional derivatives of compounds as defined herein including ester derivatives and/or derivatives that have, or provide for, the same biological function and/or activity as any relevant compound of the invention. Thus, for the purposes of this invention, the term also includes prodrugs of compounds as defined herein.

The term "prodrug" of a relevant compound includes any compound that, following oral or parenteral administration, is metabolised in vivo to form that compound in an experimentally-detectable amount, and within a predetermined time (e.g. within a dosing interval of between 6 and 24 hours (i.e. once to four times daily).

Prodrugs of compounds may be prepared by modifying functional groups present on the compound in such a way that the modifications are cleaved, in vivo when such prodrug is administered to a mammalian subject. The modifications typically are achieved by synthesizing the parent compound with a prodrug substituent. Prodrugs include compounds wherein a hydroxyl, amino, sulfhydryl, carboxyl or carbonyl group in a compound is bonded to any group that may be cleaved in vivo to regenerate the free hydroxyl, amino, sulfhydryl, carboxyl or carbonyl group, respectively.

Examples of prodrugs include, but are not limited to, esters and carbamates of hydroxyl functional groups, ester groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may be metabolised in vivo. Metabolites of compounds of formula (I) are also within the scope of the present invention. The term 'metabolites' refers to all molecules derived from any of the compounds according to the present invention in a cell or organism, preferably mammal. Preferably the term relates to molecules which differ from any molecule which is present in any such cell or organism under physiological conditions.

A treatment defined herein may be applied as a sole therapy of may involve, in addition to the compounds of the invention, conventional surgery or radiotherapy or chemotherapy. Furthermore, compounds of formula (I) can also be used in combination with existing therapeutic agents for the treatment of conditions associated with cancer, including small molecule therapeutics or antibody based therapeutics.

In accordance with a first aspect of the invention there is provided a compound of formula (I)

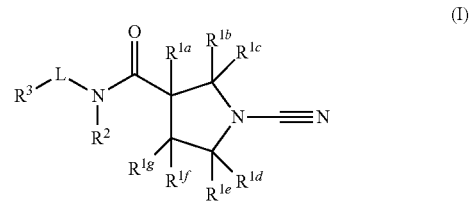

or a pharmaceutically acceptable salt thereof, wherein:
$R^{1b}$, $R^{1c}$, $R^{1d}$ and $R^{1e}$ each independently represent hydrogen or an optionally substituted $C_1$-$C_6$ alkyl, or $R^{1b}$ is linked to $R^{1c}$ or $R^{1a}$ to form an optionally substituted $C_3$-$C_6$ cycloalkyl ring, or $R^{1e}$ is linked to Rd or $R^{1f}$ to form an optionally substituted $C_3$-$C_6$ cycloalkyl ring;
$R^{1a}$, $R^{1f}$ and $R^{1g}$ each independently represent hydrogen, fluorine, cyano, hydroxyl, amino, optionally substituted $C_1$-$C_6$ alkyl or optionally substituted $C_1$-$C_6$ alkoxy, or $R^{1a}$ is linked to $R^{1b}$ to form an optionally substituted $C_3$-$C_6$ cycloalkyl ring, or $R^{1a}$ is linked to $R^2$ to form an optionally further substituted 5 or 6 membered ring, or $R^{1f}$ is linked to $R^{1e}$ or $R^{1g}$ to form an optionally substituted $C_3$-$C_6$ cycloalkyl ring, or
$R^{1g}$ is linked to $R^2$ to form an optionally further substituted 5 or 6 membered ring;
$R^2$ represents an optionally substituted $C_1$-$C_3$ alkyl or together with $R^3$ forms an optionally substituted 5 to 10 membered monocyclic or bicyclic ring, or $R^2$ together with $R^{1g}$ or $R^{1a}$ forms an optionally further substituted 5 or 6 membered ring;
$R^3$ represents an optionally substituted 5 to 10 membered monocyclic or bicyclic heteroaryl or aryl ring or together with $R^2$ forms an optionally substituted 5 to 10 membered monocyclic or bicyclic ring;
L represents a covalent bond or an optionally substituted $C_1$-$C_3$ alkylene.
In all cases described herein, $R^{1b}$, $R^{1c}$, $R^{1d}$, $R^{1e}$ may each independently represent hydrogen or optionally substituted $C_1$-$C_6$ alkyl. In particular, $R^{1b}$, $R^{1c}$, $R^{1d}$, $R^{1e}$ may each independently represent hydrogen or $C_1$-$C_3$ alkyl (e.g. methyl or ethyl). $R^{1b}$ may be hydrogen or $C_1$-$C_3$ alkyl and $R^{1c}$ may be hydrogen. $R^{1d}$ may be hydrogen or $C_1$-$C_3$ alkyl and $R^{1e}$ may be hydrogen. The alkyl may be unsubstituted or substituted with one or more substituents selected from halogen, deutero, hydroxyl, thiol, cyano, amino, nitro and $SF_5$. In particular $R^{1b}$, $R^{1c}$, $R^{1d}$, $R^{1e}$ each represent hydrogen.

$R^{1b}$ may represent hydrogen. $R^b$ may represent $C_1$-$C_6$ alkyl. $R^{1b}$ may represent $C_1$-$C_3$ alkyl, for example, methyl or ethyl. When $R^{1b}$ represents $C_1$-$C_6$ alkyl, $R^{1a}$, $R^{1c}$ c, $R^{1d}$, $R^{1e}$, $R^{1f}$ and $R^{1g}$ may each represent hydrogen. The alkyl may be unsubstituted or substituted with one or more substituents selected from halogen, deutero, hydroxyl, thiol, cyano, amino, nitro and $SF_5$, in particular fluorine. $R^{1b}$ may be hydrogen or MeOH.

$R^{1c}$ may represent hydrogen. $R^{1c}$ may represent $C_1$-$C_6$ alkyl. $R^{1c}$ may represent $C_1$-$C_3$ alkyl, for example, methyl or ethyl. When $R^{1c}$ represents $C_1$-$C_6$ alkyl, $R^{1a}$, $R^{1b}$, $R^{1d}$, $R^{1e}$, $R^{1f}$ and $R^{1g}$ may each represent hydrogen. The alkyl may be unsubstituted or substituted with one or more substituents selected from halogen, deutero, hydroxyl, thiol, cyano, amino, nitro and $SF_5$, in particular fluorine. $R^{1c}$ may be hydrogen or MeOH.

$R^{1d}$ may represent hydrogen. Rd may represent $C_1$-$C_6$ alkyl. Rd may represent $C_1$-$C_3$ alkyl, for example, methyl or ethyl. When $R^{1d}$ represents $C_1$-$C_6$ alkyl, $R^{1a}$, $R^{1b}$, $R^{1c}$, $R^{1e}$, $R^{1f}$ and $R^{1g}$ may each represent hydrogen. The alkyl may be unsubstituted or substituted with one or more substituents selected from halogen, deutero, hydroxyl, thiol, cyano, amino, nitro and $SF_5$, in particular fluorine.

$R^{1e}$ may represent hydrogen. $R^{1e}$ may represent $C_1$-$C_6$ alkyl. $R^{1e}$ may represent $C_1$-$C_3$ alkyl, for example, methyl or ethyl. When $R^{1e}$ represents $C_1$-$C_6$ alkyl, $R^{1a}$, $R^{1b}$, $R^{1c}$, $R^{1d}$, $R^{1f}$ and $R^{1g}$ may each represent hydrogen. The alkyl may be unsubstituted or substituted with one or more substituents selected from halogen, deutero, hydroxyl, thiol, cyano, amino, nitro and $SF_5$, in particular fluorine.

Alternatively, $R^{1b}$ and $R^{1c}$ may together form a cycloalkyl ring. In addition, or alternatively, $R^{1d}$ and $R^{1e}$ may together form a cycloalkyl ring. The cycloalkyl ring can contain 3, 4, 5 or 6 atoms, in particular 3 or 4 atoms. When $R^{1b}$ and $R^{1c}$ together form a $C_3$-$C_6$ cycloalkyl ring, $R^{1a}$, $R^{1d}$, $R^{1e}$, $R^{1f}$ and $R^{1g}$ may be hydrogen. When $R^{1d}$ and $R^{1e}$ together form a $C_3$-$C_6$ cycloalkyl ring, $R^{1a}$, $R^{1b}$, $R^{1c}$, $R^{1f}$ and $R^{1g}$ may each be hydrogen.

$R^{1f}$ may represent hydrogen fluorine, cyano, hydroxyl, amino, optionally substituted $C_1$-$C_6$ alkyl, or optionally substituted $C_1$-$C_6$ alkoxy. The alkyl and alkoxy may be substituted with one or more substituents selected from halogen, deutero, hydroxyl, thiol, cyano, amino, nitro and $SF_5$. $R^{1f}$ can represent hydrogen fluorine, unsubstituted or substituted $C_1$-$C_3$ alkyl or unsubstituted or substituted $C_1$-$C_3$ alkoxy. $R^{1f}$ can represent hydrogen or methyl. $R^{1f}$ can represent fluorine. $R^{1f}$ can represent methyl. $R^{1f}$ can represent methoxy. $R^{1f}$ can represent $CF_3$. $R^{1f}$ can represent $OCF_3$. When $R^{1f}$ represents fluorine, cyano, hydroxyl, amino, optionally substituted $C_1$-$C_6$ alkyl or optionally substituted $C_1$-$C_6$ alkoxy, $R^{1a}$, $R^{1b}$, $R^{1c}$, $R^{1d}$, $R^{1e}$ and $R^{1f}$ may each represent hydrogen. Alternatively, $R^{1f}$ represents hydrogen.

$R^{1g}$ may represent hydrogen, fluorine, cyano, hydroxyl, amino, optionally substituted $C_1$-$C_6$ alkyl or optionally substituted $C_1$-$C_6$ alkoxy. The alkyl and alkoxy may be substituted with one or more substituents selected from halogen, deutero, hydroxyl, thiol, cyano, amino, nitro and $SF_5$. $R^{1g}$ can represent hydrogen, fluorine, $C_1$-$C_3$ alkyl or substituted $C_1$-$C_3$ alkoxy. $R^{1f}$ can represent hydrogen or methyl. $R^{1g}$ can represent fluorine. $R^{1g}$ can represent methyl. $R^{1g}$ can represent methoxy. $R^{1g}$ can represent $CF_3$. $R^{1g}$ can represent $OCF_3$. When $R^{1g}$ represents fluorine, cyano, hydroxyl, amino, optionally substituted $C_1$-$C_6$ alkyl or optionally substituted $C_1$-$C_6$ alkoxy, $R^{1a}$, $R^{1b}$, $R^{1c}$, $R^{1d}$, $R^{1e}$ and $R^{1f}$ may each represent hydrogen. Alternatively, $R^{1g}$ represents hydrogen.

Alternatively, $R^{1f}$ and $R^{1g}$ may together form a cycloalkyl ring. Alternatively, $R^{1f}$ and $R^{1e}$ may together form a cycloalkyl ring. The cycloalkyl ring can contain 3, 4, 5 or 6 atoms, in particular 3 or 4 atoms. When $R^{1f}$ and $R^{1g}$ together form a $C_3$-$C_6$ cycloalkyl ring, $R^{1a}$, $R^{1b}$, $R^{1c}$, $R^{1d}$ and $R^{1e}$ may be hydrogen. When $R^{1f}$ and $R^{1e}$ together form a $C_3$-$C_6$ cycloalkyl ring, $R^{1a}$, $R^{1b}$, $R^{1c}$, $R^{1d}$ and $R^{1g}$ may each be hydrogen.

The cycloalkyl rings within the definitions of $R^{1a}$, $R^{1b}$, $R^{1c}$, $R^{1d}$, $R^{1e}$ and $R^{1f}$ may be unsubstituted or substituted with one or more substituents selected from halogen, deutero, cyano, oxo, nitro, amino, hydroxy, $C_1$-$C_3$ alkyl, $C_1$-$C_3$ alkoxy, $C_{1-3}$ alkylamino, $C_{2-6}$ alkenylamino, $C_1$-$C_3$ acylamino, carboxy, $C_1$-$C_3$ alkoxycarbonyl, carboxamidyl, carbamoyl, mono-$C_{1-3}$ carbamoyl and di-$C_{1-3}$ carbamoyl wherein any hydrocarbyl moiety may itself be substituted by one or more halogen, in particular fluorine. In particular, the cycloalkyl ring may be unsubstituted or substituted with one or two substituents selected from halogen, deutero, cyano, oxo, nitro, amino, hydroxy, $C_1$-$C_3$ alkyl and $C_1$-$C_3$ alkoxy, wherein the alkyl and alkoxy may be substituted with one or more halogen, in particular fluorine.

The compounds may be in the form where $R^{1a}$, $R^{1b}$, $R^{1c}$, $R^{1d}$, $R^{1e}$ and $R^{1f}$ are each hydrogen. In such cases the compounds may be of formula:

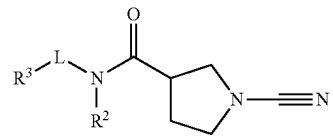

(IA)

or a pharmaceutically acceptable salt thereof, wherein $R^2$ represents an optionally substituted $C_1$-$C_3$ alkyl or together with $R^3$ forms an optionally substituted 5 to 10 membered monocyclic or bicyclic heteroaryl or heterocyclyl ring; $R^3$ represents an optionally substituted 5 to 10 membered monocyclic or bicyclic heteroaryl or aryl ring or together with $R^2$ forms an optionally substituted 5 to 10 membered monocyclic or bicyclic ring; and L represents a covalent bond or an optionally substituted $C_1$-$C_3$ alkylene.

Alternatively, the compounds may be in the form where $R^{1b}$, $R^{1c}$, $R^{1d}$, $R^{1e}$ and $R^{1f}$ are each hydrogen and $R^{1a}$ together with $R^2$ forms a 5 membered heterocyclyl ring. In such cases the compound may be of the formula:

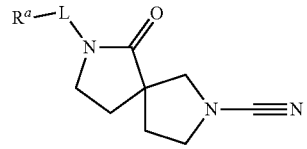

(IB)

or a pharmaceutically acceptable salt thereof wherein $R^3$ represents an optionally substituted 5 to 10 membered monocylic or bicylic heteroaryl or aryl ring and L represents a covalent bond or an optionally substituted $C_1$-$C_3$ alkylene.

In all cases described herein $R^2$ may represent an optionally substituted $C_1$-$C_3$ alkyl or together with $R^3$ forms an optionally substituted 5 to 10 membered monocyclic or bicyclic ring, or $R^2$ together with $R^{1g}$ or $R^{1a}$ forms an optionally further substituted 5 or 6 membered ring. When $R^2$ does not form part of a ring (with either $R^3$, $R^{1g}$ or $R^{1a}$), $R^2$ represents $C_1$-$C_3$ alkyl. $R^2$ may represent methyl. $R^2$ may represent ethyl. $R^2$ may represent propyl, in particular isopropyl. The alkyl may be unsubstituted or substituted with one or more substituents selected from halogen, deutero, hydroxyl, thiol, cyano, amino, nitro and $SF_5$, in particular fluorine. When $R^2$ forms a ring with $R^{1g}$ or $R^{1a}$, the ring is a 5 or 6 membered ring, preferably a 5 membered ring. When $R^2$ forms a 5 or 6 membered ring with $R^{1a}$, the ring forms a spirocycle with the pyrrolidine core. When $R^2$ forms a 5 or 6 membered ring with $R^{1g}$, the ring forms a fused bicycle with the pyrrolidine core. The 5 or 6 membered ring may be unsubstituted or substituted with one or more substituents in addition to the amide carbonyl group. The substituents may be selected from halogen, deutero, cyano, oxo, nitro, amino, hydroxy, $C_1$-$C_3$ alkyl, $C_1$-$C_3$ alkoxy, $C_{1-3}$ alkylamino, $C_{2-6}$ alkenylamino, $C_1$-$C_3$ acylamino, carboxy, $C_1$-$C_3$ alkoxycarbonyl, carboxamidyl, carbamoyl, mono-$C_{1-3}$ carbamoyl, di-$C_{1-3}$ carbamoyl wherein any hydrocarbyl moiety may itself be substituted by halogen, e.g. fluorine, deutero, hydroxyl, cyano, amino, nitro or $SF_5$. In particular, the 5 or 6 membered ring is optionally further substituted with halogen, deutero, cyano, oxo, nitro, amino or $SF_5$.

L represents a covalent bond or an optionally substituted $C_1$-$C_3$ alkylene linker or forms part of the heterocyclyl or heteroaryl ring formed by $R^2$ and $R^3$. When $R^3$ is a 5 to 10 membered monocyclic or bicyclic ring, L is preferably a covalent bond or methylene. The alkylene may be optionally substituted with halogen, duetero, hydroxyl, thiol, cyano, amino, nitro and $SF_5$, preferably fluorine. When $R^2$ together with $R^3$ forms a monocyclic or bicyclic ring, L represents a covalent bond.

The heteroaryl or aryl ring of $R^3$ may be defined according to the definition of heteroaryl and aryl ring found herein and is monocyclic or bicyclic. Where the ring is bicyclic, the second ring may be aromatic, or may be partly saturated, and thus not every atom in the 5 to 10 membered ring need be in an aryl system. Preferably, when $R^3$ is a bicyclic ring, the ring is aromatic or partially aromatic.

$R^3$ represents a 5 to 10 membered (e.g. 5, 6, 7, 8, 9 or 10 membered) monocyclic or fused bicyclic heteroaryl or aryl ring which may be optionally substituted with one or more (e.g. one, two, three or four) of -$Q^1$-$(R^4)_n$, in particular one or two of -$Q^1$-$(R^4)_n$.

In particular, $R^3$ may represent a 5 or 6 membered heteroaryl or aryl ring which may be optionally substituted with one or more (e.g. one, two, three or four) of -$Q^1$$(R^4)_n$.

Alternatively, $R^3$ may represent a 9 or 10 membered bicyclic heteroaryl or aryl ring which may be optionally substituted with one or more (e.g. one, two, three or four) of -$Q^1$-$(R^4)_n$.

When $R^3$ is a heteroaryl ring, the ring is monocyclic or bicyclic and may comprise one or more (e.g. 1, 2 or 3) heteroatoms independently selected from nitrogen, oxygen and sulphur. In particular, the heteroaryl ring may contain at least one nitrogen atom, for example, 1, 2 or 3 nitrogen atoms, preferably 1 or 2 nitrogen heteroatoms. Examples of nitrogen containing heteroaryl rings include pyridinyl, pyrazinyl, pyrimidinyl, pyridazinyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydropyrrolopyridinyl and dihydrobenzoxazinyl.

The optionally substituted 5 to 10 membered monocyclic or bicyclic heteroaryl or aryl ring may be selected from pyridinyl, pyrazinyl, pyrimidinyl, pyridazinyl, furyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, triazinyl, dihydrophyridinyl, quinoxalinyl, dihydropyrrolopyridinyl, dihydrobenzoxazinyl, phenyl, naphthyl and naphthalenyl.

In particular, $R^3$ is selected from thiazolyl, pyridinyl, pyridazinyl, benzothiazolyl and isoxazole.

When $R^3$ and $R^2$ together form a ring, the ring may be referred to throughout as ring A. In such cases the compound may be of the formula:

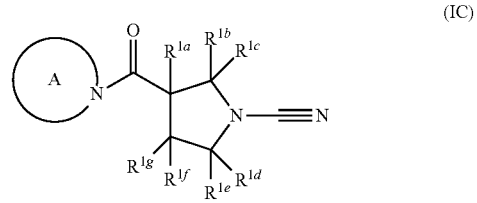

(IC)

or a pharmaceutically acceptable salt thereof, wherein ring A is an optionally substituted monocyclic or bicyclic ring and wherein $R^{1a}$, $R^{1b}$, $R^{1c}$, $R^{1d}$, $R^{1e}$, $R^{1f}$ and $R^{1g}$ are as described herein.

The heterocyclyl or heteroaryl ring of $R^3$ may be defined according to the definition of heterocyclyl and heteroaryl ring found herein and is monocyclic or bicyclic.

Ring A represents a 5 to 10 membered (e.g. 5, 6, 7, 8, 9 or 10 membered) monocyclic or fused bicyclic heterocyclyl or heteroaryl ring which may be optionally substituted with one or more (e.g. one, two, three or four) of -$Q^1$-$(R^4)_n$, in particular one or two of -$Q^1$-$(R^4)_n$.

In particular, ring A may represent a 5 or 6 membered heterocyclyl or heteroaryl ring which may be optionally substituted with one or more (e.g. one, two, three or four) of -$Q^1$-$(R^4)_n$.

Alternatively, ring A may represent a 9 or 10 membered bicyclic heteroaryl or aryl ring which may be optionally substituted with one or more (e.g. one, two, three or four) of -$Q^1$-$(R^4)_n$.

When ring A is a heteroaryl ring, the ring is monocyclic or bicyclic and may comprise one or more (e.g. 1, 2 or 3) additional heteroatoms independently selected from nitrogen, oxygen and sulphur, in particular nitrogen. Examples of nitrogen containing heteroaryl rings include pyridinyl, pyrazinyl, pyrimidinyl, pyridazinyl, pyrrolyl, oxazolyl, thiazolyl, pyrazolyl, triazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzimidazolyl, benzothiazolyl, napthyridinyl, pteridinyl, pyrazinyl, 4H-quinolizinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydropyrrolopyridinyl and dihydrobenzoxazinyl.

The optionally substituted 5 to 10 membered nitrogen-containing monocyclic or bicyclic heterocyclyl or heteroaryl ring may be selected from pyridinyl, pyrazinyl, pyrimidinyl, pyridazinyl, pyrrolyl, oxazolyl, thiazolyl, pyrazolyl, triazolyl, tetrazolyl, indolyl, indolizinyl, isoindolyl, purinyl, furazanyl, imidazolyl, indazolyl, isothiazolyl, isoxazolyl, oxadiazolyl, tetrazolyl, thiadiazolyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, triazolopyridinyl, triazinyl, dihydrophyridinyl, quinoxalinyl, dihydrobenzoxazinyl, dihydropyrrolopyridinyl pyrrolidinyl, piperidinyl, azepanyl, diazepanyl, morpholinyl, oxazolidinyl, oxazinanyl, indolinyl, isoindolinyl, piperazinyl, thiomorpholinyl, homopiperazinyl, hexahydropyrimidinyl, pyrazolinyl, pyrazolidinyl, 4H-quinolizinyl, quinuclidinyl, tetrahydropyridinyl, tetrahydropyrimidinyl, thiazolidinyl, tetrahydroquinolinyl, tetrahydroisoquinolinyl.

In particular, ring A is selected from indolinyl, dihydropyrrolopyridinyl, tetrahydroquinolyl and dihydrobenzoxazinyl.

In all cases described herein, $R^3$ or ring A may be unsubstituted or substituted with one or more -$Q^1$-$(R^4)_n$, wherein each occurrence of -$Q^1(R^4)_n$ is the same or different, wherein;

n is 0 or 1;

$Q^1$ represents halogen, cyano, oxo, nitro, —$OR^5$, —$SR^5$, —$NR^5R^6$, —$CONR^5R^6$, —$NR^5COR^6$, —$NR^5CONR^6R^7$, —$COR^5$, —$C(O)OR^5$, —$SO_2R^5$, —$SO_2NR^5R^6$, —$NR^5SO_2R^6$, —$NR^5SO_2NR^6R^7$, —$NR^5C(O)OR^6$, optionally substituted —$C_1$-$C_6$ alkyl, optionally substituted —$C_1$-$C_6$ alkoxy, optionally substituted —$C_2$-$C_6$ alkenyl, a covalent bond, an oxygen atom, a sulphur atom, —SO—, —$SO_2$—, —CO—, —C(O)O—, —$CONR^5$—, —$NR^5$—, —$NR^5CO$—, —$NR^5CONR^6$—, —$SO_2NR^5$—, $NR^5SO_2$—, —$NR^5SO_2NR^6$—, —$NR^5C(O)O$—, —$NR^5C(O)OR^6$—, optionally substituted $C_1$-$C_6$ alkylene, optionally substituted —$C_1$-$C_6$ alkyleneoxy, or optionally substituted —$C_2$-$C_6$ alkenylene;

$R^4$ is an optionally substituted 3 to 10 membered monocyclic or bicyclic ring;

$R^5$, $R^6$, $R^7$ each independently represent hydrogen optionally substituted $C_1$-$C_6$ alkyl or optionally substituted $C_1$-$C_6$ alkylene.

When n is 1, $R^4$ represents an optionally substituted 3 to 10 membered monocyclic or bicyclic heterocyclyl, cycloalkyl, heteroaryl or aryl ring (when n is 0, $Q^1$ is present and $R^4$ is absent).

$R^3$ or Ring A may be unsubstituted or substituted with one, two, three or four of -$Q^1$-$(R^4)_n$.

In particular, $R^3$ or ring A is either unsubstituted or substituted with one or two of -$Q^1$-$(R^4)_n$. Each occurrence of -$Q^1$-$(R^4)_n$ may be the same or different. Alternatively, $R^3$ or ring A may be either unsubstituted or substituted with one of -$Q^1$-$(R^4)_n$. $Q^1$, $R^4$ and n are as defined herein.

In all cases described herein, $Q^1$ may be selected from halogen (e.g. fluorine, chlorine or bromine), cyano, oxo, nitro, —$OR^5$ (e.g hydroxyl), —$SR^5$ (e.g. thiol), —$NR^5R^6$ (e.g. amino or N,N-dimethylamino), —$CONR^5R^6$ (e.g. amido), —$NR^5COR^6$ (N-acetyl), —$NR^5CONR^6R^7$, —$COR^5$ (e.g. acetyl), —$C(O)OR^5$ (e.g. methoxycarbonyl or ethoxycarbonyl), —$SO_2R^5$ (e.g. methyl sulphonyl), —$SO_2NR^5R^6$ (e.g. dimethylaminosulphonyl), —$NR^5SO_2R^6$, $NR^5SO_2NR^6R^7$, —$NR^5C(O)OR^6$, optionally substituted —$C_1$-$C_4$ alkyl (e.g. propyl, isobutyl or tert butyl), optionally substituted $C_1$-$C_2$ alkyl (e.g. methyl or ethyl), optionally substituted —$C_1$-$C_6$ alkoxy, optionally substituted —$C_2$-$C_6$ alkenyl, optionally substituted —$C_2$-$C_6$ alkynyl, a covalent bond, an oxygen atom, a sulphur atom, —SO—, —$SO_2$—, —CO—, —C(O)O—, —$CONR^5$—, —$NR^5$— (e.g. methylamino), —$NR^5CO$—, —$NR^5CONR^6$—, —$SO_2NR^5$—, —$NR^5SO_2$—, —$NR^5SO_2NR^6$—, —$NR^5C(O)O$—, —$NR^5C(O)OR^6$—, optionally substituted $C_1$-$C_4$ alkylene (e.g. methylene or ethylene) or optionally substituted —$C_2$-$C_4$ alkenylene (e.g. vinyl).

When n is 0, $R^3$ or ring A may be substituted with one or more (e.g. one, two, three or four) $Q^1$ substituents independently selected from halogen (e.g. fluorine, chlorine or bromine), cyano, oxo, nitro, —$OR^5$, —$SR^5$, —$NR^5R^6$, —$CONR^5R^6$, —$NR^5C(O)R^6$, —$NR^5C(O)NR^6R^7$, —C(O)$R^5$, —$C(O)OR^5$, —$SO_2R^6$, $SO_2NR^5R^6$, —$NR^5SO_2R^6$, $NR^5SO_2NR^6R^7$, —$NR^5C(O)OR^6$, —$C_1$-$C_6$ alkyl, —$C_1$-$C_6$ alkoxy, —$C_2$-$C_6$ alkenyl, or —$C_2$-$C_6$ alkynyl, wherein alkyl, alkoxy, alkenyl or alkynyl, may be unsubstituted or substituted with one or more substituents selected from halogen, deutero, hydroxyl, thiol, cyano, amino, nitro and $SF_5$, and wherein $R^5$, $R^6$ and $R^7$ are as defined above.

In particular, when n is 0, $Q^1$ may represent halogen (e.g. fluorine or chlorine), cyano, $C_1$-$C_6$ alkyl or $C_1$-$C_3$ alkyl optionally substituted with one or more fluorine, e.g. $CF_3$. More particularly, when n is 0, $Q^1$ may represent cyano.

In certain instances, n is 0 and $R^3$ or ring A represents a 5 or 6 membered heteroaryl or aryl ring which is optionally substituted with one or more (e.g. one, two, three or four), in particular one or two, $Q^1$ substituents independently selected from halogen (e.g. fluorine or chlorine), $C_1$-$C_6$ alkyl or $C_1$-$C_3$ alkyl optionally substituted with one or more fluorine, e.g. $CF_3$.

Alternatively, n is 0 and $R^3$ or ring A represents a 9 or 10 membered heteroaryl or aryl ring which is optionally substituted with one or more (e.g. one, two, three or four), in particular one or two, $Q^1$ substituents independently selected from halogen (e.g. fluorine or chlorine), cyano, $C_1$-$C_6$ alkyl or $C_1$-$C_3$ alkyl optionally substituted with one or more fluorine, e.g. $CF_3$.

When n is 1, $Q^1$ is a covalent bond or a linker selected from an oxygen atom, a sulphur atom, —SO—, —$SO_2$—, —CO—, —C(O)O—, —$CONR^5$—, —$NR^5$—, —$NR^5CO$—, —$NR^5CONR^6$—, —$SO_2NR^5$—, —$NR^5SO_2$—, —$NR^5SO_2NR^6$—, —$NR^5C(O)O$—, —$NR^5C(O)OR^6$—, $C_1$-$C_6$ alkylene or —$C_2$-$C_6$ alkenylene, wherein the alkylene or alkenylene is optionally substituted with one or more substituents selected from halogen, deutero, hydroxyl, thiol, cyano, amino, nitro and $SF_5$.

In particular, when n is 1, $Q^1$ is a covalent bond, an oxygen atom, $C_1$-$C_6$ alkylene or $C_1$-$C_3$ alkylene, wherein the alkylene is optionally substituted with one or more substitutents selected from from halogen, deutero, hydroxyl, thiol, cyano, amino, nitro and $SF_5$. More particularly, when n is 1, $Q^1$ is a covalent bond.

The ring represented by $R^3$ or ring A may be unsubstituted, mono-substituted, di-substituted or tri-substituted, in particular the ring is either unsubstituted, mono-substituted or di-substituted. It is preferred that the ring represented by $R^3$ or ring A is substituted with a further ring either directly or via a linker, i.e. ring A is substituted with at least one -$Q^1$-$(R^4)_n$ wherein n is 1.

In all cases described herein, $R^4$ represents a 3 to 10 membered monocyclic or bicyclic heterocyclyl, cycloalkyl, heteroaryl or aryl ring. $R^4$ may be selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl, dihydrobenzoxazinyl and tetrahydroisoquinolinyl.

$R^4$ may represent an optionally substituted 5 or 6 membered monocyclic heterocyclyl, cycloalkyl, heteroaryl or aryl ring.

Alternatively, $R^4$ may represent an optionally substituted 9 or 10 membered bicyclic heterocyclyl, cycloalkyl, heteroaryl or aryl ring.

In particular, $R^4$ is selected from substituted or unsubstituted phenyl, pyridinyl, pyrazolyl, piperazinyl and indazolyl. More particularly, $R^4$ is phenyl.

In all cases described herein, $R^4$ may be optionally substituted with one or more substituents selected from halogen, cyano, oxo, nitro, —$OR^8$, —$SR^8$, —$NR^8R^9$, —$CONR^8R^9$, —$NR^8COR^9$, —$NR^8CONR^9R^{10}$, —$COR^8$, $C(O)OR^8$, —$SO_2R^8$, —$SO_2NR^8R^9$, —$NR^8SO_2R^9$, $NR^8SO_2NR^9R^{10}$, —$NR^8C(O)OR^9$, —$C_1$-$C_6$ alkyl, —$C_1$-$C_6$ alkoxy, —$C_2$-$C_6$ alkenyl, —$C_2$-$C_6$ alkynyl, heterocyclyl, cycloalkyl, heteroaryl, aryl, -$Q^2$-$R^8$, -$Q^2$-$NR^8CONR^9R^{10}$, -$Q^2$-$NR^8R^9$, -$Q^2$-$COR^8$, -$Q^2$-$NR^8COR^9$, -$Q^2$-$NR^8C(O)OR^9$, -$Q^2$-$SO_2R^8$, $Q^2$-$CONR^8R^9$, -$Q^2$-$CO_2R^8$, -$Q^2$-$SO_2NR^8R^9$, -$Q^2$-$NR^8SO_2R^9$ and -$Q^2$-$NR^8SO_2NR^9R^{10}$, wherein the alkyl, alkoxy, alkenyl or alkynyl are optionally substituted with one or more substituents selected from halogen, deutero, hydroxyl, thiol, cyano, amino, nitro and $SF_5$ and wherein the heterocyclyl, cycloalkyl, heteroaryl or aryl are optionally substituted; wherein $Q^2$ represents a covalent bond, an oxygen atom, a sulphur atom, —SO—, —$SO_2$—, —CO—, optionally substituted $C_1$-$C_6$ alkylene or optionally substituted $C_2$-$C_6$ alkenylene; and $R^8$, $R^9$ and $R^{10}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^4$ may be substituted with one or more (e.g. one, two, three or four), in particular one or two, substituents independently selected from halogen, cyano, oxo, nitro, —$OR^8$, —$SR^8$, —$NR^8R^9$, —$CONR^8R^9$, —$NR^8COR^9$, —$NR^8CONR^9R^{10}$, —$COR^8$, —$C(O)OR^8$, —$SO_2R^8$, —$SO_2NR^8R^9$, —$NR^8SO_2R^9$, $NR^8SO_2NR^9R^{10}$, —$NR^9C(O)OR^9$, —$C_1$-$C_6$ alkyl, —$C_1$-$C_6$ alkoxy, —$C_2$-$C_6$ alkenyl, —$C_2$-$C_6$ alkynyl, -$Q^2$-$R^8$, -$Q^2$-$NR^8CONR^9R^{10}$, -$Q^2$-$NR^8R^9$, -$Q^2$-$COR^8$, -$Q^2$-$NR^8COR^9$, -$Q^2$-$NR^8C(O)OR^9$, -$Q^2$-$SO_2R^8$, $Q^2$-$CONR^8R^9$, -$Q^2$-$CO_2R^8$, -$Q^2$-$SO_2NR^8R^9$, -$Q^2$-$NR^5SO_2R^9$ and -$Q^2$-$NR^8SO_2NR^9R^{10}$, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and wherein $R^8$, $R^9$, $R^{10}$ each independently represent hydrogen or optionally substituted $C_1$-$C_6$ alkyl, wherein any alkyl, alkoxy, alkenyl, alkynyl, alkylene or alkenylene is optionally substituted with one or more (e.g. one, two, three or four) substituents selected from halogen, deutero, hydroxyl, thiol, cyano, amino, nitro and $SF_5$.

In particular, $R^4$ may be substituted with one or more substituents selected from halogen (e.g. chlorine or fluorine), cyano, —$C_1$-$C_6$ alkyl (e.g. propyl, isobutyl or tert butyl) or $C_1$-$C_2$ alkyl (e.g. methyl or ethyl), —$C_1$-$C_6$ alkoxy (e.g. propoxy) or $C_1$-$C_2$ alkoxy (e.g. methoxy or ethyoxy), or —$NR^8SO_2R^9$ wherein $R^8$ and $R^9$ each independently represent hydrogen or $C_1$-$C_3$ alkyl or $C_3$-$C_6$ cycloalkyl. The alkyl or alkoxy may be optionally substituted with one or more fluorine.

More particularly, $R^4$ may be mono-substituted with a substituent selected from halogen, cyano, —$C_1$-$C_6$ alkyl, —$C_1$-$C_6$ alkoxy or —$NR^8SO_2R^9$ where $R^8$ is hydrogen and $R^9$ is cyclopropane, and wherein the alkyl or alkoxy may be optionally substituted with one or more fluorine.

In addition, or alternatively, $R^4$ may be optionally substituted with a further optionally substituted 3 to 10 membered heterocyclyl, cycloalkyl, heteroaryl or aryl ring, either directly attached or via a linking group. The linking group may be an oxygen atom, a carbonyl or an optionally substituted $C_1$-$C_6$ alkylene. The linking group may be oxygen, —CO— or an alkylene chain, for example, methylene. The 3 to 10 membered ring may be unsubstituted or substituted with one or more (e.g. one, two, three of four), in particular one or two, substituents selected from halogen (for example, fluorine or chlorine), $C_1$-$C_4$ alkyl (e.g. propyl, isobutyl or tert butyl) or $C_1$-$C_2$ alkyl (e.g. methyl or ethyl) wherein the alkyl may be optionally substituted with one or more fluorine. In particular, the 3 to 10 membered ring is unsubstituted.

In particular, $R^4$ may be unsubstituted, mono-substituted or di-substituted. More particularly, $R^4$ is unsubstituted or mono-substituted.

In certain instances, $R^4$ represents a 3 to 10 membered heterocyclyl, cycloalkyl, heteroaryl or aryl ring selected from heterocyclyl, cycloalkyl, heteroaryl or aryl ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl which is either unsubstituted or substituted with one or more (e.g. one, two or three) substituents selected from halogen (e.g. fluorine or chlorine), cyano, oxo, nitro, —$OR^8$, —$SR^8$, —$NR^8R^9$, —$CONR^8R^9$, —$NR^8COR^9$, $NR^8CONR^9R^{10}$, —$COR^8$, —$C(O)OR^8$, —$SO_2R^8$, —$SO_2NR^8R^9$, —$NR^8SO_2R^9$, $NR^8SO_2NR^9R^{10}$, —$NR^8C(O)OR^9$, $C_1$-$C_6$ alkyl, —$C_1$-$C_6$ alkoxy, —$C_2$-$C_6$ alkenyl, —$C_2$-$C_6$ alkynyl, heterocyclyl, cycloalkyl, heteroaryl, aryl, -$Q^2$-$R^8$, -$Q^2$-$NR^8CONR^9R^{10}$, -$Q^2$-$NR^8R^9$, -$Q^2$-$COR^8$, -$Q^2$-$NR^8COR^9$, -$Q^2$-$NR^8C(O)OR^9$, -$Q^2$-$SO_2R^8$, $Q^2$-$CONR^8R^9$, -$Q^2$-$CO_2R^8$, -$Q^2$-$SO_2NR^8R^9$, -$Q^2$-$NR^8SO_2R^9$ and -$Q^2$-$NR^8SO_2NR^9R^{10}$, wherein the alkyl, alkoxy, alkenyl or alkynyl are optionally substituted with one or more substituents selected from halogen, deutero, hydroxyl, thiol, cyano, amino, nitro and $SF_5$ and wherein the heterocyclyl, cycloalkyl, heteroaryl or aryl are optionally substituted, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and $R^8$, $R^9$, $R^{10}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^4$ may represent a ring selected from phenyl, pyrazolyl, indazolyl, imidazolyl and thiazolyl, wherein the ring is unsubstituted or substituted with one or more, in particular one or two, substituents selected from halogen (e.g. fluorine or chlorine), cyano, oxo, nitro, —$OR^8$, —$SR^8$, —$NR^8R^9$, —$CONR^8R^9$, —$NR^8COR^9$, —$NR^8CONR^9R^{10}$, —$COR^8$, —$C(O)OR^8$, —$SO_2R^8$, —$SO_2NR^8R^9$, —$NR^8SO_2R^9$, $NR^8SO_2NR^9R^{10}$, —$NR^8C(O)OR^9$, $C_1$-$C_6$ alkyl, —$C_1$-$C_6$ alkoxy, —$C_2$-$C_6$ alkenyl, —$C_2$-$C_6$ alkynyl, heterocyclyl, cycloalkyl, heteroaryl, aryl, -$Q^2$-$R^8$, -$Q^2$-$NR^8CONR^9R^{10}$, -$Q^2$-$NR^8R^9$, -$Q^2$-$COR^8$, -$Q^2$-$NR^8COR^9$, -$Q^2$-$NR^8C(O)OR^9$, -$Q^2$-$SO_2R^8$, $Q^2$-$CONR^8R^9$, -$Q^2$-$CO_2R^8$, -$Q^2$-$SO_2NR^8R^9$, -$Q^2$-$NR^8SO_2R^9$ and -$Q^2$-$NR^8SO_2NR^9R^{10}$, wherein the alkyl, alkoxy, alkenyl or alkynyl are optionally substituted with one or more substituents selected from halogen, deutero, hydroxyl, thiol, cyano, amino, nitro and $SF_5$ and wherein the heterocyclyl, cycloalkyl, heteroaryl or aryl are optionally substituted, wherein $Q^2$ represents a covalent bond, an oxygen atom, a sulphur atom, —SO—, —$SO_2$—, —CO—, $C_1$-$C_6$ alkylene or optionally substituted $C_2$-$C_6$ alkenylene, and $R^8$, $R^9$, $R^{10}$ each independently represent hydrogen, optionally substituted $C_1$-$C_6$ alkyl, optionally substituted heterocyclyl, optionally substituted heteroaryl, optionally substituted aryl, or an optionally substituted cycloalkyl.

$R^4$ may represent a ring selected from cyclopropyl, cyclobutyl, cyclopentyl, cyclohexyl, cycloheptyl, cyclooctyl, decahydronaphthalenyl, phenyl, naphthyl, naphthalenyl, pyridinyl, pyrazinyl, pyrimidinyl, pyridazinyl, furyl, pyrrolyl, oxazolyl, thiazolyl, pyrazolyl, tetrazolyl, indolyl, indolizinyl, isoindolyl, indolinyl, purinyl, furazanyl, imidazolyl, indazolyl, isothiazolyl, isoxazolyl, oxadiazolyl, tetrazolyl, thiadiazolyl, benzofuranyl, isobenzofuranyl, benzothiophenyl, isobenzothiophenyl, benzimidazolyl, benzothiazolyl, napthyridinyl, pteridinyl, pyrazinyl, quinolinyl, isoquinolinyl, cinnolinyl, phthalazinyl, quinazolinyl, imidazopyridinyl, pyrazolopyridinyl, thiazolopyridinyl, isoindolinyl, triazinyl, dihydrophyridinyl, quinoxalinyl, dihydrobenzoxazinyl, dihydropyrrolopyridinyl, azetidinyl, pyrrolidinyl, piperidinyl, azepanyl, diazepanyl, dihydrofuranyl (e.g. 2,3-dihydrofuranyl, 2,5-dihydrofuranyl), dioxolanyl, morpholinyl, oxazolidinyl, oxazinanyl, indolinyl, isoindolinyl, piperazinyl, tetrahydrofuranyl, thiomorpholinyl, dihydropyranyl (e.g. 3,4-dihydropyranyl, 3,6-dihydropyranyl), homopiperazinyl, dioxanyl, hexahydropyrimidinyl, pyrazolinyl, pyrazolidinyl, 4H-quinolizinyl, quinuclidinyl, tetrahydropyranyl, tetrahydropyridinyl, tetrahydropyrimidinyl, tetrahydrothiophenyl, thiazolidinyl, benzopyranyl, tetrahydroquinolinyl and tetrahydroisoquinolinyl, wherein the ring is unsubstituted or substituted with halogen, cyano, —$C_1$-$C_6$ alkyl, —$C_1$-$C_6$ alkoxy or —$NR^8SO_2R^9$ where $R^8$ and $R^9$ each independently represent hydrogen, $C_1$-$C_3$ alkyl or $C_3$-$C_6$ cycloalkyl, and wherein the alkyl or alkoxy may be optionally substituted with one or more fluorine.

In particular, $R^4$ may be selected from phenyl, pyridinyl, pyrazolyl, piperazinyl and indazolyl wherein the ring is unsubstituted or substituted with one or more (e.g. one, two or three) substituents selected from halogen, cyano, —$C_1$-$C_6$ alkyl, —$C_1$-$C_6$ alkoxy, —$NR^8SO_2R^9$, wherein $R^8$ and $R^9$ each independently represent hydrogen, $C_1$-$C_3$ alkyl or $C_3$-$C_6$ cycloalkyl. The alkyl or alkoxy may be optionally substituted with one or more fluorine.

The present invention further relates to compounds of formula (I), or pharmaceutically acceptable salts thereof, wherein:

$R^{1a}$ represents hydrogen, fluorine or together with $R^2$ forms a 5 or 6 membered optionally substituted ring;

$R^{1b}$, $R^{1c}$, $R^{1d}$, $R^{1e}$ and $R^{1f}$ each represent hydrogen;

$R^{1g}$ represents hydrogen, unsubstituted or substituted methyl, or together with $R^2$ forms a 5 or 6 membered optionally substituted ring;

$R^2$ represents an optionally substituted $C_1$-$C_3$ alkyl, or together with $R^{1a}$ or $R^{1g}$ forms a 5 or 6 membered optionally substituted ring, or together with $R^3$ forms an optionally substituted 5 to 10 membered monocyclic or bicyclic ring;

$R^3$ represents an optionally substituted 5 to 10 membered monocyclic or bicyclic ring or together with $R^2$ forms an optionally substituted 5 to 10 membered monocyclic or bicyclic ring;

L represents a covalent bond or optionally substituted $C_1$-$C_3$ alkylene.

The present invention further relates to compounds of formula (I), or pharmaceutically acceptable salts thereof, wherein:

$R^{1a}$ represents hydrogen, fluorine or together with $R^2$ forms a 5 or 6 membered optionally substituted ring;

$R^{1b}$, $R^{1c}$, $R^{1d}$, $R^{1e}$ and $R^{1f}$ each represent hydrogen;

$R^{1g}$ represents hydrogen, unsubstituted or substituted methyl, or together with $R^2$ forms a 5 or 6 membered optionally substituted ring;

$R^2$ represents an optionally substituted $C_1$-$C_3$ alkyl, or together with $R^{1a}$ or $R^{1g}$ forms a 5 or 6 membered optionally substituted ring, or together with $R^3$ forms an optionally substituted 5 to 10 membered monocyclic or bicyclic ring;

$R^3$ represents an optionally substituted 5 to 10 membered monocyclic or bicyclic ring or together with $R^2$ forms an optionally substituted 5 to 10 membered monocyclic or bicyclic ring;

L represents a covalent bond or optionally substituted $C_1$-$C_3$ alkylene;

wherein $R^3$ or the ring formed by $R^3$ together with $R^2$ is unsubstituted or substituted with one or two -$Q^1$-$(R^4)_n$, which can be the same or different but which are preferably different, wherein $Q^1$, $R^4$ and n are as defined herein.

In one embodiment, $R^3$ or the ring formed by $R^2$ together with $R^3$ is unsubstituted or substituted with one or two -$Q^1$-$(R^4)_n$, where at least one -$Q^1$-$(R^4)_n$ moiety has n is 1.

The present invention further relates to compounds of formula (I), or a pharmaceutically acceptable salt thereof, wherein:

$R^{1a}$ represents hydrogen, fluorine or together with $R^2$ forms an optionally substituted 5 or 6 membered ring;

$R^{1b}$, $R^{1c}$, $R^{1d}$, $R^{1e}$ and $R^{1f}$ each represent hydrogen;

$R^{1g}$ represents hydrogen, unsubstituted or substituted methyl, or together with $R^2$ forms a 5 or 6 membered optionally substituted ring;

$R^2$ represents an optionally substituted $C_1$-$C_3$ alkyl, or together with $R^{1a}$ or $R^{1g}$ forms a 5 or 6 membered optionally substituted ring, or together with $R^3$ forms an optionally substituted 5 to 10 membered monocyclic or bicyclic ring selected from indolinyl, dihydropyrrolopyridinyl, tetrahydroquinolyl and dihydrobenzoxazinyl;

$R^3$ represents an optionally substituted 5 to 10 membered monocyclic or bicyclic ring selected from thiazolyl, pyridinyl, pyridazinyl, benzothiazolyl and isoxazolyl, $R^3$ together with $R^2$ forms an optionally substituted 5 to 10 membered monocyclic or bicyclic ring selected from indolinyl, dihydropyrrolopyridinyl, tetrahydroquinolinyl and dihydrobenzoxazinyl;

wherein the 5 to 10 membered monocyclic or bicyclic ring may be optionally substituted with one or two -$Q^1$-($R^4$)$_n$, wherein $Q^1$, $R^4$ and n are as defined herein.

Examples of the heteroaryl and aryl ring represented by $R^3$ include those shown below:

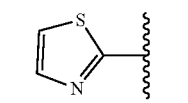

A

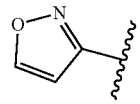

B

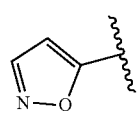

C

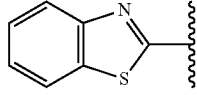

D

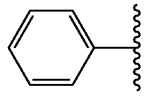

E

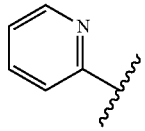

F

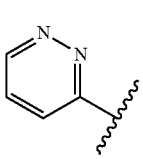

G

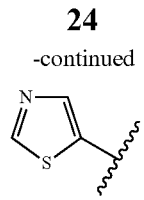

H wherein

represents the point of attachment to the remainder of the molecule, i.e. to the amide nitrogen through L, and wherein the rings are optionally substituted with one or more of -$Q^1$-($R^4$).

Examples of the heteroaryl and heterocyclyl ring formed when $R^3$ is linked to $R^2$ include those shown below:

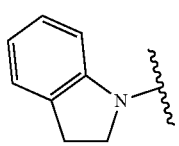

A

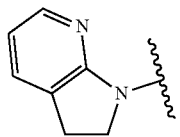

B

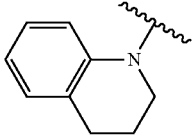

C

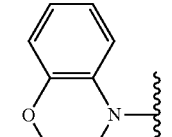

D wherein

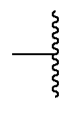

represents the point of attachment to the remainder of the molecule, i.e. to the amide carbonyl, and wherein the rings are optionally substituted with one or more of -$Q^1$-($R^4$)$_n$.

Examples of novel compounds of formula I include:
1-cyano-N-ethyl-N-(4-phenylthiazol-2-yl)pyrrolidine-3-carboxamide
1-cyano-N-ethyl-N-(5-phenylthiazol-2-yl)pyrrolidine-3-carboxamide
(S)-1-cyano-N-methyl-N-(5-phenylthiazol-2-yl)pyrrolidine-3-carboxamide (S)-1-cyano-N-methyl-N-(4-phenylpyridin-2-yl)pyrrolidine-3-carboxamide
(S)-1-cyano-N-methyl-N-(6-phenylpyridin-2-yl)pyrrolidine-3-carboxamide
1-cyano-N-isopropyl-N-(5-(pyridin-4-yl)thiazol-2-yl)pyrrolidine-3-carboxamide
1-cyano-N-isopropyl-N-(4-phenylthiazol-2-yl)pyrrolidine-3-carboxamide
1-cyano-3-fluoro-N-methyl-N-(5-phenylthiazol-2-yl)pyrrolidine-3-carboxamide
N-(benzo[d]thiazol-2-yl)-1-cyano-3-fluoro-N-methylpyrrolidine-3-carboxamide
(S)-3-(4-phenylindoline-1-carbonyl)pyrrolidine-1-carbonitrile
(R)-3-(6-phenylindoline-1-carbonyl)pyrrolidine-1-carbonitrile
(S)-3-(5-(3-chlorophenyl)indoline-1-carbonyl)pyrrolidine-1-carbonitrile
(3S,4S)-3-(5-(2-chlorophenyl)indoline-1-carbonyl)-4-methylpyrrolidine-1-carbonitrile
3-fluoro-3-(5-phenylindoline-1-carbonyl)pyrrolidine-1-carbonitrile
3-fluoro-3-(6-phenylindoline-1-carbonyl)pyrrolidine-1-carbonitrile
3-fluoro-3-(6-phenyl-2,3-dihydro-1H-pyrrolo[2,3-b]pyridine-1-carbonyl)pyrrolidine-1-carbonitrile
(R)-3-(5-phenylindoline-1-carbonyl)pyrrolidine-1-carbonitrile
(S)-3-(5-phenylindoline-1-carbonyl)pyrrolidine-1-carbonitrile
(3S,4S)-3-methyl-4-(5-phenylindoline-1-carbonyl)pyrrolidine-1-carbonitrile
(3R,4R)-3-methyl-4-(5-phenylindoline-1-carbonyl)pyrrolidine-1-carbonitrile
(S)-3-(5-phenyl-2,3-dihydro-1H-pyrrolo[2,3-b]pyridine-1-carbonyl)pyrrolidine-1-carbonitrile
3-fluoro-3-(5-phenyl-2,3-dihydro-1H-pyrrolo[2,3-b]pyridine-1-carbonyl)pyrrolidine-1-carbonitrile
(S)-3-(6-phenyl-1,2,3,4-tetrahydroquinoline-1-carbonyl)pyrrolidine-1-carbonitrile
(R)-3-(7-phenyl-3,4-dihydro-2H-benzo[b][1,4]oxazine-4-carbonyl)pyrrolidine-1-carbonitrile
(R)-3-(6-phenyl-3,4-dihydro-2H-benzo[b][1,4]oxazine-4-carbonyl)pyrrolidine-1-carbonitrile
(R)-3-(8-phenyl-3,4-dihydro-2H-benzo[b][1,4]oxazine-4-carbonyl)pyrrolidine-1-carbonitrile
(S)-3-(4-phenyl-2,3-dihydro-1H-pyrrolo[2,3-b]pyridine-1-carbonyl)pyrrolidine-1-carbonitrile
(S)-3-(4-(3-chlorophenyl)-2,3-dihydro-1H-pyrrolo[2,3-b]pyridine-1-carbonyl)pyrrolidine-1-carbonitrile
(S)-1-(1-cyanopyrrolidine-3-carbonyl)-5-(1-methyl-1H-pyrazol-4-yl)indoline-6-carbonitrile
(R)-3-(7-(1H-pyrazol-1-yl)-3,4-dihydro-2H-benzo[b][1,4]oxazine-4-carbonyl)pyrrolidine-1-carbonitrile
(S)-1-cyano-N-methyl-N-(5-phenylpyridin-2-yl)pyrrolidine-3-carboxamide
(R)-1-cyano-N-methyl-N-(5-phenylpyridazin-3-yl)pyrrolidine-3-carboxamide
1-cyano-3-fluoro-N-methyl-N-(5-phenylisoxazol-3-yl)pyrrolidine-3-carboxamide
(3S,4S)-1-cyano-4-(hydroxymethyl)-N-methyl-N-(5-phenylthiazol-2-yl)pyrrolidine-3-carboxamide
3-(5-(1-benzyl-1H-pyrazol-5-yl)indoline-1-carbonyl)-3-fluoropyrrolidine-1-carbonitrile
3-fluoro-3-(5-(1-methyl-1H-pyrazol-5-yl)indoline-1-carbonyl)pyrrolidine-1-carbonitrile
3-fluoro-3-(5-(4-(4-methylpiperazin-1-yl)phenyl)indoline-1-carbonyl)pyrrolidine-1-carbonitrile
3-fluoro-3-(5-(4-(4-methylpiperazine-1-carbonyl)phenyl)indoline-1-carbonyl)pyrrolidine-1-carbonitrile
3-fluoro-3-(5-(1-methyl-1H-indazol-5-yl)indoline-1-carbonyl)pyrrolidine-1-carbonitrile
3-fluoro-3-(5-(2-fluoro-5-methylphenyl)indoline-1-carbonyl)pyrrolidine-1-carbonitrile
3-fluoro-3-(5-(5-methyl-1H-indazol-4-yl)indoline-1-carbonyl)pyrrolidine-1-carbonitrile
N-(3-(1-(1-cyano-3-fluoropyrrolidine-3-carbonyl)indolin-5-yl)phenyl)cyclopropanesulfonamide
3-fluoro-3-(5-(6-methoxypyridin-3-yl)indoline-1-carbonyl)pyrrolidine-1-carbonitrile
(R)-1-cyano-N-(5-(4-cyanophenyl)pyridin-2-yl)-N-ethylpyrrolidine-3-carboxamide
N-(benzo[d]thiazol-2-ylmethyl)-1-cyano-N-methylpyrrolidine-3-carboxamide
1-cyano-N-methyl-N-((3-phenylisoxazol-5-yl)methyl)pyrrolidine-3-carboxamide
1-cyano-N-methyl-N-((2-phenylthiazol-4-yl)methyl)pyrrolidine-3-carboxamide
(3aR,6aS)-4-oxo-5-(5-phenylthiazol-2-yl)hexahydropyrrolo[3,4-c]pyrrole-2(1H)-carbonitrile
7-([1,1'-biphenyl]-3-yl)-6-oxo-2,7-diazaspiro[4.4]nonane-2-carbonitrile
(R)-3-(4-(3-ethylphenyl)indoline-1-carbonyl)pyrrolidine-1-carbonitrile
(R)-1-(1-cyanopyrrolidine-3-carbonyl)-N-methyl-4-phenylindoline-6-carboxamide
(R)-1-(1-cyanopyrrolidine-3-carbonyl)-4-(3-ethylphenyl)-N-methylindoline-6-carboxamide
(R)-3-(5-(1H-indazol-4-yl)-2,3-dihydro-1H-pyrrolo[2,3-b]pyridine-1-carbonyl)pyrrolidine-1-carbonitrile
(S)-3-(5-(1H-indazol-4-yl)-2,3-dihydro-H-pyrrolo[2,3-b]pyridine-1-carbonyl)pyrrolidine-1-carbonitrile
3-(5-phenyl-2,3-dihydro-1H-pyrrolo[3,2-b]pyridine-1-carbonyl)pyrrolidine-1-carbonitrile
(trans)-3-methyl-4-(5-phenyl-2,3-dihydro-1H-pyrrolo[2,3-b]pyridine-1-carbonyl)pyrrolidine-1-carbonitrile
3-fluoro-3-(5-(1-isobutyl-1H-pyrazol-5-yl)indoline-1-carbonyl)pyrrolidine-1-carbonitrile
3-(5-(1-benzyl-1H-pyrazol-4-yl)indoline-1-carbonyl)-3-fluoropyrrolidine-1-carbonitrile
3-fluoro-3-(5-(1-(pyridin-2-ylmethyl)-1H-pyrazol-5-yl)indoline-1-carbonyl)pyrrolidine-1-carbonitrile
N-benzyl-1-(1-cyano-3-fluoropyrrolidine-3-carbonyl)indoline-5-carboxamide
3-(5-(1-(2-chlorobenzyl)-1H-pyrazol-5-yl)indoline-1-carbonyl)-3-fluoropyrrolidine-1-carbonitrile
3-(5-(1-(3-chlorobenzyl)-1H-pyrazol-5-yl)indoline-1-carbonyl)-3-fluoropyrrolidine-1-carbonitrile
3-(5-(1-(4-chlorobenzyl)-1H-pyrazol-5-yl)indoline-1-carbonyl)-3-fluoropyrrolidine-1-carbonitrile
3-fluoro-3-(5-(1-(pyridin-3-ylmethyl)-1H-pyrazol-5-yl)indoline-1-carbonyl)pyrrolidine-1-carbonitrile
3-fluoro-3-(5-(pyridin-3-yl)indoline-1-carbonyl)pyrrolidine-1-carbonitrile
(R)-3-fluoro-3-(5-phenylindoline-1-carbonyl)pyrrolidine-1-carbonitrile
(S)-3-fluoro-3-(5-phenylindoline-1-carbonyl)pyrrolidine-1-carbonitrile
(R)-3-(5-(3-chlorophenyl)-2,3-dihydro-1H-pyrrolo[2,3-b]pyridine-1-carbonyl)-3-fluoropyrrolidine-1-carbonitrile
(S)-3-(5-(3-chlorophenyl)-2,3-dihydro-1H-pyrrolo[2,3-b]pyridine-1-carbonyl)-3-fluoropyrrolidine-1-carbonitrile.

Preferred compounds are 3-fluoro-3-(5-(2-fluoro-5-methylphenyl)indoline-1-carbonyl)pyrrolidine-1-carbonitrile or (R)-3-(5-(3-chlorophenyl)-2,3-dihydro-1H-pyrrolo[2,3-b]pyridine-1-carbonyl)-3-fluoropyrrolidine-1-carbonitrile.

It should be noted that each of the chemical compounds listed above represents a particular and independent aspect of the invention.

According to a further aspect of the invention there is provided a process for the preparation of a compound of formula (I) or a pharmaceutically acceptable salt thereof comprising the steps of reacting an acid of formula (III) with a compound $R^3$-L-N($R^2$)H to form an amide:

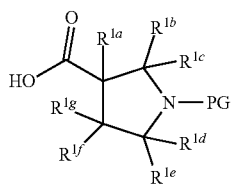

(III)

Where $R^{1a}$-$R^{1g}$ are as defined elsewhere and PG is an amine protecting group. The protecting group may be but is not limited to BOC. It is clear to a person skilled in the art to combine or adjust such a protecting chemical group. After coupling of $R^3$-L-N($R^2$)H to form an amide, the protecting group may be removed to leave the free amine according to formula (IV) which can then be treated with cyanogen bromide to form compounds according to formula (I).

According to a further aspect of the invention there is provided a process for the preparation of a compound of formula (I) or a pharmaceutically acceptable salt thereof comprising the steps of reacting an amine of formula (IV) with cyanogen bromide to form N—CN compounds:

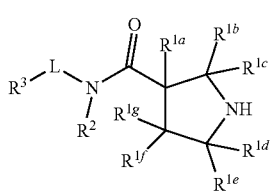

(IV)

Where $R^{1a}$-$R^{1g}$, $R^2$, $R^3$ and L are as defined elsewhere.

According to a further aspect of the invention there is provided a pharmaceutical composition comprising a compound of the invention.

Pharmaceutical compositions of this invention comprise any of the compounds of the invention combined with any pharmaceutically acceptable carrier, adjuvant or vehicle. Examples of pharmaceutically acceptable carriers, are known to those skilled in the art and include but are not limited to preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be in the form of, for example, tablets, capsules, powders, granules, elixirs, lozenges, suppositories, syrups and liquid preparations including suspensions and solutions. The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compounds of the invention may be used in the treatment of disorders and diseases related to DUB inhibition, particularly USP30 inhibition.

Conditions Involving Mitochondrial Dysfunction

The compounds of the invention can be used in the treatment of disorders or diseases having a component relating to mitochondrial dysfunction, particularly disorders or diseases linked to DUB activity. More particularly, disorders or diseases link to USP30 activity.

The compounds described herein may be used in the manufacture of a medicament for the treatment of conditions involving mitochondrial dysfunction.

In a further aspect of the invention there is provided a method of treatment or prevention of a condition involving mitochondrial dysfunction, the method comprising administering a pharmaceutically effective amount of a compound of the invention or a pharmaceutical composition thereof to an individual diagnosed with a condition involving mitochondrial dysfunction.

Mitochondrial dysfunctions result from defects of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised. Diseases of the mitochondria appear most often in organs that are very energy demanding such as the brain, heart, liver, skeletal muscles, kidney and the endocrine and respiratory system.

The condition involving mitochondrial dysfunction may be selected from a condition involving a mitophagy defect, a condition involving a mutation in mitochondrial DNA, a condition involving mitochondrial oxidative stress, a condition involving a defect in mitochondrial membrane potential, mitochondrial biogenesis, a condition involving a defect in mitochondrial shape or morphology, and a condition involving a lysosomal storage defect.

In particular, the condition involving mitochondrial dysfunction may be selected from a neurodegenerative disease; multiple sclerosis (MS), mitochondrial myopathy, encephalopathy, lactic acidosis, and stroke-like episodes (MELAS) syndrome; Leber's hereditary optic neuropathy (LHON); cancer; neuropathy, ataxia, retinitis pigmentosa-maternally inherited Leigh syndrome (NARP-MILS); Danon disease; diabetes; diabetic nephropathy; metabolic disorders; heart failure; ischemic heart disease leading to myocardial infarction; psychiatric diseases, for example schizophrenia; multiple sulfatase deficiency (MSD); mucolipidosis II (ML II); mucolipidosis III (ML III); mucolipidosis IV (ML IV); GM1-gangliosidosis (GM1); neuronal ceroid-lipofuscinoses (NCL1); Alpers disease; Barth syndrome; Beta-oxidation defects; camitine-acyl-camitine deficiency; camitine deficiency; creatine deficiency syndromes; co-enzyme Q10 deficiency; complex I deficiency; complex II deficiency; complex III deficiency; complex IV deficiency; complex V deficiency; COX deficiency; chronic progressive external ophthalmoplegia syndrome (CPEO); CPT I deficiency; CPT II deficiency; glutaric aciduria type II; Kearns-Sayre syndrome; lactic acidosis; long-chain acyl-CoA dehydrogenase deficiency (LCHAD); Leigh disease or syndrome; lethal infantile cardiomyopathy (LIC); Luft disease; glutaric aciduria type II; medium-chain acyl-CoA dehydrogenase deficiency (MCAD); myoclonic epilepsy and ragged-red fiber (MERRF) syndrome; mitochondrial cytopathy; mitochondrial recessive ataxia syndrome; mitochondrial DNA depletion syndrome; myoneurogastointestinal disorder and encephalopathy; Pearson syndrome; pyruvate dehydrogenase deficiency; pyruvate carboxylase deficiency; POLG mutations; medium/short-chain 3-hydroxyacyl-CoA dehydrogenase (M/SCHAD) deficiency; very long-chain acyl-CoA dehydrogenase (VLCAD) deficiency; and age-dependent decline in cognitive function and muscle-strength.

The condition involving mitochondrial dysfunction may be a CNS disorder, for example a neurodegenerative disease.

Neurodegenerative diseases include, but are not limited to, Parkinson's disease, Alzheimer's disease, amyotrophic lateral sclerosis (ALS), Huntington's disease, ischemia, stroke, dementia with Lewy bodies, and frontotemporal dementia.

In a particular embodiment, the compounds of the invention are useful in the treatment of Parkinson's disease, including, but not limited to, PD related to mutations in α-synuclein, parkin and PINK1, autosomal recessive juvenile Parkinson's disease (AR-JP) where parkin is mutated.

The compounds of the invention or pharmaceutical compositions thereof as described herein may be combined with one or more additional agents when used for the treatment of conditions involving mitochondrial dysfunction. The compounds may be combined with one or more additional agents selected from levodopa, a dopamine agonist, a monoamino oxygenase (MAO) B inhibitor, a catechol O-methyltransferase (COMT) inhibitor, an anticholinergic, riluzole, amantadine, a cholinesterase inhibitor, memantine, tetrabenazine, an antipsychotic, diazepam, clonazepam, an antidepressant, and an anti-convulsant.

Cancer

Compounds of the invention also have use in the treatment of cancer and more particularly in the treatment of cancer linked to DUB activity, especially USP30 activity.

The compounds as described herein may also be used in the manufacture of a medicament for the treatment of a cancer. In a further aspect of the invention there is provided a method of treatment or prevention of a cancer, the method comprising administering a pharmaceutically effective amount of a compound of the invention or a pharmaceutical composition thereof to an individual suffering from a cancer.

The compounds of the invention also have use in the treatment of cancer linked to mitochondrial dysfunction.

In one embodiment, the compounds of the invention have use in the treatment of cancer where apoptotic pathways are dysregulated and more particularly where proteins of the BCL-2 family are mutated, or over or under expressed.

References to "cancer" or "tumour" include but are not limited to breast, ovarian, prostate, lung, kidney, gastric, colon, testicular, head and neck, pancreas, brain, melanoma, bone or other cancers of tissue organs and cancers of the blood cells such as lymphomas and leukaemias. Particular cancers include lymphoma, multiple myeloma, colorectal cancer, and non-small cell lung carcinoma.

The compounds of the invention or pharmaceutical compositions thereof as described herein may be combined with one or more additional agents when used for the treatment of cancer. The compounds may be combined with an additional anti-tumour therapeutic agent, for example chemotherapeutic drugs or inhibitors of other regulatory proteins. In one embodiment the additional anti-tumour therapeutic agent is a BH-3 mimetic. In a further embodiment BH-3 mimetics may be selected from but not limited to one or more of ABT-737, ABT-199, ABT-263, and Obatoclax. In a further embodiment the additional anti-tumour agent is a chemotherapeutic agent. Chemotherapeutic agents may be selected from but not limited to, olaparib, mitomycin C, cisplatin, carboplatin, oxaliplatin, ionizing radiation (IR), camptothecin, irinotecan, topotecan, temozolomide, taxanes, 5-fluoropyrimidines, gemcitabine, and doxorubicin.

Dosage Forms

For treating a mitochondrial dysfunction disorder, the pharmaceutical compositions of the invention may be designed for administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc. For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

For treating a CNS disorder, the compounds of the invention must have the ability to pass across the blood-brain barrier. As such, such compounds have the ability to enter the central nervous system of a patient. Alternatively, the pharmaceutical compositions of the present invention can bypass the blood brain barrier through use of compositions and methods known in the art for bypassing the blood brain barrier or can be injected directly into the brain. Suitable areas for injection include the cerebral cortex, cerebellum, midbrain, brainstem, hypothalamus, spinal cord and ventricular tissue, and areas of the PNS including the carotid body and the adrenal medulla. Further dosage forms include those suitable for oral delivery including, but not limited to tablets, dragees, powders, elixirs, syrups, liquid preparations including suspensions, sprays, inhalants, tablets, lozenges, emulsions, solutions, cachets, granules and capsules. For parenteral administration, preparations include sterile aqueous, aqueous-organic, and organic solutions, suspensions and emulsions.

For treating a cancer, the pharmaceutical compositions of the invention may be administered in any effective manner suitable for targeting cancer cells, for example orally in any orally acceptable dosage form including, but not limited to tablets, dragees, powders, elixirs, syrups, liquid preparations including suspensions, sprays, inhalants, tablets, lozenges, emulsions, solutions, cachets, granules and capsules. Preparations according to the invention for parenteral administration include sterile aqueous, aqueous-organic, and organic solutions, suspensions and emulsions.

Such dosage forms are prepared according to techniques known in the art of pharmaceutical formulation. When in the form of sprays or inhalants the pharmaceutical compositions may be administered nasally. Suitable formulations for this purpose are known to those skilled in the art.

The pharmaceutical compositions of the invention may be administered by injection and may be in the form of a sterile liquid preparation for injection, including liposome preparations. The pharmaceutical compositions of the invention may also be in the form of suppositories for rectal administration. These are formulated so that the pharmaceutical composition is solid at room temperature and liquid at body temperature to allow release of the active compound.

The dosages may be varied depending upon the requirements of the patient, the severity of the condition being treated, and the compound being employed. Determination of the proper dosage for a particular situation is within the remit of the person skilled in the skill of the art. Generally, treatment is initiated with smaller dosages which are less than the optimal dose of the compound. Thereafter the dosage is increased by small increments until the optimum effect under the circumstances is reached.

The magnitude of an effective dose of a compound will, of course, vary with the nature of the severity of the condition to be treated and with the particular compound and its route of administration. The selection of appropriate dosages is within the ability of one of ordinary skill in this art, without undue burden. The daily dose range is about 10 g to about 100 mg per kg body weight of a human and non-human animal and in general may be around 10 g to 30 mg per kg body weight per dose. The above dose may be given from one to three times per day.

Synthetic Methodologies

Compounds of the invention may be prepared via a variety of synthetic routes. Exemplary routes to certain compounds of the invention are shown below. Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

Those skilled in the art appreciate that, where appropriate, the individual transformations within a scheme can be completed in a different order. The following schemes describe general synthetic methods whereby intermediate and target compounds of the present invention may be prepared. Additional representative compounds and stereoisomers, racemic mixtures, diastereomers and enantiomers thereof can be synthesized using the intermediates prepared in accordance to the general schemes and other materials, compounds and reagents known to those skilled in the art. All such compounds, stereoisomers, racemic mixtures, diastereomers and enantiomers thereof are intended to be encompassed within the scope of the present invention.

All the compounds were characterised by liquid chromatography-mass spectroscopy (LCMS) and $^1$H NMR.

Abbreviations:
BOC Tert-butyloxycarbonyl
br Broad (NMR signal)
d Doublet (NMR signal)
dba Dibenzylideneacetone
DCC N,N'-dicyclohexylcarbodiimide
DCM Dichloromethane
DIAD Diisopropyl azodicarboxylate
DIPEA Diisopropylethylamine
DMF N,N'-Dimethylformamide
DMS Dimethylsulphide
DMSO Dimethylsulphoxide
dppf 1,1'-Bis(diphenylphosphino)ferrocene
EDC 1-Ethyl-3-(3-dimethylaminopropyl)carbodiimide
ES Electrospray
EtOAc Ethyl acetate
EtOH Ethanol
h Hour(s)
HATU 1-[Bis(dimethylamino)methylene]-1H-1,2,3-triazolo[4,5-b]pyridinium 3-oxid hexafluorophosphate
HBTU O-Benzotriazole-N,N,N',N'-tetramethyl-uronium-hexafluoro-phosphate
HOBT 1-Hydroxybenzotriazole
IPA Isopropyl alcohol
m Multiplet (NMR signal)
MeCN Acetonitrile
MeOH Methanol
min Minute(s)
PE Petroleum Ether
Psi Pounds per Square Inch (pressure)
rt Room temperature
RT Retention time
s Singlet (NMR signal)
t Triplet (NMR signal)
T3P 2,4,6-Tripropyl-1,3,5,2,4,6-trioxatriphosphorinane-2,4,6-trioxide
TEA Triethylamine
TFA Trifluoroacetic acid
THF Tetrahydrofuran
TLC Thin Layer Chromatography
Xantphos 4,5-Bis(diphenylphosphino)-9,9-dimethylxanthene Analytical Methods:

| LCMS Method A | |
|---|---|
| Column | X-bridge C18, 50 × 4.6 mm, 3.5 μm or equivalent |
| Mobile Phase | (A) 0.1% Ammonia in water |
| | (B) 0.1% Ammonia in MeCN |
| Flow Rate | 1.0 ml/min |

| | Time | % B |
|---|---|---|
| Gradient | 0.01 | 5 |
| | 5.00 | 90 |
| | 5.80 | 95 |
| | 7.20 | 95 |
| | 7.21 | 5 |
| | 10.00 | 5 |

| LCMS Method B | |
|---|---|
| Column | BEH C18, 50 × 2.1 mm, 1.7 μm or equivalent |
| Mobile Phase | (A) 5 mM Ammonium acetate + 0.1% Formic acid in water |
| | (B) 0.1% Formic acid in MeCN |
| Flow Rate | 0.45 ml/min |

| | Time | % B |
|---|---|---|
| Gradient | 0.01 | 2 |
| | 0.50 | 2 |
| | 5.00 | 90 |
| | 6.00 | 95 |
| | 7.00 | 95 |
| | 7.01 | 2 |
| | 8.00 | 2 |

LCMS Method C

| Column | BEH C18, 50 × 2.1 mm, 1.7 μm or equivalent |
|---|---|
| Mobile Phase | (A) 5 mM Ammonium acetate + 0.1% Formic acid in water |
| | (B) 0.1% Formic acid in MeCN |
| Flow Rate | 0.55 ml/min |

| | Time | % B |
|---|---|---|
| Gradient | 0.01 | 5 |
| | 0.40 | 5 |
| | 0.80 | 35 |
| | 1.20 | 55 |
| | 2.50 | 100 |
| | 3.30 | 100 |
| | 3.31 | 5 |
| | 4.00 | 5 |

LCMS Method D

| Column | Agilent TC-C18, 50 × 2.1 mm, 5 μm |
|---|---|
| Mobile Phase | (A) 0.04% TFA in water |
| | (B) 0.02% TFA in MeCN |
| Flow Rate | 0.80 ml/min |

| | Time | % B |
|---|---|---|
| Gradient | 0 | 0 |
| | 0.4 | 0 |
| | 3.4 | 100 |
| | 4 | 100 |
| Temperature | 40° C. | |

LCMS Method E

| Column | Agilent TC-C18, 50 × 2.1 mm, 5 μm |
|---|---|
| Mobile Phase | (A) 0.04% TFA in water |
| | (B) 0.02% TFA in MeCN |
| Flow Rate | 0.80 ml/min |

| | Time | % B |
|---|---|---|
| Gradient | 0.01 | 1 |
| | 3.40 | 100 |
| | 4.00 | 100 |
| | 4.01 | 1 |
| | 4.50 | 1 |

LCMS Method F

| Column | Agilent TC-C18, 50 × 2.1 mm, 5 μm or equivalent |
|---|---|
| Mobile Phase | (A) 0.04% TFA in water |
| | (B) 0.02% TFA in MeCN |
| Flow Rate | 0.80 ml/min |

| | Time | % B |
|---|---|---|
| Gradient | 0.01 | 10 |
| | 3.40 | 100 |
| | 4.00 | 100 |
| | 4.01 | 10 |
| | 4.50 | 10 |

LCMS Method G

| Column | XBridge Shield RP18, 50 × 2.1 mm, 5 μm or equivalent |
|---|---|
| Mobile Phase | (A) 0.05% Ammonia in water |
| | (B) MeCN |
| Flow Rate | 0.80 ml/min |

| | Time | % B |
|---|---|---|
| Gradient | 0.01 | 5 |
| | 3.40 | 100 |
| | 4.00 | 100 |
| | 4.01 | 5 |
| | 4.50 | 5 |

Chiral HPLC Method A

| Column | Chiral Pak IB, 250 × 4.6 mm, 5 μm or equivalent |
|---|---|
| Mobile Phase | (A) 0.1% TFA in n-hexane |
| | (B) 0.1% TFA in EtOH |
| Flow Rate | 1.0 ml/min |

| | Time | % B |
|---|---|---|
| Gradient | 0.01 | 20 |
| | 3 | 20 |
| | 10 | 55 |
| | 15 | 80 |
| | 25 | 80 |
| | 25.01 | 20 |
| | 30 | 20 |

Chiral SFC Method X

| Column | Chiralcel OX-H, 250 × 4.6 mm, 5 μm or equivalent |
|---|---|
| Mobile Phase | (A) Liquid $CO_2$ |
| | (B) IPA:MeCN (50:50) |
| Flow Rate | 3.0 ml/min |

| | Time | % B |
|---|---|---|
| Gradient | 0.01 | 40 |
| | 5 | 40 |

Chiral SFC Method Y

| Column | Chiralpak AD-H, 250 × 4.6 mm, 5 μm or equivalent |
|---|---|
| Mobile Phase | (A) Liquid $CO_2$ |
| | (B) IPA:MeCN (50:50) |
| Flow Rate | 3.0 ml/min |

| | Time | % B |
|---|---|---|
| Gradient | 0.01 | 25 |
| | 10 | 25 |

Chiral SFC Method Z

| Column | Chiralcel OX-H, 250 × 4.6 mm, 5 μm or equivalent |
|---|---|
| Mobile Phase | (A) Liquid $CO_2$ |
| | (B) 0.1% Diethylamine in MeOH |
| Flow Rate | 4.0 ml/min |

| | Time | % B |
|---|---|---|
| Gradient | 0.01 | 45 |
| | 10 | 45 |

General Scheme 1

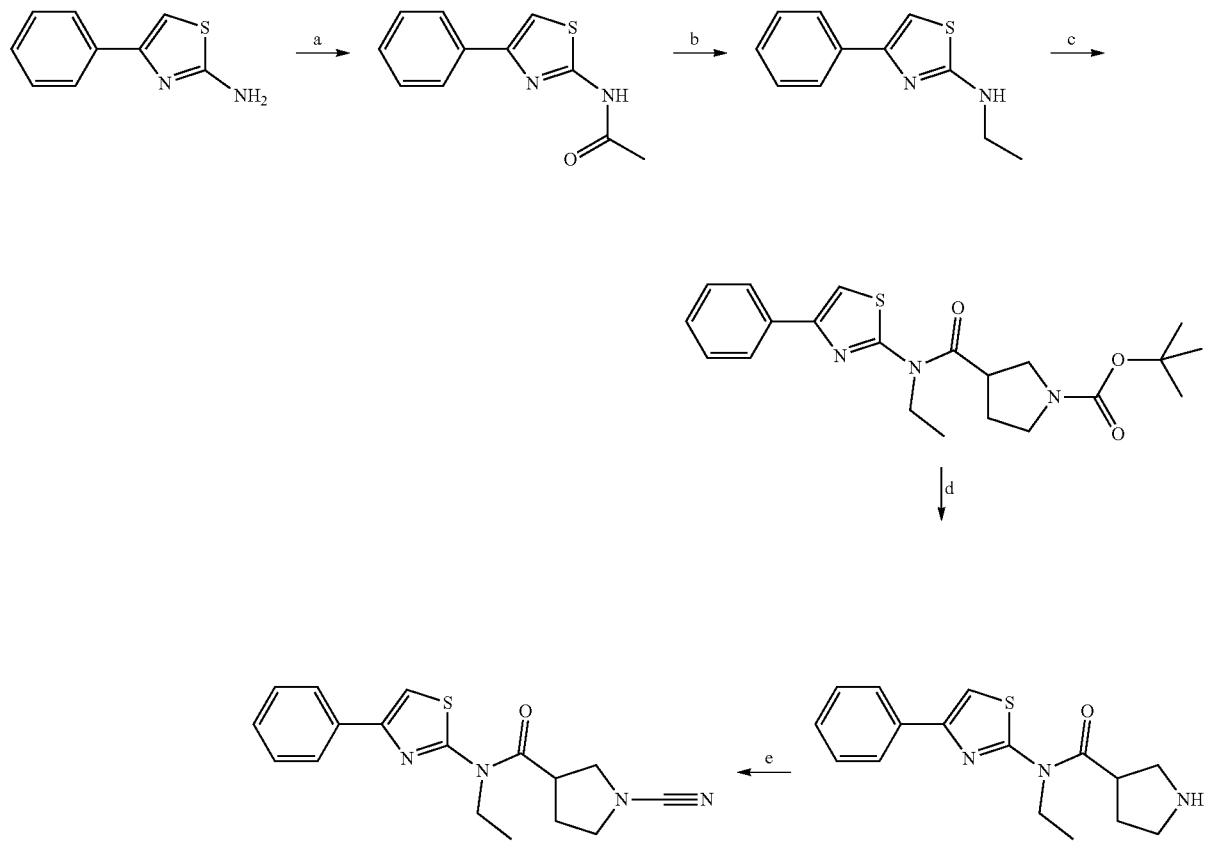

Reagents and conditions: a) acetyl chloride, TEA, THF, 0° C. to rt, 4 h b) Lithium aluminium hydride, THF, 0° C. to 60° C., 3 h c) 1-BOC-pyrrolidine-3-carboxylic acid, EDC•HCl, HOBT, DCM, rt, 6 h d) TFA, DCM, rt, 1-2 h e) cyanogen bromide, K$_2$CO$_3$, DCM, rt 1-2 h.

General Scheme 2

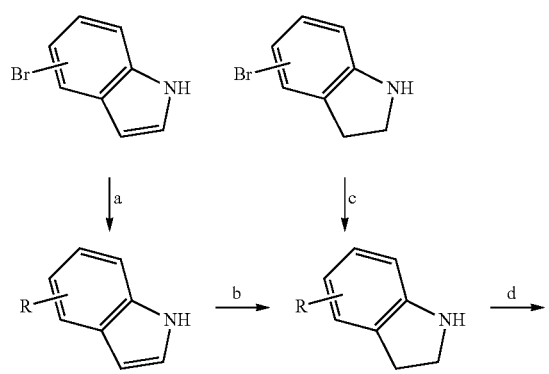

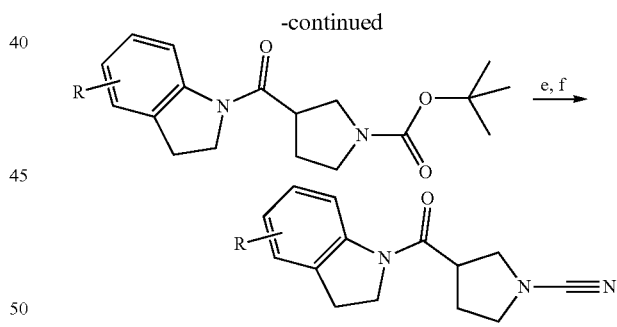

Reagents and conditions: a) boronic acid, PdCl$_2$[P(o-Tol)$_3$]$_2$, K$_2$CO$_3$, dioxane, water, 90° C., 16 h b) AcOH, NaCNBH$_3$, -15° C. to rt, 1 h c) boronic acid, Pd(PPh$_3$)$_4$, Na$_2$CO$_3$, ethanol, toluene, water, 90° C., 16 h d) 1-BOC-pyrrolidine-3-carboxylic acid, POCl$_3$, pyridine, -15° C. to rt, 0.5 h OR 1-BOC-pyrrolidine-3-carboxylic acid, HBTU, DIPEA, DCM, rt 4 h e) TFA, DCM, rt, 1-2 h f) cyanogen bromide, K$_2$CO$_3$, THF, rt 1 h.

General Scheme 3

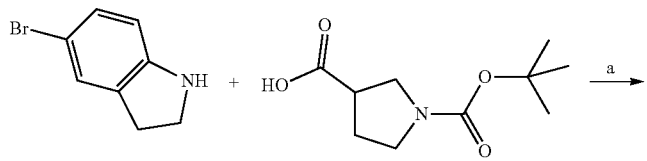

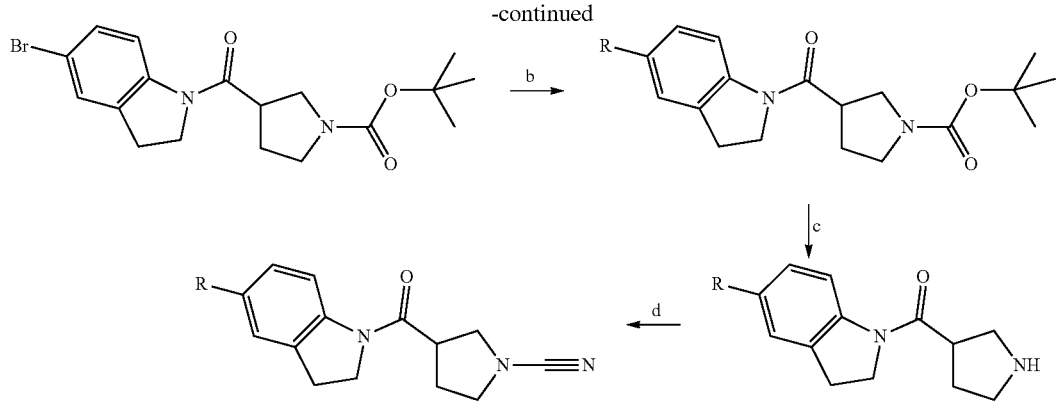

Reagents and conditions: a) 1-BOC-3-fluoropyrrolidine-3-carboxylic acid, T3P, TEA, DCM, 3 h b) boronic acid, Pd(PPh3)4, Cs2CO3, dioxane, water, 100° C., 16 h c) HCl/EtOAc, rt, 2 h d) cyanogen bromide, NaHCO3, EtOH, rt, 16 h General scheme 4

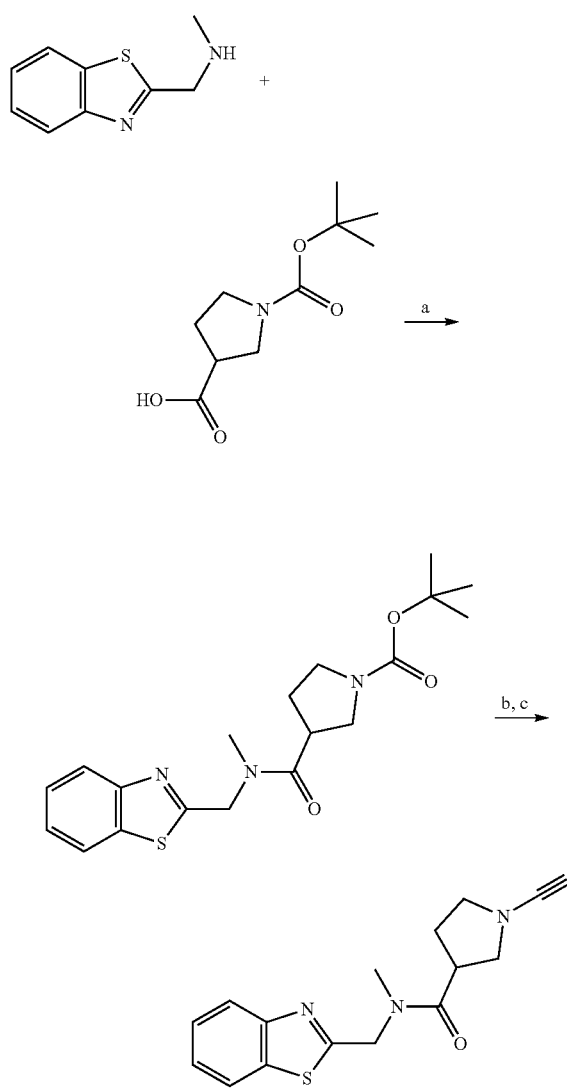

Reagents and conditions: a) HATU, DIPEA, DCM, rt 16 h b) HCl/EtOAc, rt, 2 h c) cyanogen bromide, NaHCO3, EtOH, rt, 16 h Example 1 1-Cyano-N-ethyl-N-(4-phenylthiazol-2-yl)pyrrolidine-3-carboxamide Synthesis According to General Scheme 1

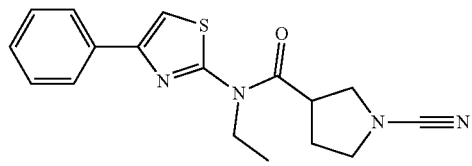 [SMILES: CCN(C(=O)C1CCN(C#N)C1)c1nc(-c2ccccc2)cs1]

Step a.

To a solution of 4-phenylthiazol-2-amine (CAS Number 2010-06-2; 5.00 g, 28.4 mmol) in THF (50 ml) was added TEA (8.3 ml, 59.9 mmol) at 0° C. Acetyl chloride (4.67 g, 59.6 mmol) was added dropwise to the reaction mixture at 0° C. The reaction was stirred at rt for 4 h. The resulting mixture was poured into water (50 ml) and extracted with EtOAc (3×150 ml). The combined organic layer was dried over Na$_2$SO$_4$, filtered and concentrated under reduced pressure. The residue was purified by column chromatography (25% EtOAc in hexane) yielding N-(4-phenylthiazol-2-yl)acetamide (3.00 g, 13.7 mmol). LCMS: Method C, 2.05, MS: ES+219.38; $^1$H NMR (400 MHz, DMSO-d6) δ ppm 12.27 (s, 1H), 7.89 (d, J=7.6 Hz, 2H), 7.61 (s, 1H), 7.43 (t, J=7.6 Hz, 2H), 7.32-7.34 (m, 1H), 2.16 (s, 3H).

Step b.

A solution of N-(4-phenylthiazol-2-yl)acetamide (2.00 g, 9.17 mmol) in THF (20 ml) was cooled at 0° C. A solution of lithium aluminium hydride in THF (1M, 18.3 ml, 18.3 mmol) was added dropwise to the reaction mixture at 0° C. The reaction mixture was heated at 60° C. for 3 h. The resulting mixture was cooled to 0° C. and basified by 1M NaOH solution (20 ml) and extracted with EtOAc (3×50 ml). The combined organic layer was dried over Na$_2$SO$_4$, filtered and concentrated under reduced pressure. The residue was purified by column chromatography (10% EtOAc in hexane) yielding N-ethyl-4-phenylthiazol-2-amine (1.500 g, 7.35 mmol). LCMS: Method C, 2.03, MS: ES+205.38; $^1$H NMR (400 MHz, DMSO-d6) δ ppm 7.81-7.84 (m, 2H), 7.63 (t, J=5.2 Hz, 1H), 7.37 (t, J=7.2 Hz, 2H), 7.26-7.28 (m, 1H), 7.04 (s, 1H), 3.27-3.33 (m, 2H), 1.20 (t, J=6.8 Hz, 3H).

Step c.

To a solution of N-ethyl-4-phenylthiazol-2-amine (0.500 g, 2.45 mmol) in DCM (5 ml) was added 1-(tert-butoxycarbonyl) pyrrolidine-3-carboxylic acid (CAS Number 59378-75-5; 0.526 g, 2.44 mmol) at rt. EDC.HCl (0.704 g, 3.67 mmol) and HOBt (0.374 g, 2.44 mmol) were added to the reaction mixture at rt and stirred for 6 h. The resulting reaction mixture was poured into water (50 ml) and extracted with EtOAc (3×50 ml). The combined organic layer was dried over Na₂SO₄, filtered and concentrated under reduced pressure. The resulting residue was purified by column chromatography (12% EtOAc in hexane) yielding tert-butyl 3-(ethyl(4-phenylthiazol-2-yl)carbamoyl)pyrrolidine-1-carboxylate (0.400 g, 0.997 mmol). LCMS: Method C, 2.83, MS: ES+402.53; $^1$H NMR (400 MHz, DMSO-d6) δ ppm 7.93-7.96 (m, 2H), 7.70 (s, 1H), 7.44 (t, J=7.6 Hz, 2H), 7.31-7.35 (m, 1H), 4.32-4.43 (m, 2H), 3.60-3.71 (m, 2H), 3.38-3.50 (m, 3H), 2.21-2.23 (m, 1H), 2.04-2.10 (m, 1H), 1.36-1.39 (m, 12H).

Step d.

To a solution of tert-butyl 3-(ethyl(4-phenylthiazol-2-yl)carbamoyl)pyrrolidine-1-carboxylate (0.400 g, 0.997 mmol) in DCM (4 ml) was added TFA (0.76 ml) at 0° C. The reaction mixture was stirred at rt for 3 h. The resulting reaction mixture was evaporated under reduced pressure. The obtained residue was washed with pentane (2×5 ml) yielding N-ethyl-N-(4-phenylthiazol-2-yl)pyrrolidine-3-carboxamide TFA salt (0.260 g, quantitative). This material was used directly for the next step without further purification. LCMS: Method C, 1.90 min, MS: ES+302.43.

Step e.

To a solution of N-ethyl-N-(4-phenylthiazol-2-yl)pyrrolidine-3-carboxamide TFA salt (0.260 g, 0.863 mmol) in DCM (3 ml) was added K₂CO₃ (0.231 g, 1.673 mmol) at −40° C. Cyanogen bromide (0.177 g, 1.67 mmol) was added to the reaction mixture at −40° C. The resulting reaction mixture was then stirred at 0° C. for 5 h and then filtered through celite bed, washed with DCM (2×5 ml) and the combined filtrate was washed with water (2×2 ml). The combined organic phase was dried over Na₂SO₄, filtered and concentrated under reduced pressure. The resulting residue was purified by column chromatography (30% EtOAc in hexane) yielding the title compound (0.070 g, 0.214 mmol). LCMS: Method C, 2.42 min, MS: ES+327.43; $^1$H NMR (400 MHz, DMSO-d6) δ ppm 7.95 (d, J=7.6 Hz, 2H), 7.72 (s, 1H), 7.44 (t, J=7.6 Hz, 2H), 7.31-7.33 (m, 1H), 4.30-4.41 (m, 2H), 3.69-3.77 (m, 2H), 3.59-3.63 (m, 1H), 3.47-3.51 (m, 2H), 2.27-2.30 (m, 1H), 2.07-2.12 (m, 1H), 1.38 (t, J=6.4 Hz, 3H).

Example 2 1-Cyano-N-ethyl-N-(5-phenylthiazol-2-yl)pyrrolidine-3

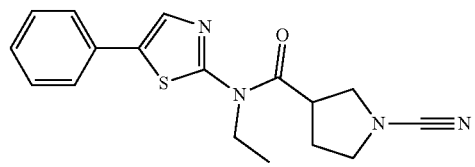 [SMILES: CCN(C(=O)C1CCN(C#N)C1)c1ncc(-c2ccccc2)s1]

The title compound was synthesised using a procedure similar to that described for Example 1. LCMS: Method C, 2.33 min, MS: ES+327.43; $^1$H NMR (400 MHz, CDCl₃) δ ppm 7.72 (s, 1H), 7.58 (d, J=7.6 Hz, 2H), 7.40-7.44 (m, 2H), 7.33-7.35 (m, 1H), 4.30-4.37 (m, 2H), 3.70-3.79 (m, 3H), 3.49-3.57 (m, 2H), 2.33 (s, 2H), 1.21-1.36 (m, 3H).

Example 3 (S)-1-Cyano-N-methyl-N-(5-phenylthiazol-2-yl)pyrrolidine-3-carboxamide Synthesis According to General Scheme 1

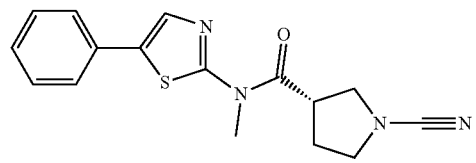 [SMILES: CN(C(=O)[C@H]1CCN(C#N)C1)c1ncc(-c2ccccc2)s1]

Step a.

A mixture of 2-amino-5-phenylthiazole (CAS Number 39136-63-5; 1.0 g, 5.68 mmol) and sodium formate (0.39 g, 5.68 mmol) in THF (5 ml) was heated to 45° C. Acetic anhydride (0.87 g, 8.52 mmol) was added and the reaction mixture was stirred at 45° C. for 1 h. The resulting mixture was cooled to rt, poured into saturated NaHCO₃ solution (100 ml) and extracted with EtOAc (3×50 ml). The combined organic phase was separated, dried over Na₂SO₄, filtered and concentrated under reduced pressure yielding N-(5-phenylthiazol-2-yl)formamide (1.0 g, 4.90 mmol). This material was used for the next step without further purification. LCMS: Method C, 1.94 min, MS: ES−203.28.

Steps b-e.

The title compound was synthesised from the intermediate above using a procedure similar to that described for Example 1, steps b-e. LCMS: Method A, 4.54 min, MS: ES+313.10; $^1$H NMR (400 MHz, DMSO-d6) δ ppm 7.96 (s, 1H), 7.63 (d, J=7.2 Hz, 2H), 7.43 (t, J=8.0 Hz, 2H), 7.32 (t, J=7.2 Hz, 1H), 3.80-3.85 (m, 1H), 3.72 (s, 3H), 3.62-3.67 (m, 2H), 3.45-3.49 (m, 2H), 2.23-2.28 (m, 1H), 2.09-2.15 (m, 1H).

Example 4 (S)-1-Cyano-N-methyl-N-(4-phenylpyridin-2-yl)pyrrolidine-3-carboxamide

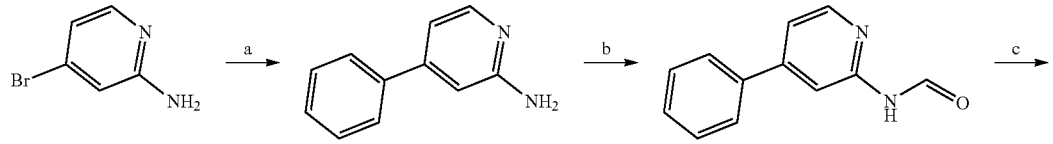

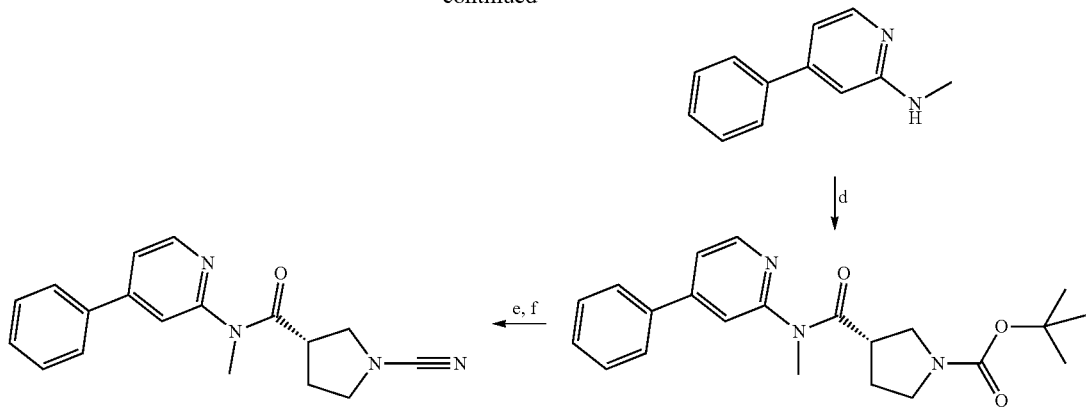

Step a.

To a stirred solution of 2-amino-4-bromopyridine (1.0 g, 5.78 mmol) in 1,4-dioxane (2 ml) was added K$_3$PO$_4$ (2.45 g, 11.56 mmol) and 1,1'-bis(di-tert-butylphosphino)ferrocene (0.168 g, 0.29 mmol) at rt. The reaction was purged with nitrogen for 30 min before adding phenylboronic acid (1.05 g, 8.67 mmol) and Pd(OAc)$_2$ (0.065 g, 0.29 mmol) at rt. The reaction mixture was heated at 80° C. for 16 h. The resulting reaction mixture was cooled to rt, poured into water (50 ml) and extracted with EtOAc (3×25 ml). The combined organic phase was washed with water (25 ml). The organic phase was separated, dried over Na$_2$SO$_4$, filtered and concentrated under reduced pressure. The crude material was purified by flash chromatography (62% EtOAc in hexane) yielding 4-phenylpyridin-2-amine (0.42 g, 2.47 mmol). LCMS: Method C, 1.47 min, MS: ES+171.14; $^1$H NMR (400 MHz, DMSO-d6) δ ppm 7.96 (d, J=5.2 Hz, 1H), 7.63-7.65 (m, 2H), 7.41-7.52 (m, 3H), 6.77 (dd, J=1.6 Hz, 5.2 Hz, 1H), 6.69 (d, J=1.2 Hz, 1H), 6.00 (s, 2H).

Step b.

A mixture of 4-phenylpyridin-2-amine (0.4 g, 2.35 mmol) and ethyl formate (4 ml) was heated at 80° C. for 16 h. The reaction mixture was cooled to rt, diluted with saturated NaHCO$_3$ solution (20 ml) and extracted with DCM (3×15 ml). The combined organic phase was washed with water (20 ml), dried over Na$_2$SO$_4$, filtered and concentrated under reduced pressure. The resulting crude material was purified by flash chromatography (25% EtOAc in hexane) yielding N-(4-phenylpyridin-2-yl)formamide (0.313 g, 1.58 mmol). LCMS: Method C, 1.79 min, MS: ES+199.14; $^1$H NMR (400 MHz, DMSO-d6) δ ppm 10.74 (s, 1H), 9.34 (d, J=10.8 Hz, 1H), 8.39 (s, 1H), 7.72-7.45 (m, 2H), 7.48-7.57 (m, 3H), 7.42-7.45 (m, 1H), 7.21 (s, 1H).

Step c.

To a stirred solution of N-(4-phenylpyridin-2-yl)formamide (0.3 g, 1.51 mmol) in THF (2 ml) was added a solution of lithium aluminium hydride solution in THF (1M, 4.5 ml, 4.5 mmol) dropwise at 0° C. under nitrogen. The reaction mixture was heated at 80° C. for 2 h. The reaction was cooled to rt and quickly poured into sodium sulfate decahydrate. The mixture was filtered and residue was washed with EtOAc (20 ml). The obtained residue was dried under vacuum yielding N-methyl-4-phenylpyridin-2-amine (0.34 g, quantitative). LCMS: Method C, 1.54 min, MS: ES+185.18; $^1$H NMR (400 MHz, DMSO-d6) δ ppm 8.04 (d, J=5.2 Hz, 1H), 7.66 (dd, J=1.2 Hz, 5.2 Hz, 2H), 7.41-7.51 (m, 3H), 6.77 (dd, J=1.6 Hz, 5.2 Hz, 1H), 6.67 (s, 1H), 6.54 (d, J=4.4 Hz, 1H), 2.80 (d, J=4.8 Hz, 3H).

Step d.

A mixture of (S)-1-(tert-butoxycarbonyl)pyrrolidine-3-carboxylic acid (CAS Number 140148-70-5; 0.165 g, 0.768 mmol) and N-methyl-4-phenylpyridin-2-amine (0.113 g, 0.614 mmol) in pyridine (1.6 ml) was stirred at −15° C. under nitrogen for 30 min. POCl$_3$ (0.235 g, 1.535 mmol) was added to the reaction mixture and stirred at −15° C. for 30 min. The resulting reaction mixture was diluted with water (20 ml) and extracted with EtOAc (3×20 ml). The combined organic phase was washed with water (20 ml). The organic phase was separated, dried over Na$_2$SO$_4$, filtered and concentrated under reduced pressure. The resulting crude material was purified by flash chromatography (37% EtOAc in hexane) yielding tert-butyl (S)-3-(methyl(4-phenylpyridin-2-yl)carbamoyl)pyrrolidine-1-carboxylate (0.17 g, 0.446 mmol). LCMS: Method C, 2.19 min, MS: ES+382.1; $^1$H NMR (400 MHz, CDCl$_3$) δ ppm 8.57 (d, J=5.2 Hz, 1H), 7.66-7.68 (m, 2H), 7.49-7.57 (m, 5H), 3.54-3.55 (m, 4H), 3.46 (s, 3H), 3.18-3.24 (m, 2H), 2.03-2.07 (m, 1H), 1.44 (s, 9H).

Steps e, f.

The title compound was synthesised from the intermediate above using a procedure similar to that described for Example 1, steps d, e. LCMS: Method B, 3.62 min, MS: ES+307.5; $^1$H NMR (400 MHz, CDCl$_3$) δ ppm 8.56 (dd, J=0.4 Hz, 5.2 Hz, 1H), 7.65-7.68 (m, 2H), 7.50-7.58 (m, 4H), 7.44 (s, 1H), 3.53-3.69 (m, 3H), 3.43 (s, 3H), 3.35 (q, J=8.8 Hz, 1H), 3.21-3.24 (m, 1H), 2.25-2.35 (m, 1H), 2.03-2.07 (m, 1H).

Example 5 (S)-1-Cyano-N-methyl-N-(6-phenylpyridin-2-yl)pyrrolidine-3-carboxamide

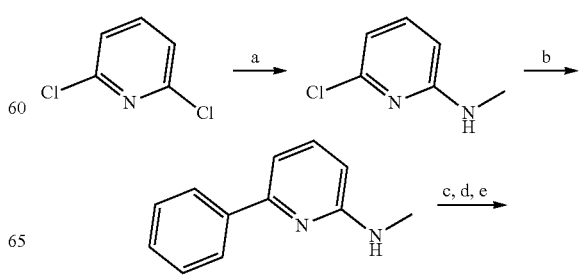

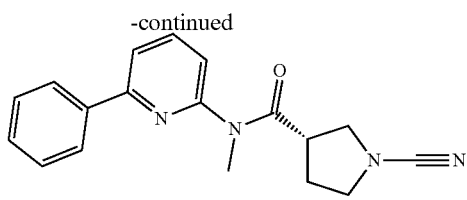

Step a.

To a stirred solution of 2,6-dichloropyridine (1.0 g, 6.76 mmol) in methylamine (40% in water) (1.3 ml) was added NaOH (0.54 g, 13.5 mmol) at rt. The reaction mixture was heated at 80° C. for 16 h. The reaction mixture was cooled to rt, poured into cold water (20 ml). The obtained precipitates were collected by filtration, washed with water (15 ml) and dried under vacuum yielding 6-chloro-N-methylpyridin-2-amine (0.399 g, 2.80 mmol). This material was used for the next step without further purification. LCMS: Method C, 1.82 min, MS: ES+143.03; $^1$H NMR (400 MHz, DMSO-d6) δ ppm 7.38 (dd, J=7.6 Hz, 8.0 Hz, 1H), 6.90 (d, J=4.0 Hz, 1H), 6.48 (d, J=7.6 Hz, 1H), 6.37 (d, J=8.4 Hz, 1H), 2.73 (d, J=4.8 Hz, 3H).

Step b.

To a stirred solution of 6-chloro-N-methylpyridin-2-amine (0.3 g, 2.10 mmol) in toluene:EtOH:water (1:1:1; 3 ml) was added Cs$_2$CO$_3$ (1.37 g, 4.21 mmol) and phenylboronic acid (0.385 g, 3.16 mmol) at rt. The reaction mixture was degassed for 30 min before adding Pd(PPh$_3$)$_4$ (0.121 g, 0.105 mmol) at rt. The reaction mixture was heated at 120° C. for 16 h. The resulting mixture was cooled to rt, diluted with water (20 ml) and extracted with EtOAc (3×25 ml). The combined organic phase was washed with water (20 ml). The organic phase was separated, dried over Na$_2$SO$_4$, filtered and concentrated under reduced pressure. The resulting crude material was purified by flash chromatography (3-7% EtOAc in hexane) yielding N-methyl-6-phenylpyridin-2-amine (0.308 g, 1.67 mmol). LCMS: Method C, 1.48 min, MS: ES+185.14; $^1$H NMR (400 MHz, CDCl$_3$) δ ppm 7.97-8.02 (m, 2H), 7.55 (t, J=8.0 Hz, 1H), 7.44-7.52 (m, 2H), 7.37-7.41 (m, 1H), 7.06 (d, J=7.6 Hz, 1H), 6.39 (d, J=8.4 Hz, 1H), 3.00 (s, 3H).

Steps c, d, e.

The title compound was synthesised from the intermediate above using a procedure similar to that described for Example 4, steps d, e, f. LCMS: Method B, 3.87 min, MS: ES+307.26; $^1$H NMR (400 MHz, CDCl$_3$) δ ppm 7.99-8.01 (m, 2H), 7.90 (t, J=8.0 Hz, 1H), 7.74 (d, J=7.6 Hz, 1H), 7.46-7.55 (m, 3H), 7.16 (d, J=7.6 Hz, 1H), 3.63-3.71 (m, 1H), 3.57-3.63 (m, 1H), 3.47-3.51 (m, 1H), 3.44 (s, 3H), 3.27-3.53 (m, 2H), 2.25-2.32 (m, 1H), 2.01-2.05 (m, 1H).

Example 6 1-Cyano-N-isopropyl-N-(5-(pyridin-4-yl)thiazol-2-yl)pyrrolidine-3-carboxamide

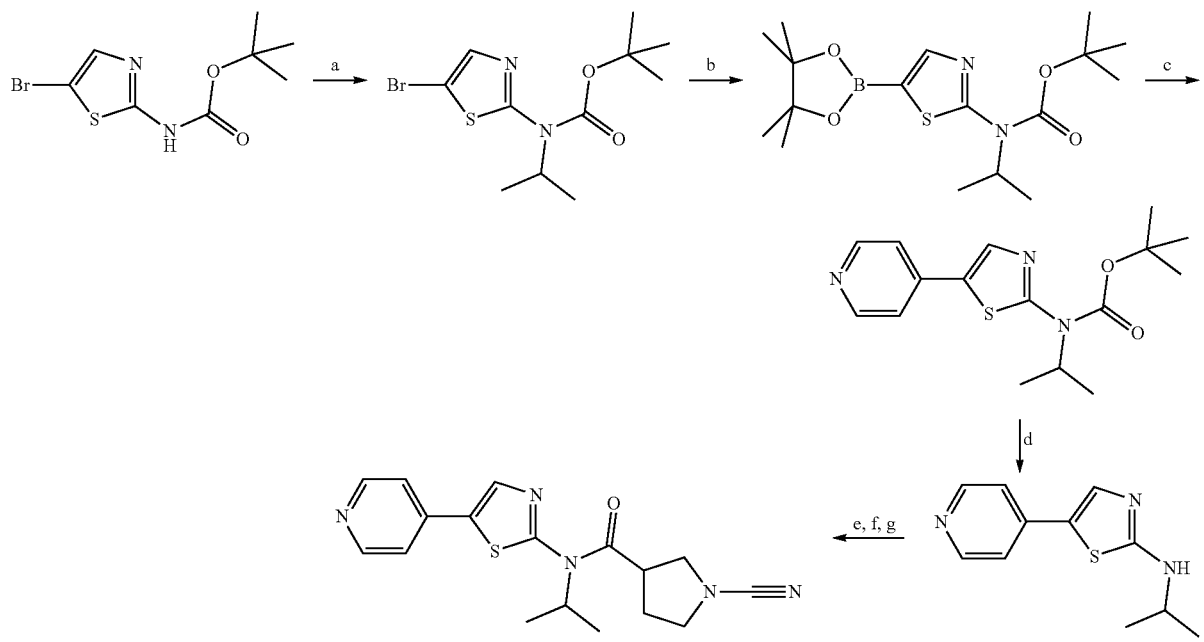

Step a.

A mixture of tert-butyl (5-bromothiazol-2-yl)carbamate (5.0 g, 18.0 mmol), PPh$_3$ (10.37 g, 39.57 mmol) and IPA (3.2 g, 54.0 mmol) in THF (50 ml) was cooled at 0° C. under N$_2$ atmosphere. DIAD (7.70 ml, 39.6 mmol) was added dropwise to the reaction mixture at 0° C. The reaction mixture was stirred at rt for 10 min and then heated to 75° C. for 3 h. The resulting reaction mixture cooled to rt and was concentrated under reduced pressure. The residue was purified by column chromatography (2-5% EtOAc in hexane) yielding tert-butyl (5-bromothiazol-2-yl)(isopropyl)carbamate (5.0 g, 15.62 mmol). LCMS: Method C, 3.11 min, MS: ES+321.1, 323.1 (M+2); $^1$H NMR (400 MHz, CDCl$_3$) δ ppm 7.36 (s, 1, 1H), 5.26-5.33 (m, 1H), 1.61 (s, 9H), 1.45 (d, J=7.2 Hz, 6H).

Step b.

A solution of tert-butyl (5-bromothiazol-2-yl)(isopropyl)carbamate (1.00 g, 3.12 mmol) in dry THF (20 ml) was cooled at −78° C. and treated dropwise with 2.4M n-BuLi in Hexane (1.3 ml, 3.12 mmol) at −78° C. and stirred for 10 min before adding 4,4,5,5-tetramethyl-1,3,2-dioxaborolane (0.54 ml, 3.75 mmol). The reaction mixture was stirred at −78° C. for 30 min. The resulting reaction mixture was warmed to rt. The resulting mixture was then combined with one other batch prepared by an identical method on the same scale. The obtained mixture was quenched by saturated NH₄Cl solution (100 ml) and extracted with EtOAc (2×100 ml). The combined organic phase was dried over Na₂SO₄, filtered and concentrated under reduced pressure yielding tert-butyl isopropyl (5-(4,4,5,5-tetramethyl-1,3,2-dioxaborolan-2-yl)thiazol-2-yl)carbamate (2.4 g, quantitative). This material was directly used for the next step without any purification.

Step c.

A suspension of 4-bromopyridine hydrochloride (0.25 g, 1.28 mmol), tert-butyl isopropyl (5-(4,4,5,5-tetramethyl-1,3,2-dioxaborolan-2-yl)thiazol-2-yl)carbamate (0.52 g, 1.41 mmol) and Na₂CO₃ (0.30 g, 2.83 mmol) in toluene:water (9:1) (15 ml) was degassed with nitrogen for 15 min at rt.

Tetrakis(triphenylphosphine)palladium (0.11 g, 0.128 mmol) was added to the reaction mixture at rt. The reaction mixture was heated at 110° C. for 1 h. The resulting mixture was cooled to rt and combined with three other batches prepared by an identical method on the same scale and poured into water (200 ml). The obtained mixture was extracted with EtOAc (2×200 ml). The combined organic phase was dried over Na₂SO₄, filtered and concentrated under reduced pressure. The resulting residue was purified by flash chromatography (42% EtOAc in hexane) yielding tert-butyl isopropyl(5-(pyridin-4-yl)thiazol-2-yl)carbamate (0.85 g, 2.66 mmol). LCMS: Method C, 2.11 min, MS: ES+320.20; ¹H NMR (400 MHz, DMSO-d6) 8.55 (d, J=6.0 Hz, 2H), 8.16 (s, 1H), 7.60 (d, J=6.4 Hz, 2H), 5.30-5.33 (m, 1H), 1.56 (s, 9H), 1.42 (d, J=6.8 Hz, 6H).

Step d.

To a solution of tert-butyl isopropyl(5-(pyridin-4-yl)thiazol-2-yl)carbamate (0.85 g, 2.66 mmol) in DCM (10 ml) was added TFA (1 ml) at rt. The reaction mixture was stirred at rt for 1 h. The resulting reaction mixture was concentrated under reduced pressure. The residue was triturated with the diethyl ether (20 ml) and dried under vacuum yielding N-isopropyl-5-(pyridin-4-yl)thiazol-2-amine TFA salt (0.70 g, 2.10 mmol). LCMS: Method C, 1.45 min, MS: ES+220.13.

Steps e, f, g.

The title compound was synthesised from the intermediate above using a procedure similar to that described for Example 4, steps d, e, f. LCMS: Method A, 3.79 min, MS: ES+341.92; ¹H NMR (400 MHz, DMSO-d6, 80° C.) δ ppm 8.61-8.62 (m, 2H), 8.32 (s, 1H), 7.64-8.65 (m, 2H), 4.80-4.86 (m, 1H), 3.54-3.56 (m, 2H), 3.35-3.47 (m, 3H), 2.05-2.14 (m, 2H), 1.36-1.42 (m, 6H).

Example 7 1-Cyano-N-isopropyl-N-(4-phenylthiazol-2-yl)pyrrolidine-3-carboxamide

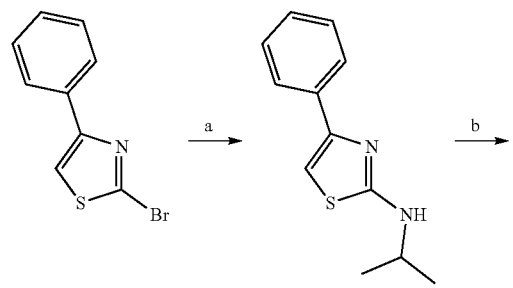

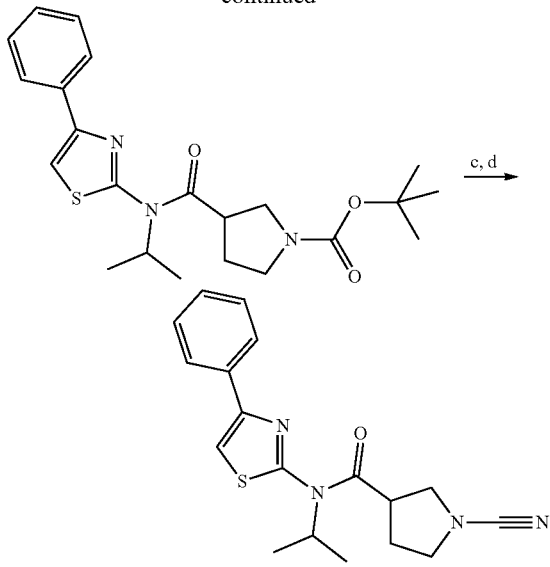

Step a.

A suspension of 2-bromo-4-phenylthiazole (0.5 g, 2.09 mmol), IPA (1.0 ml, 12.55 mmol) and K₂CO₃ (0.87 g, 6.28 mmol) in DMSO (12 ml) was heated in a microwave at 150° C. for 2 h. The resulting mixture was cooled to rt and was combined with another two batches prepared by an identical method on the same scale. The resulting reaction mixture was poured into water (50 ml) and extracted with hexane (3×50 ml). The combined organic phase was dried over Na₂SO₄, filtered and concentrated under reduced pressure. The residue was purified by flash chromatography (3% EtOAc in hexane) yielding N-isopropyl-4-phenylthiazol-2-amine (0.370 g, 1.70 mmol). LCMS: Method C, 2.08 min, MS: ES+219.18. ¹H NMR (400 MHz, DMSO-d₆) δ ppm 7.81-7.83 (m, 2H), 7.56 (d, J=7.2 Hz, 1H), 7.37 (t, J=7.6 Hz, 2H), 7.25 (t, J=7.2 Hz, 1H), 7.03 (s, 1H), 3.78-3.83 (m, 1H), 1.21 (d, J=6.4 Hz, 6H).

Step b.

A suspension of N-isopropyl-4-phenylthiazol-2-amine (0.29 g, 1.33 mmol), 1-Boc-pyrrolidine-3-carboxylic acid (CAS Number 59378-75-5; 0.58 g, 2.66 mmol) and DCC (0.69 g, 3.32 mmol) in DMF (0.05 ml) was heated in a microwave at 120° C. for 1 h. The resulting reaction mixture was cooled to rt.

The resulting mixture was diluted with water (50 ml) and extracted with EtOAc (2×50 ml). The combined organic phase was dried over Na₂SO₄, filtered and concentrated under reduced pressure. The resulting residue was purified by flash chromatography (5% EtOAc in hexane) yielding tert-butyl 3-(isopropyl(4-phenylthiazol-2-yl)carbamoyl)pyrrolidine-1-carboxylate (0.204 g, 0.491 mmol). LCMS: Method C, 2.92 min, MS: ES+416.1.

Steps c, d.

The title compound was synthesised from the intermediate above using a procedure similar to that described for Example 1, steps d, e. LCMS: Method A, 5.01 min, MS: ES+340.93. ¹H NMR (400 MHz, DMSO-d6, 80° C.) δ ppm 8.00 (s, 1H), 7.93-7.95 (m, 2H), 7.46 (t, J=7.6 Hz, 2H), 7.36 (t, J=7.2 Hz, 1H), 4.79-4.86 (m, 1H), 3.44-3.57 (m, 3H), 3.32-3.42 (m, 2H), 2.06-2.11 (m, 2H), 1.36 (s, 6H).

Example 8 1-Cyano-3-fluoro-N-methyl-N-(5-phenylthiazol-2-yl)pyrrolidine-3-carboxamide

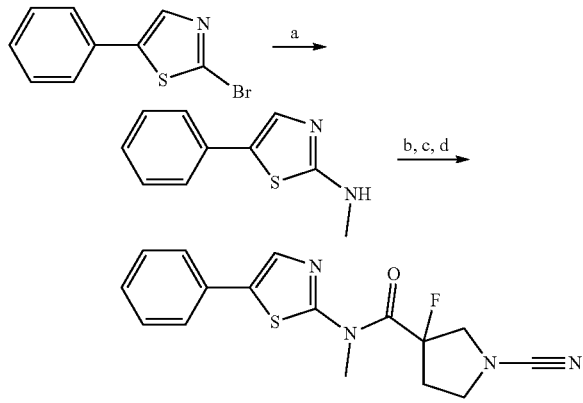

Step a.

A mixture of 2-bromo-5-phenylthiazole (1.4 g, 5.83 mmol) and methylamine (33% in EtOH) (14 ml) was heated at 80° C. for 16 h. The reaction mixture was cooled to rt and concentrated under vacuum. The resulting crude material was triturated with n-pentane (2×5 ml) and dried under high vacuum to yield N-methyl-5-phenylthiazol-2-amine (1.4 g, quantitative). LCMS: Method C, 1.72 min, MS: ES+191.4; $^1$H NMR (400 MHz, DMSO-d6) δ ppm 7.71 (d, J=4.8 Hz, 1H), 7.49 (s, 1H), 7.42 (dd, J=0.8 Hz, 8 Hz, 2H), 7.33 (t, J=8.0 Hz, 2H), 7.16-7.19 (m, 1H), 2.84 (d, J=4.8 Hz, 3H).

Steps b, c, d.

The title compound was synthesised from the intermediate above using a procedure similar to that described for Example 4, steps d, e, f. LCMS: Method B, 4.52 min, MS: ES+331.29; $^1$H NMR (400 MHz, DMSO-d6) δ ppm 8.04 (s, 1H), 7.66 (dd, J=1.2 Hz, 8.4 Hz, 2H), 7.45 (t, J=8.0 Hz, 2H), 7.35 (t, J=7.6 Hz, 1H), 4.05-4.21 (m, 2H), 3.76 (d, J=3.6 Hz, 3H), 3.69-3.74 (m, 1H), 3.59-3.66 (m, 1H), 2.68-2.78 (m, 1H), 2.64-2.67 (m, 1H).

Example 9 N-(Benzo[d]thiazol-2-yl)-1-cyano-3-fluoro-N-methylpyrrolidine-3-carboxamide

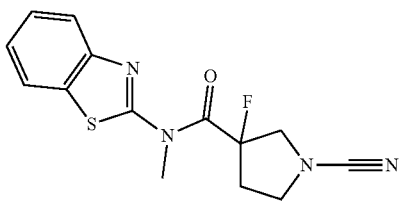 [SMILES: CN(C(=O)C1(F)CCN(C#N)C1)c1nc2ccccc2s1]

The title compound was synthesised using a procedure similar to that described for Example 8. LCMS: Method A, 4.62 min, MS: ES+304.9; $^1$H NMR (400 MHz, DMSO-d$_6$) δ ppm 8.05 (d, J=7.6 Hz, 1H), 7.89 (d, J=8.0 Hz, 1H), 7.48-7.52 (m, 1H), 7.37-7.41 (m, 1H), 4.07-4.24 (m, 2H), 3.84 (d, J=3.6 Hz, 3H), 3.70-3.78 (m, 1H), 3.60-3.66 (m, 1H), 2.61-2.81 (m, 2H).

Example 10 (S)-3-(4-Phenylindoline-1-carbonyl)pyrrolidine-1-carbonitrile

Synthesis According to General Scheme 2, Steps a, b, d, e, f.

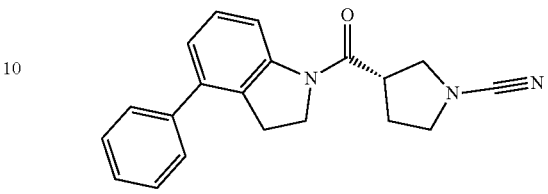

Step a.

To a stirred solution of 4-bromoindole (0.3 g, 1.53 mmol) in 1,4-dioxane:water (3:1; 8 ml) was added K$_2$CO$_3$ (0.634 g, 4.59 mmol) at rt. The reaction mixture was degassed for 15 min before adding phenylboronic acid (0.223 g, 1.84 mmol) and dichlorobis(tri-o-tolylphosphine)palladium(II) (0.06 g, 0.076 mmol) at rt. The reaction mixture was heated at 95° C. for 4 h. The resulting mixture was cooled to rt, poured into water (10 ml) and extracted with EtOAc (3×20 ml). The combined organic phase was washed with brine (20 ml), dried over Na$_2$SO$_4$, filtered and concentrated under reduced pressure. The resulting crude material was purified by flash chromatography (5% EtOAc in hexane) yielding 4-phenyl-1H-indole (0.25 g, 1.29 mmol). LCMS: Method C, 2.33 min, MS: ES+194.1; $^1$H NMR (400 MHz, DMSO-d6) δ ppm 11.28 (s, 1H), 7.67 (dd, J=1.2, 8.4 Hz, 2H), 7.501 (t, J=7.6 Hz, 2H), 7.36-7.43 (m, 3H), 7.19 (t, J=8.0 Hz, 1H), 7.08 (dd, J=0.4 Hz, 7.2 Hz, 1H), 6.55 (t, J=2.0 Hz, 1H).

Step b.

To a stirred solution of 4-phenyl-1H-indole (0.25 g, 1.29 mmol) in acetic acid (3 ml) was added NaCNBH$_3$ (0.089 g, 1.42 mmol) at rt. The reaction mixture was stirred at rt for 1 h. The resulting mixture was basified with saturated NaHCO$_3$ solution and extracted with EtOAc (3×20 ml). The combined organic phase was washed with brine (20 ml), dried over Na$_2$SO$_4$, filtered and concentrated under reduced pressure yielding 4-phenylindoline (0.37 g, quantitative). This material was used for the next step without further purification. LCMS: Method C, 1.78 min, MS: ES+195.8; $^1$H NMR (400 MHz, DMSO-d6) δ ppm 7.44-7.51 (m, 4H), 7.31-7.35 (m, 1H), 7.01 (t, J=7.6 Hz, 1H), 6.59 (d, J=7.2 Hz, 1H), 6.51 (d, J=7.6 Hz, 1H), 5.60 (s, 1H), 3.39 (t, J=8.4 Hz, 2H), 2.98 (t, J=8.4 Hz, 2H).

Step d.

To a stirred solution of (S)-1-(tert-butoxycarbonyl)pyrrolidine-3-carboxylic acid (CAS Number 140148-70-5; 0.462 g, 2.15 mmol) in DCM (5 ml) was added HBTU (1.018 g, 2.69 mmol) and DIPEA (0.463 g, 3.58 mmol) at rt. The reaction mixture was stirred at rt for 15 min before adding 4-phenylindoline (0.35 g, 1.79 mmol) at rt. The reaction mixture was stirred at rt for 4 h. The resulting reaction mixture was poured into saturated solution of NaHCO$_3$ solution (10 ml) and extracted with EtOAc (3×20 ml). The combined organic phase was washed with brine (20 ml), dried over Na$_2$SO$_4$, filtered and concentrated under reduced pressure. The resulting crude material was purified by flash chromatography (20% EtOAc in hexane) yielding tert-butyl (S)-3-(4-phenylindoline-1-carbonyl)pyrrolidine-1-carboxylate (0.3 g, 0.76 mmol). This material was used for the next step without further purification. LCMS: Method C, 2.64 min, MS: ES+393.33; $^1$H NMR (400 MHz, DMSO-d6) δ ppm 8.14 (d, J=8.0 Hz, 1H), 7.47 (d, J=4.4 Hz, 4H), 7.38-7.41 (m, 1H), 7.28 (t, J=7.6 Hz, 1H), 7.06 (d, J=7.6 Hz, 1H), 4.18 (t, J=8.4 Hz, 2H), 3.52-3.54 (m, 1H), 3.39-3.44 (m, 3H), 3.19-3.34 (m, 3H), 2.16-2.18 (m, 1H), 2.01-2.10 (m, 1H), 1.42 (s, 9H).

Steps e, f.

The title compound was synthesised from the intermediate above using a procedure similar to that described for Example 1, steps d, e. LCMS: Method A, 4.83 min, MS: ES+318.03; $^1$H NMR (400 MHz, DMSO-d6) δ ppm 8.15 (d, J=8.0 Hz, 1H), 7.47 (d, J=4.4 Hz, 4H), 7.37-7.42 (m, 1H), 7.29 (t, J=8.0 Hz, 1H), 7.07 (d, J=7.2 Hz, 1H), 4.17 (t, J=8.8 Hz, 2H), 3.56-3.66 (m, 2H), 3.45-3.49 (m, 3H), 3.21 (t, J=8.0 Hz, 2H), 2.17-2.24 (m, 1H), 2.04-2.10 (m, 1H).

Example 11 (R)-3-(6-Phenylindoline-1-carbonyl)pyrrolidine-1-carbonitrile

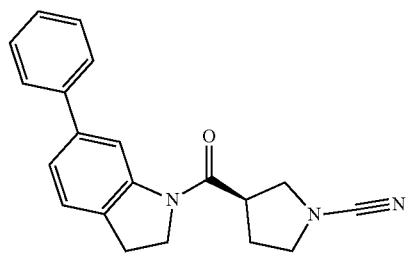 [SMILES: N#CN1CC[C@@H](C(=O)N2CCc3ccc(-c4ccccc4)cc32)C1]

The title compound was synthesised using a procedure similar to that described for Example 10. LCMS: Method A, 4.81 min, MS: ES+317.97; $^1$H NMR (400 MHz, DMSO-d6) δ ppm 8.42 (s, 1H), 7.58-7.60 (m, 2H), 7.46 (t, J=7.6 Hz, 2H), 7.30-7.37 (m 3H), 4.20-4.25 (m, 2H), 3.57-3.66 (m, 2H), 3.43-3.49 (m, 3H), 3.19 (t, J=8.4 Hz, 2H), 2.19-2.24 (m, 1H), 2.05-2.10 (m, 1H).

Example 12 (S)-3-(5-(3-Chlorophenyl)indoline-1-carbonyl)pyrrolidine-1-carbonitrile

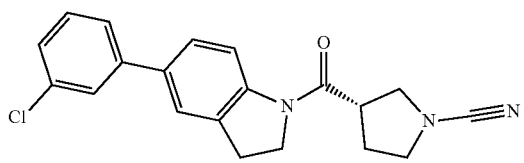 [SMILES: N#CN1CC[C@H](C(=O)N2CCc3cc(-c4cccc(Cl)c4)ccc32)C1]

The title compound was synthesised using a procedure similar to that described for Example 10. LCMS: Method A, 5.25 min, MS: ES+352.01; $^1$H NMR (400 MHz, DMSO-d6) δ ppm 8.15 (d, J=8.4 Hz, 1H), 7.70 (t, J=6.0 Hz, 1H), 7.62-7.63 (m, 2H), 7.53-7.56 (m, 1H), 7.46 (t, J=8.0 Hz, 1H), 7.38 (d, J=8.0 Hz, 1H), 4.23 (t, J=8.8 Hz, 2H), 3.57-3.67 (m, 2H), 3.44-3.49 (m, 3H), 3.23 (t, J=8.4 Hz, 2H), 1.18-2.25 (m, 1H), 2.05-2.12 (m, 1H).

Example 13 (trans)-3-(5-(2-Chlorophenyl)indoline-1-carbonyl)-4-methylpyrrolidine-1-carbonitrile

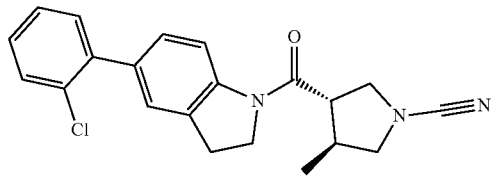 [SMILES: C[C@@H]1CN(C#N)C[C@H]1C(=O)N1CCc2cc(-c3ccccc3Cl)ccc21]

The title compound was synthesised using a procedure similar to that described for Example 10. LCMS: Method B, 4.76 min, MS: ES+383.33 (M+18); $^1$H NMR (400 MHz, DMSO-d6) δ ppm 8.17 (d, J=8.0 Hz, 1H), 7.55-7.57 (m, 1H), 7.38-7.42 (m, 3H), 7.32 (s, 1H), 7.22-7.24 (dd, J=1.6 Hz, 8.0 Hz, 1H), 4.21-4.26 (m, 2H), 3.78-3.82 (m, 1H), 3.58-3.62 (m, 1H), 3.48-3.52 (m, 1H), 3.20-3.24 (m, 2H), 3.07-3.16 (m, 2H), 2.57-2.61 (m, 1H), 1.08 (d, J=6.8 Hz, 3H).

Example 14 3-Fluoro-3-(5-phenylindoline-1-carbonyl)pyrrolidine-1-carbonitrile

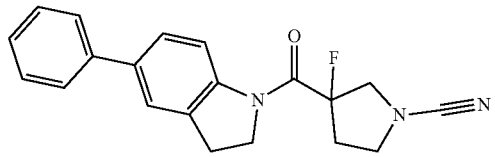 [SMILES: N#CN1CCC(F)(C(=O)N2CCc3cc(-c4ccccc4)ccc32)C1]

The title compound was synthesised using a procedure similar to that described for Example 10. The amide coupling step (step d) was conducted according to the method described for Example 4, step d, using 1-(tert-butoxycarbonyl)-3-fluoropyrrolidine-3-carboxylic acid (CAS Number 1001754-59-1). LCMS: Method B, 4.79 min, MS: ES+336.44; $^1$H NMR (400 MHz, DMSO-d6) δ ppm 8.13 (d, J=8.4 Hz, 1H), 7.65 (t, J=8.4 Hz, 3H), 7.53 (d, J=8.8 Hz, 1H), 7.45 (t, J=7.6 Hz, 2H), 7.34 (t, J=7.2 Hz, 1H), 4.31-4.35 (m, 2H), 4.00-4.11 (m, 2H), 3.69-3.75 (m, 1H), 3.57-3.63 (m, 1H), 3.24 (t, J=8.0 Hz, 2H), 2.65-2.68 (m, 1H), 2.56-2.59 (m, 1H).

Example 15 3-Fluoro-3-(6-phenylindoline-1-carbonyl)pyrrolidine-1-carbonitrile

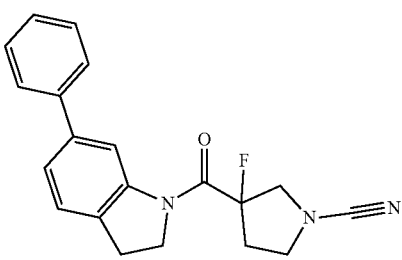 [SMILES: N#CN1CCC(F)(C(=O)N2CCc3ccc(-c4ccccc4)cc32)C1]

The title compound was synthesised using a procedure similar to that described for Example 14. LCMS: Method B, 4.68 min, MS: ES+336.30; $^1$H NMR (400 MHz, DMSO-d6)

δ ppm 8.38 (s, 1H), 7.60 (d, J=7.6 Hz, 2H), 7.47 (t, J=7.6 Hz, 2H), 7.35-7.4 (m, 3H), 4.32-4.36 (m, 2H) 3.97-4.12 (m, 2H), 3.70-3.74 (m, 1H), 3.61 (q, J=7.2 Hz, 1H) 3.21 (t, J=8.4 Hz, 2H), 2.63-2.69 (m, 1H), 2.51-2.60 (m, 1H).

Example 16 3-Fluoro-3-(6-phenyl-2,3-dihydro-1-H-pyrrolo[2,3-b]pyridine-1-carbonyl)pyrrolidine-1-carbonitrile

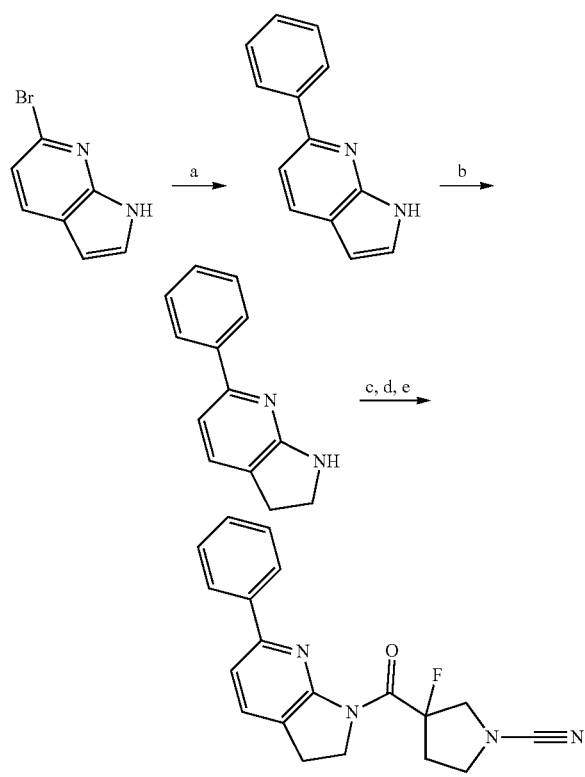

Step a.

A mixture of 6-bromo-1H-pyrrolo[2,3-b]pyridine (CAS Number 143468-13-7; 0.7 g, 3.55 mmol), phenylboronic acid (0.65 g, 5.33 mmol) and K₂CO₃ (1.47 g, 10.66 mmol) in 1,4-dioxane:water (5:2; 14 ml) was stirred at rt. The reaction mixture was degassed for 15 min before adding dichlorobis(tri-o-tolylphosphine)palladium(II) (0.14 g, 0.179 mmol). The reaction mixture was heated at 90° C. for 1 h.

The resulting reaction mixture was cooled to rt, poured into water (30 ml) and extracted with EtOAc (2×30 ml). The combined organic phase was separated, dried over Na₂SO₄, filtered and concentrated under reduced pressure. The resulting crude material was triturated with hexane (2×20 ml) yielding 6-phenyl-1H-pyrrolo[2,3-b]pyridine (0.8 g, quantitative). This material was used for the next step without further purification. LCMS: Method C, 2.13 min, MS: ES+194.7; ¹H NMR (400 MHz, DMSO-d6) δ ppm 11.73 (s, 1H), 8.10 (d, J=7.6 Hz, 2H), 8.03 (d, J=8.0 Hz, 1H), 7.66 (d, J=8.4 Hz, 1H), 7.47-7.50 (m, 3H), 7.37-7.40 (m, 1H), 6.47 (dd, J=2.0 Hz, 3.2 Hz, 1H).

Step b.

A mixture of 6-phenyl-1H-pyrrolo[2,3-b]pyridine (0.8 g, 4.102 mmol), 10% dry Pd/C (0.8 g) and concentrated HCl (0.9 ml) in EtOH (30 ml) was stirred at rt in an autoclave. The autoclave was sealed and the reaction mixture was heated at 80° C. under 60 Psi hydrogen pressure for 16 h. The reaction mixture was cooled to rt, carefully filtered through celite bed and filtrate was evaporated to dryness. The residue was dissolved in water (15 ml), basified using 1M NaOH solution and extracted with EtOAc (3×25 ml). The combined organic phase was washed with saturated NaHCO₃ solution (20 ml) and brine (20 ml). The organic phase was separated, dried over Na₂SO₄, filtered and concentrated under reduced pressure yielding 6-phenyl-2,3-dihydro-1H-pyrrolo[2,3-b]pyridine (0.554 g, 2.83 mmol). This material was used for the next step without further purification. LCMS: Method C, 1.64 min, MS: ES+197.4.

Steps c, d, e.

The title compound was synthesised from the intermediate above using a procedure similar to that described for Example 10, steps d, e, f. LCMS: Method A, 4.71 min, MS: ES+337.00; ¹H NMR (400 MHz, DMSO-d6) δ ppm 7.95 (d, J=7.2 Hz, 2H), 7.79 (d, J=8.0 Hz, 1H), 7.60 (d, J=7.6 Hz, 1H), 7.51 (t, J=8.4 Hz, 2H), 7.42-7.46 (m, 1H), 4.35-4.43 (m, 1H), 4.07-4.18 (m, 3H), 3.60-3.72 (m, 2H), 3.12 (t, J=8.8 Hz, 2H), 2.67-2.85 (m, 2H).

Example 17 (R)-3-(5-Phenylindoline-1-carbonyl)pyrrolidine-1-carbonitrile

Synthesis According to General Scheme 2, Steps c, d, e, f.

Step c.

To a solution of 5-bromoindoline (1.00 g, 5.05 mmol) in toluene:EtOH:water (8:1.5:0.5, 10 ml) was added phenylboronic acid (0.923 g, 7.57 mmol) and Na₂CO₃ (1.60 g, 15.15 mmol). The reaction mixture was degassed for 15 min before addition of Pd(PPh₃)₄ (0.291 g, 0.251 mmol) at rt. The reaction mixture was heated at 90° C. for 16 h. The reaction mixture was poured into water (100 ml) and extracted with EtOAc (3×100 ml). The combined organic phase was dried over Na₂SO₄, filtered and concentrated under reduced pressure. The resulting residue was purified by column chromatography (12% EtOAc in hexane) yielding 5-phenylindoline (0.63 g, 3.23 mmol). LCMS: Method C, 1.93 min, MS: ES+196.23; ¹H NMR (400 MHz, DMSO-d6) δ ppm 7.51-7.54 (m, 2H), 7.35-7.38 (m, 3H), 7.19-7.24 (m, 2H), 6.56 (d, J=8.0 Hz, 1H), 5.64 (s, 1H), 3.44-3.48 (m, 2H), 2.96 (t, J=8.4 Hz, 2H).

Step d.

To a solution of 5-phenylindoline (0.300 g, 1.538 mmol) in THF (15 ml) was added (R)-1-(tert-butoxycarbonyl)pyrrolidine-3-carboxylic acid (CAS Number 72925-16-7; 0.397, 1.84 mmol) at 0° C. T3P (50% solution in EtOAc; 1.46 ml, 2.31 mmol) and TEA (0.42 ml, 3.08 mmol) was added to the reaction mixture at 0° C. The resulting reaction mixture was then stirred at rt for 1 h. The mixture was poured into water (100 ml) and extracted with EtOAc (3×50 ml). The combined organic phase was washed with saturated NaHCO₃ solution (50 ml). The combined organic phase was dried over Na₂SO₄, filtered and concentrated under reduced pressure. The resulting residue was purified by column chromatography (1% MeOH in DCM) yielding tert-butyl (S)-3-(5-phenylindoline-1-carbonyl)-pyrrolidine-1-carboxylate (0.430 g, 1.10 mmol). LCMS: Method C, 2.66 min, MS: ES+393.90; ¹H NMR (400 MHz, DMSO-d6) δ ppm 8.15 (d, J=8.4 Hz, 1H), 7.64 (d, J=7.2 Hz, 2H), 7.56 (s, 1H), 7.42-7.49 (m, 3H), 7.30-7.34 (m, 1H), 4.23 (t, J=8.4 Hz, 2H), 3.53-3.57 (m, 1H), 3.37-3.43 (m, 4H), 3.22 (t, J=8.4 Hz, 2H), 2.15-2.18 (m, 1H), 1.99-2.02 (m, 1H), 1.42 (s, 9H).

Steps e, f.

The title compound were synthesised from the intermediate above using a procedure similar to that described for Example 1, steps d, e. LCMS: Method B, 4.42 min, MS: ES+318.53; ¹H NMR (400 MHz, DMSO-d6) δ ppm 8.15 (d, J=8.0 Hz, 1H), 7.64 (d, J=7.2 Hz, 2H), 7.57 (s, 1H), 7.49 (d, J=8.4 Hz, 1H), 7.44 (t, J=8.0 Hz, 2H), 7.31-7.34 (m, 1H), 4.22 (t, J=8.0 Hz, 2H), 3.57-3.67 (m, 2H), 3.41-3.52 (m, 3H), 3.23 (t, J=8.0 Hz, 2H), 2.18-2.24 (m, 1H), 2.05-2.11 (m, 1H).

Example 18 (S)-3-(5-Phenylindoline-1-carbonyl)pyrrolidine-1-carbonitrile

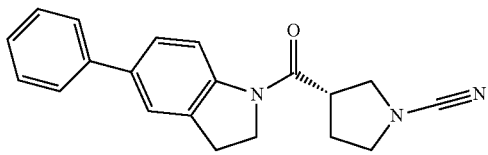 [SMILES: N#CN1CC[C@H](C(=O)N2CCc3cc(-c4ccccc4)ccc32)C1]

The title compound was synthesised using a procedure similar to that described for Example 17. LCMS: Method B, 4.42 min, MS: ES+318.53; ¹H NMR (400 MHz, DMSO-d6) δ ppm 8.15 (d, J=8.0 Hz, 1H), 7.64 (d, J=7.2 Hz, 2H), 7.57 (s, 1H), 7.49 (d, J=8.4 Hz, 1H), 7.44 (t, J=8.0 Hz, 2H), 7.31-7.34 (m, 1H), 4.22 (t, J=8.0 Hz, 2H), 3.57-3.67 (m, 2H), 3.41-3.52 (m, 3H), 3.23 (t, J=8.0 Hz, 2H), 2.18-2.24 (m, 1H), 2.05-2.11 (m, 1H).

Example 19 (3S,4S)-3-Methyl-4-(5-phenylindoline-1-carbonyl)pyrrolidine-1-carbonitrile Example 20 (3R,4R)-3-Methyl-4-(5-phenylindoline-1-carbonyl)pyrrolidine-1-carbonitrile

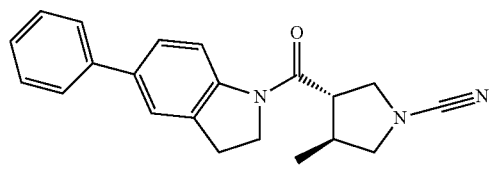

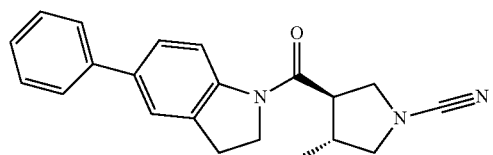

The title compounds were synthesised as a racemic mixture using a procedure similar to that described for Example 17, using (3R,4R)-rel-1-(tert-butoxycarbonyl)-4-methylpyrrolidine-3-carboxylic acid (CAS Number 1253791-53-5) in step d. The enantiomers were separated by preparative chiral HPLC; mobile phase: (A) 100% n-hexane and (B) 100% IPA, column: Chiralpak IB 250×20.0 mm, 5 micron, column flow was 15.0 ml/min to provide:

Example 19

LCMS: Method B, 4.54 min, MS: ES+332.32; Chiral HPLC: Method A, 10.21 min; ¹H NMR (400 MHz, DMSO-d6) δ ppm 8.17 (d, J=8.4 Hz, 1H), 7.64 (d, J=7.6 Hz, 2H), 7.58 (s, 1H), 7.44-7.57 (m, 3H), 7.33 (d, J=6.0 Hz, 1H), 4.23-4.29 (m, 2H), 3.80 (t, J=8.0 Hz, 1H), 3.58-3.61 (m, 1H), 3.48-3.52 (m, 1H), 3.20-3.25 (m, 2H), 3.07-3.16 (m, 2H), 2.55-2.59 (m, 1H), 1.07 (d, J=6.8 Hz, 3H).

Example 20

LCMS: Method B, 4.54 min, MS: ES+332.32; Chiral HPLC: Method A, 10.85 min; ¹H NMR (400 MHz, DMSO-d6) δ ppm 8.17 (d, J=8.4 Hz, 1H), 7.64 (d, J=8.8 Hz, 2H), 7.58 (s, 1H), 7.42-7.51 (m, 3H), 7.31-7.35 (m, 1H), 4.21-4.26 (m, 2H), 3.78-3.82 (m, 1H), 3.58-3.62 (m, 1H), 3.48-3.52 (m, 1H), 3.21-3.25 (m, 2H), 3.07-3.16 (m, 2H), 2.55-2.59 (m, 1H), 1.07 (d, J=6.8 Hz, 3H).

Example 21 (S)-3-(5-Phenyl-2,3-dihydro-1H-pyrrolo[2,3-b]pyridine-1-carbonyl)pyrrolidine-1-carbonitrile

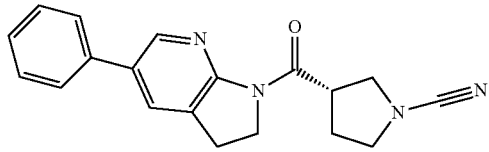 [SMILES: N#CN1CC[C@H](C(=O)N2CCc3cc(-c4ccccc4)cnc32)C1]

The title compound was synthesised using a procedure similar to that described for Example 17, using (S)-1-(tert-butoxycarbonyl)-pyrrolidine-3-carboxylic acid in step d. LCMS: Method A, 4.77 min, MS: ES+319.15; ¹H NMR (400 MHz, DMSO-d6) δ ppm 8.45 (d, J=2.0 Hz, 1H), 8.00 (t, J=1.2 Hz, 1H), 7.69 (dd, J=1.6 Hz, 18.4 Hz, 2H), 7.48 (t, J=8.0 Hz, 2H), 7.37-7.419 (m, 1H), 4.57-4.64 (m, 1H), 4.05 (t, J=8.0 Hz, 2H), 3.68-3.72 (m, 1H), 3.55-3.58 (m, 1H), 3.47 (t, J=7.2 Hz, 2H), 3.13 (t, J=8.8 Hz, 2H), 2.19-2.25 (m, 1H), 2.07-2.14 (m, 1H).

Example 22 3-Fluoro-3-(5-phenyl-2,3-dihydro-1H-pyrrolo[2,3-b]pyridine-1-carbonyl)pyrrolidine-1-carbonitrile

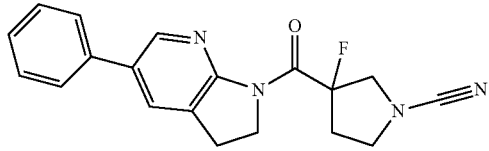 [SMILES: N#CN1CCC(F)(C(=O)N2CCc3cc(-c4ccccc4)cnc32)C1]

The title compound was synthesised using a procedure similar to that described for Example 17, using 1-(tert-butoxycarbonyl)-3-fluoropyrrolidine-3-carboxylic acid (CAS Number 1001754-59-1) in step d. LCMS: Method A, 4.60 min, MS: ES+337.00; ¹H NMR (400 MHz, DMSO-d6) δ ppm 8.48 (d, J=6.4 Hz, 1H), 8.03 (s, 1H), 7.70 (d, J=7.2 Hz, 2H), 7.49 (t, J=7.6 Hz, 2H), 7.40 (t, J=7.6 Hz, 1H), 4.10-4.28 (m, 4H), 3.72-3.78 (m, 1H), 3.58-3.63 (m, 1H), 3.14-3.17 (m, 2H), 2.74-2.86 (m, 1H), 2.56-2.63 (m, 1H).

Example 23 (S)-3-(6-Phenyl-1,2,3,4-tetrahydroquinoline-1-carbonyl)pyrrolidine-1-carbonitrile

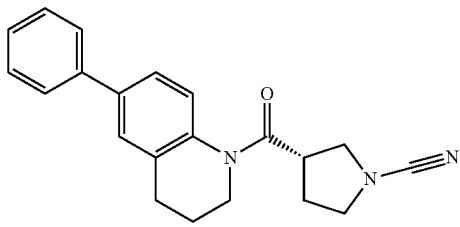 [SMILES: N#CN1CC[C@H](C(=O)N2CCCc3cc(-c4ccccc4)ccc32)C1]

The title compound was synthesised using a procedure similar to that described for Example 17, using (S)-1-(tert-butoxycarbonyl)-pyrrolidine-3-carboxylic acid in step d. LCMS: Method B, 4.46 min, MS: ES+332.6; ¹H NMR (400 MHz, CDCl₃) δ ppm 7.60 (d, J=7.2 Hz, 2H), 7.46-7.50 (m, 4H), 7.37-7.41 (m, 1H), 7.10 (br s, 1H), 3.85 (t, J=6.8 Hz, 2H), 3.62-3.68 (m, 3H), 3.57-3.59 (m, 1H), 3.38-3.47 (m, 1H), 2.75-2.83 (m, 2H), 2.24-2.29 (m, 1H), 2.02-2.07 (m, 3H).

Example 24 (R)-3-(7-Phenyl-3,4-dihydro-2H-benzo[b][1,4]oxazine-4-carbonyl)pyrrolidine-1-carbonitrile

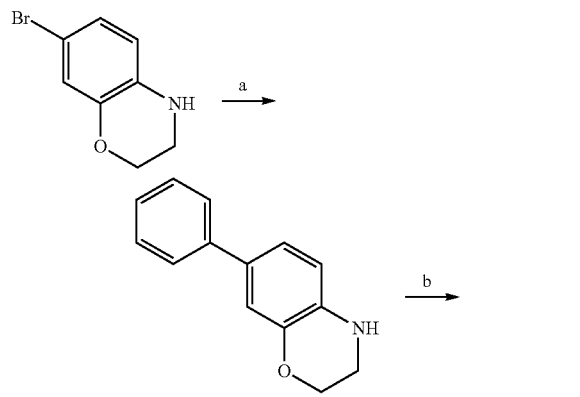

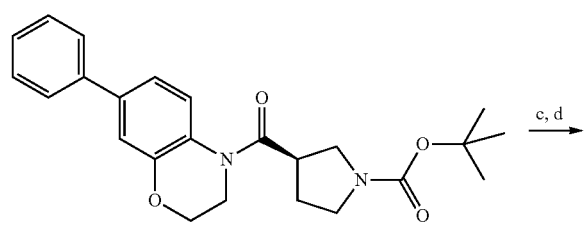

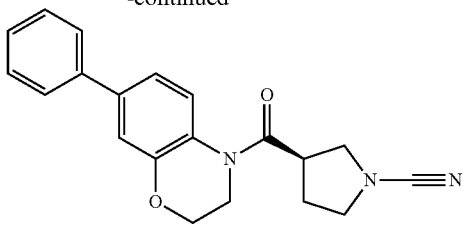

Step a.

To a solution of 7-bromo-3,4-dihydro-2H-benzo[b][1,4]oxazine (CAS Number 105679-22-9; 0.25 g, 1.17 mmol) in 1,4-dioxane:water (5:1, 18 ml) were added phenylboronic acid (0.14 g, 1.17 mmol) and K₂CO₃ (0.48 g, 3.5 mmol) at rt. The resulting reaction mixture was degassed for 20 min under N₂ atmosphere before addition of tetrakis(triphenylphosphine)palladium (0.13 g, 0.12 mmol). The reaction mixture was heated at 80° C. for 1 h. The resulting reaction mixture was poured into water (50 ml) and extracted with EtOAc (3×25 ml). The combined organic phase was dried over Na₂SO₄, filtered and concentrated under reduced pressure. The resulting residue was purified by column chromatography (15% EtOAc in hexane) yielding 7-phenyl-3,4-dihydro-2H-benzo[b][1,4]oxazine (0.127 g, 0.60 mmol). LCMS: Method C, 2.31 min, MS: ES+212.75.

Step b.

To a solution of (R)-1-(tert-butoxycarbonyl)pyrrolidine-3-carboxylic acid (CAS Number 72925-16-7; 0.11 g, 0.52 mmol) in DCM (8 ml) was added N-methylmorpholine (0.15 g, 1.56 mmol) at 0° C. Isobutyl chloroformate (0.085 g, 0.62 mmol) was added dropwise to the reaction mixture at 0° C. The reaction mixture was stirred at rt for 7 h. A solution of 7-phenyl-3,4-dihydro-2H-benzo[b][1,4]oxazine (0.119 g, 0.56 mmol) in DCM (1 ml) was added to the reaction mixture at rt. The reaction mixture was heated at 50° C. for 16 h. The resulting reaction mixture was cooled to rt and poured into water (20 ml). The obtained mixture was extracted with DCM (2×20 ml). The combined organic phase was dried over Na₂SO₄, filtered and concentrated under reduced pressure. The resulting residue was purified by column chromatography (22% EtOAc in hexane) yielding tert-butyl (R)-3-(7-phenyl-3,4-dihydro-2H-benzo[b][1,4]oxazine-4-carbonyl)pyrrolidine-1-carboxylate (0.040 g, 0.10 mmol). LCMS: Method C, 2.75 min, MS: ES+353.6 (M−56), 409.8 (M+1).

Steps c, d.

The title compound was synthesised from the intermediate above using a procedure similar to that described for Example 1, steps d, e. LCMS: Method B, 4.48 min, MS: ES+334.64, ¹H NMR (400 MHz, DMSO-d6) δ ppm 7.8-7.9 (m, 1H), 7.63-7.65 (m, 2H), 7.43-7.46 (m, 2H), 7.33-7.37 (m, 1H), 7.18-7.21 (m, 2H), 4.34 (t, J=4.8 Hz, 2H), 3.92-4.01 (m, 2H), 3.69-3.79 (m, 1H), 3.55-3.64 (m, 2H), 3.39-3.51 (m, 2H), 2.14-2.12 (m, 1H), 2.06-2.13 (m, 1H).

Example 25 (R)-3-(6-Phenyl-3,4-dihydro-2H-benzo[b][1,4]oxazine-4-carbonyl)pyrrolidine-1-carbonitrile

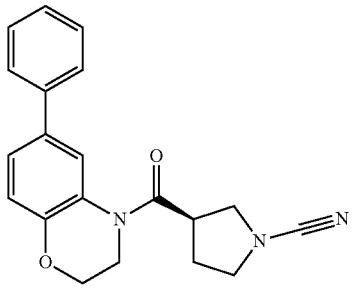 [SMILES: N#CN1CC[C@@H](C(=O)N2CCOc3ccc(-c4ccccc4)cc32)C1]

The title compound was synthesised using a procedure similar to that described for Example 24. LCMS: Method B, 4.46 min, MS: ES+334.64; ¹H NMR (400 MHz, DMSO-d6) δ ppm 8.37 (s, 1H), 7.56-7.58 (m, 2H), 7.42-7.46 (m, 2H), 7.30-7.38 (m, 2H), 6.99 (d, J=8.8 Hz, 1H), 4.32-4.35 (m, 2H), 3.96-3.98 (m, 2H), 3.71-3.73 (m, 1H), 3.60-3.63 (m, 2H), 3.39-3.49 (m, 2H), 2.12-2.15 (s, 1H), 2.04-2.11 (m, 1H).

Example 26 (R)-3-(8-Phenyl-3,4-dihydro-2H-benzo[b][1,4]oxazine-4-carbonyl)pyrrolidine-1-carbonitrile

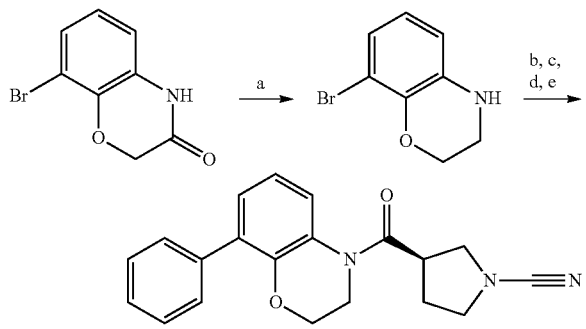

Step a.

To a solution of 8-bromo-2H-benzo[b][1,4]oxazin-3(4H)-one (CAS Number 688363-48-6; 0.600 g, 2.63 mmol) in THF (10 ml) was added BH₃.DMS complex (0.5 ml, 5.263 mmol) at 0° C. The reaction mixture was heated at 78° C. for 1 h. The resulting reaction mixture was cooled to rt and poured into MeOH (60 ml). The obtained reaction mixture was concentrated under reduced pressure yielding 8-bromo-3,4-dihydro-2H-benzo[b][1,4]oxazine (0.550 g, 2.57 mmol). LCMS: Method C, 2.18 min, MS: ES+214.0. This material was used directly for the next step without further purification.

Steps b, c, d, e.

The title compound was synthesised from the intermediate above using a procedure similar to that described for Example 24. LCMS: Method C, 2.34 min, MS: ES+334.23; ¹H NMR (400 MHz, DMSO-d6) δ ppm 7.86 (s, 1H), 7.48 (d, J=7.6 Hz, 2H), 7.41 (t, J=7.2 Hz, 2H), 7.31-7.35 (m, 1 H), 7.07-7.10 (m, 1H), 6.96-6.98 (m, 1H), 4.30 (t, J=4 Hz, 2H), 3.93-3.96 (s, 2H), 3.70-3.73 (s, 1H), 3.56-3.63 (m, 2H), 3.37-3.50 (m, 2H), 2.12-2.16 (s, 1H), 1.99-2.08 (m, 1H).

Example 27 (S)-3-(4-Phenyl-2,3-dihydro-1H-pyrrolo[2,3-b]pyridine-1-carbonyl)pyrrolidine-1-carbonitrile

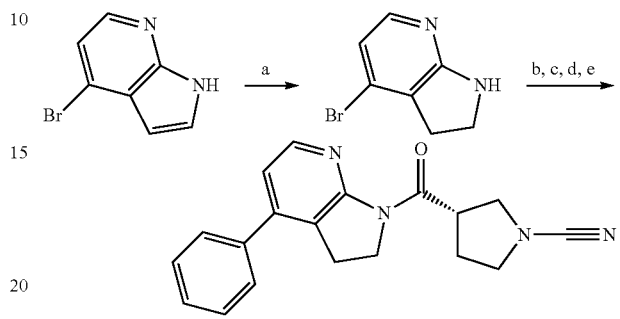

Step a.

To a solution of 4-bromo-1H-pyrrolo[2,3-b]pyridine (CAS Number 348640-06-2; 2.5 g, 12.8 mmol) in THF (25 ml) was added BH₃.DMS complex (7.00 ml, 73.7 mmol) at rt. The resulting reaction mixture was heated at 80° C. for 16 h. The resulting reaction mixture was cooled to rt and concentrated under reduced pressure. The resulting residue was triturated with diethyl ether (2×5 ml) and dried under high vacuum yielding 4-bromo-2,3-dihydro-1H-pyrrolo[2,3-b]pyridine (2.1 g, 10.55 mmol). LCMS: Method C, 1.29 min, MS: ES+199.00; ¹H NMR (400 MHz, DMSO-d6) δ ppm 7.53 (d, J=5.2 Hz, 1H), 7.24 (br s, 1H), 7.63 (d, J=6.0 Hz, 1H), 3.57 (t, J=8.4 Hz, 2H), 2.99 (t, J=8.8 Hz, 2H). This material was used directly for the next step without further purification.

Steps b, c, d, e.

The title compound was synthesised from the intermediate above using a procedure similar to that described for Example 17, steps c, d, e, f, using (S)-1-(tert-butoxycarbonyl)-pyrrolidine-3-carboxylic acid in step d. LCMS: Method A, 4.78 min, MS: ES+318.97; ¹H NMR (400 MHz, DMSO-d6) δ ppm 8.20 (d, J=5.6 Hz, 1H), 7.57-7.59 (m, 2H), 7.46-7.53 (m, 3H), 7.12 (d, J=5.6 Hz, 1H), 4.59-4.62 (m, 1H), 3.99 (t, J=8 Hz, 2H), 3.66-3.70 (m, 1H), 3.53-3.56 (m, 1H), 3.45 (t, J=6.8 Hz, 2H), 3.17 (t, J=8.4 Hz, 2H), 2.18-2.23 (m, 1H), 2.05-2.10 (m, 1H).

Example 28 (S)-3-(4-(3-Chlorophenyl)-2,3-dihydro-1H-pyrrolo[2,3-b]pyridine-1-carbonyl)pyrrolidine-1-carbonitrile

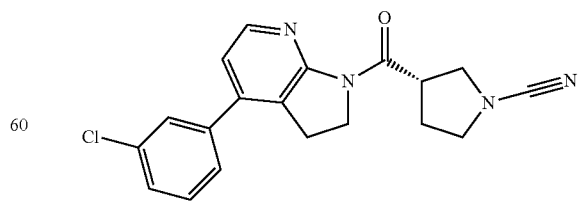

The title compound was synthesised using a procedure similar to that described for Example 23. LCMS: Method C, 2.41 min, MS: ES+353.34; ¹H NMR (400 MHz, DMSO-d6)

δ ppm 8.22 (d, J=5.2 Hz, 1H), 7.66 (s, 1H), 7.54-7.56 (m, 3H), 7.15 (d, J=5.2 Hz, 1H), 4.58-4.62 (m, 1H), 4.00 (t, J=8.4 Hz, 2H), 3.67-3.71 (m, 1H), 3.54-3.58 (m, 1H), 3.46 (t, J=7.2 Hz, 2H), 3.18 (t, J=8.4 Hz, 2H), 2.18-2.33 (m, 1H), 2.04-2.11 (m, 1H).

Example 29 (S)-1-(1-Cyanopyrrolidine-3-carbonyl)-5-(1-methyl-1H-pyrazol-4-yl)indoline-6-carbonitrile

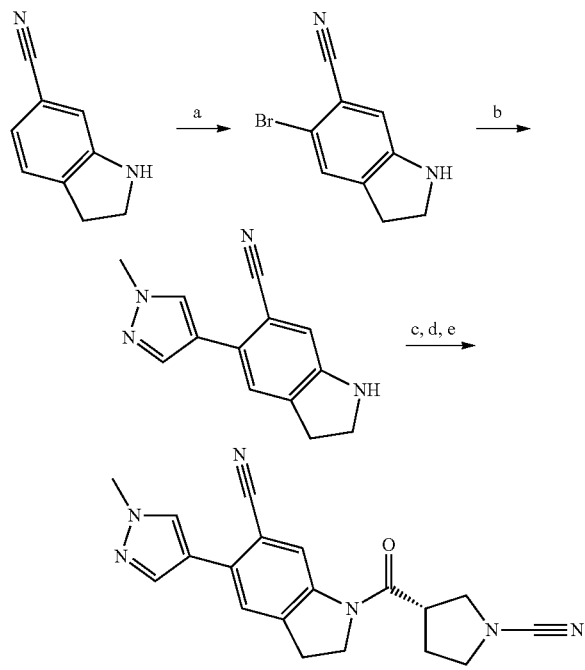

Step a.

To a stirred solution of indole-6-carbonitrile (0.3 g, 2.08 mmol) in MeCN (10 ml) was added N-bromosuccinimide (0.37 g, 2.09 mmol) at 0° C. The reaction mixture was stirred at rt for 20 min. The reaction mixture was poured into saturated solution of NaHCO$_3$ solution (30 ml) and extracted with EtOAc (3×20 ml). The combined organic phase was separated, dried over Na$_2$SO$_4$, filtered and concentrated under reduced pressure. The resulting crude material was purified by flash chromatography (60% DCM in hexane) yielding 5-bromoindoline-6-carbonitrile (0.335 g, 1.51 mmol). LCMS: Method C, 2.00 min, MS: ES+223.1, 225.1 (M+2); $^1$H NMR (400 MHz, CDCl$_3$) δ ppm 7.33 (s, 1H), 6.79 (s, 1H), 3.99 (s, 1H), 3.64-3.69 (m, 2H), 3.08-3.13 (m, 2H).

Step b.

To a stirred solution of 5-bromoindoline-6-carbonitrile (0.3 g, 1.35 mmol) in 1,4-dioxane:water (3:2; 10 ml) was added 1-methyl-4-(4,4,5,5-tetramethyl-1,3,2-dioxaborolan-2-yl)-1H-pyrazole (CAS Number 761446-44-0; 0.39 g, 1.89 mmol) and K$_2$CO$_3$ (0.373 g, 2.70 mmol) at rt. The reaction mixture was degassed for 15 min before adding PdCl$_2$(dppf) (0.098 g, 0.135 mmol). The reaction mixture was heated at 100° C. for 2 h. The resulting reaction mixture was cooled to rt, poured into water (25 ml) and extracted with EtOAc (3×20 ml). The combined organic phase was separated, dried over Na$_2$SO$_4$, filtered and concentrated under reduced pressure. The resulting crude material was purified by flash chromatography (55% EtOAc in hexane) yielding 5-(1-methyl-1H-pyrazol-4-yl)indoline-6-carbonitrile (0.26 g, 1.11 mmol). LCMS: Method C, 1.81 min, MS: ES+225.14.

Steps c, d, e.

The title compound was synthesised from the intermediate above using a procedure similar to that described for Example 7, steps b, c, d, using (S)-1-(tert-butoxycarbonyl)-pyrrolidine-3-carboxylic acid in step c. LCMS: Method B, 3.41 min, MS: ES+347.27; $^1$H NMR (400 MHz, DMSO-d6) δ ppm 8.33 (s, 1H), 8.22 (s, 1H), 7.92 (s, 1H), 7.62 (s, 1H), 4.24 (t, J=8.0 Hz, 2H), 3.91 (s, 3H), 3.59-3.66 (m, 2H), 3.42-3.51 (m, 3H), 3.27 (t, J=8.0 Hz, 2H), 2.19-2.23 (m, 1H), 2.05-2.10 (m, 1H).

Example 30 (R)-3-(7-(1H-Pyrazol-1-yl)-3,4-dihydro-2H-benzo[b][1,4]oxazine-4-carbonyl)-pyrrolidine-1-carbonitrile

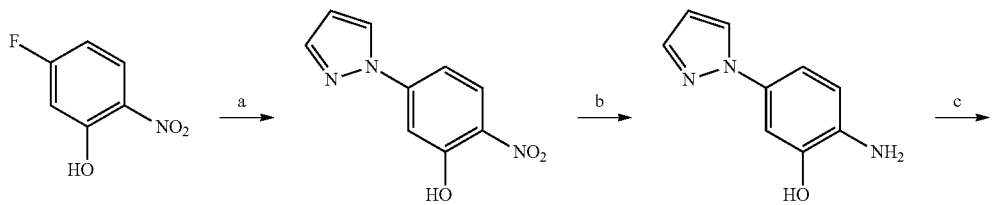

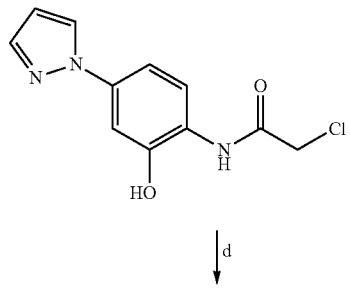

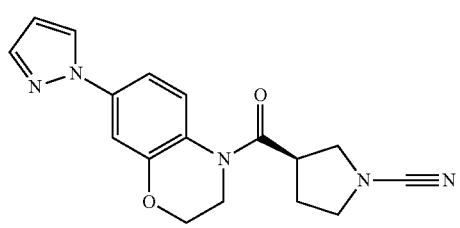 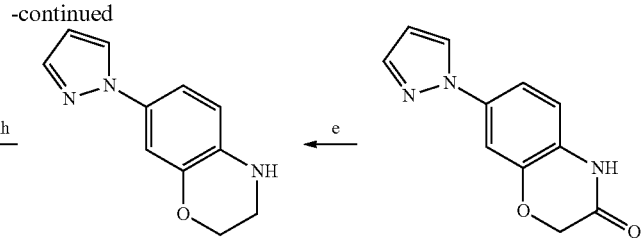

Step a.

To a solution of 1H-pyrazole (3.9 g, 57.3 mmol) in DMF (40 ml) was added Cs₂CO₃ (18.6 g, 57.3 mmol) and CuI (0.36 g, 1.91 mmol) at rt. The reaction mixture was stirred at rt for 15 min before adding 5-fluoro-2-nitrophenol (3.0 g, 19.1 mmol). The reaction mixture was heated at 140° C. for 48 h. The resulting reaction mixture was poured into water (150 ml) and extracted with EtOAc (5×100 ml). The combined organic phase was dried over Na₂SO₄, filtered and concentrated under reduced pressure. The resulting residue was purified by column chromatography (5% EtOAc in hexane) yielding 2-nitro-5-(1H-pyrazol-1-yl)phenol (2.0 g, 9.75 mmol). LCMS: Method C, 2.02 min, MS: ES−204.11 (M−1).

Step b.

To a solution of 2-nitro-5-(1H-pyrazol-1-yl) phenol (1 g, 4.87 mmol) in EtOH (10 ml) was added iron powder (0.81 g, 14.6 mmol), ammonium chloride (2.61 g, 48.7 mmol) and water (5 ml) at rt. The resulting reaction mixture was heated at 80° C. for 1 h. The resulting reaction mixture was diluted with EtOAc (60 ml) and filtered through celite hyflow. The celite bed was washed with EtOAc (30 ml) and the combined filtrate was dried over Na₂SO₄, concentrated under reduced pressure to yield 2-amino-5-(1H-pyrazol-1-yl)phenol (0.7 g, 3.99 mmol). LCMS: Method C, 1.23 min, MS: ES+176.14. This material was directly used for the next step without further purification.

Step c.

To a solution of 2-amino-5-(1H-pyrazol-1-yl)phenol (1.6 g, 9.13 mmol) in 1,2-dimethoxyethane (20 ml) was added DIPEA (1.77 g, 13.70 mmol) at 0° C. and stirred for 10 min. Chloroacetyl chloride (1.23 g, 10.96 mmol) was added to the reaction mixture at 0° C. The reaction mixture was heated at 85° C. for 17 h. The resulting reaction mixture was cooled to rt and poured into water (40 ml). The obtained mixture was extracted with EtOAc (3×30 ml). The combined organic phase was dried over Na₂SO₄, filtered and concentrated under reduced pressure yielding 2-chloro-N-(2-hydroxy-4-(1H-pyrazol-1-yl) phenyl)acetamide (3 g, 11.9 mmol). LCMS: Method C, 1.76 min, MS: ES+252.25. This material was directly used for the next step without further purification.

Step d.

To a solution of 2-chloro-N-(2-hydroxy-4-(1H-pyrazol-1-yl)phenyl)acetamide (3 g, 11.9 mmol) in 1,2-dimethoxyethane (20 ml) was added NaHCO₃ (3 g, 35.8 mmol). The reaction mixture was heated at 90° C. for 6 hrs. The resulting reaction mixture was poured into water (60 ml) and extracted with EtOAc (4×60 ml). The combined organic phase was dried over Na₂SO₄, filtered and concentrated under reduced pressure. The obtained residue was purified using column chromatography (35% EtOAc in hexane) to yield 7-(1H-pyrazol-1-yl)-2H-benzo[b][1,4]oxazin-3(4H)-one (0.22 g, 1.02 mmol). LCMS: Method C, 1.72 min, MS: ES+216.21.

Step e.

To a solution of 7-(1H-pyrazol-1-yl)-2H-benzo[b][1,4] oxazin-3(4H)-one (0.19 g, 0.88 mmol) in THF (20 ml) was added BH₃-DMS (0.17 g, 2.21 mmol) at 0° C. The reaction mixture was stirred at 70° C. for 54 h. The reaction was cooled to rt and poured into water (25 ml). The obtained mixture was extracted with EtOAc (2×25 ml). The combined organic phase was dried over Na₂SO₄, filtered and concentrated under reduced pressure yielding 7-(1H-pyrazol-1-yl)-3,4-dihydro-2H-benzo[b][1,4]oxazine (0.13 g, 0.646 mmol). LCMS: Method C, 1.90 min, MS: ES+202.4.

Steps f, g, h.

The title compound was synthesised from the intermediate above using a procedure similar to that described for Example 24, steps b, c, d. LCMS: Method B, 3.67 min, MS: ES+324.4, ¹H NMR (400 MHz, DMSO-d6) δ ppm 8.40 (d, J=2.4 Hz, 1H), 7.88-7.89 (m, 1H), 7.70 (d, J=1.6 Hz, 1H), 7.35-7.38 (m, 2H), 6.5-6.51 (m, 1H), 4.36 (t, J=4.8 Hz, 2H), 3.39-4.02 (m, 2H), 3.69-3.76 (m, 1H), 3.55-3.63 (m, 2H), 3.38-3.50 (m, 2H), 2.15-2.21 (m, 1H), 2.06-2.13 (m, 1H).

Example 31 (S)-1-Cyano-N-methyl-N-(5-phenylpyridin-2-yl)pyrrolidine-3-carboxamide

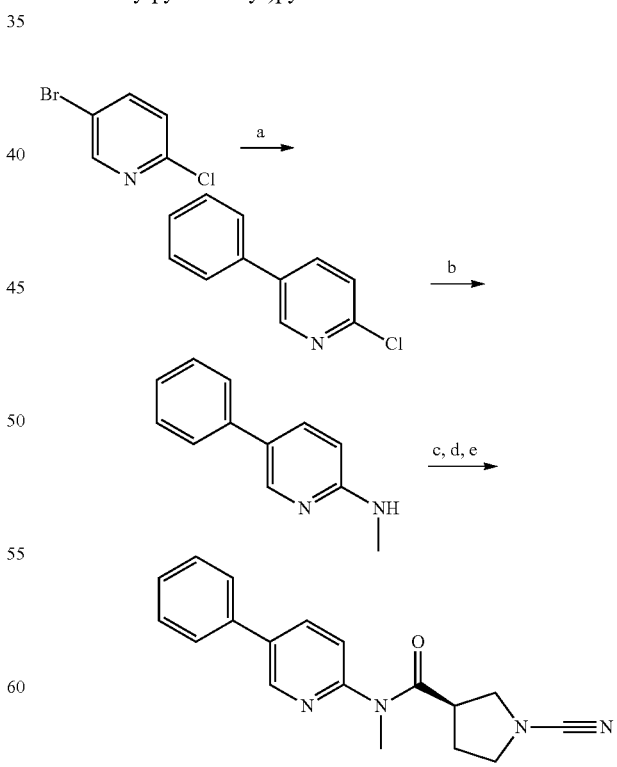

Step a.

To a stirred solution of 5-bromo-2-chloropyridine (CAS Number 53939-30-3; 0.5 g, 2.60 mmol) in 1,4-dioxane:

water (4:1; 10 ml) was added K₂CO₃ (0.72 g, 5.20 mmol) at rt. The reaction mixture was degassed for 15 min before adding Pd(PPh₃)₄ (0.029 g, 0.026 mmol) and phenylboronic acid (0.348 g, 2.86 mmol). The reaction mixture was heated to 100° C. for 18 h. The resulting reaction mixture was cooled to rt, poured into water (20 ml) and extracted with EtOAc (3×20 ml). The combined organic phase was washed with brine (20 ml), dried over Na₂SO₄, filtered and concentrated under reduced pressure. The resulting crude material was purified by flash chromatography (5% EtOAc in hexane) yielding a mixture of 2-chloro-5-phenylpyridine and 2,5-diphenylpyridine (0.61 g, quantitative). This material was used for the next step without further purification. LCMS: Method C, 2.23 min, MS: ES+190.09.

Step b.

To a stirred solution of 5-phenylpyridine and 2,5-diphenylpyridine (mixture isolated in step a; 0.55 g, 2.9 mmol) in methylamine (40% in water; 0.464 g, 14.5 mmol) was added copper powder (0.148 g, 2.32 mmol) at rt. The reaction mixture was heated at 100° C. for 18 h. The resulting reaction mixture cooled to rt, poured into water (20 ml) and extracted with EtOAc (3×20 ml). The combined organic phase was washed with brine (20 ml), dried over Na₂SO₄, filtered and concentrated under reduced pressure. The resulting crude material was purified by flash chromatography (15% EtOAc in hexane) yielding N-methyl-5-phenylpyridin-2-amine (0.3 g, 1.63 mmol). LCMS: Method C, 1.48 min, MS: ES+184.8; ¹H NMR (400 MHz, DMSO-d6) δ ppm 8.32 (d, J=2.4 Hz, 1H), 7.70 (dd, J=2.4 Hz, 8.8 Hz, 1H), 7.57 (d, J=8.4 Hz, 2H), 7.41 (t, J=8.0 Hz, 2H), 7.27 (t, J=7.2 Hz, 1H), 6.64 (q, J=4.8 Hz, 1H), 6.53 (d, J=8.4 Hz, 1H), 2.80 (d, J=4.8 Hz, 3H).

Steps c, d.

The title compound was synthesised from the intermediate above using a procedure similar to that described for Example 1, steps d, e. LCMS: Method A, 4.10 min, MS: ES+306.99; ¹H NMR (400 MHz, DMSO-d6) δ ppm 8.82 (d, J=2.0 Hz, 1H), 8.23 (dd, J=2.4 Hz, 8.4 Hz, 1H), 7.78 (d, J=8.4 Hz, 2H), 7.61 (d, J=8.0 Hz, 1H), 7.53 (t, J=8.0 Hz, 2H), 7.45 (t, J=7.2 Hz, 1H), 3.41-3.51 (m, 5H), 3.32 (s, 3H), 1.98-2.05 (m, 2H).

Example 32 (R)-1-Cyano-N-methyl-N-(5-phenylpyridazin-3-yl)pyrrolidine-3-carboxamide

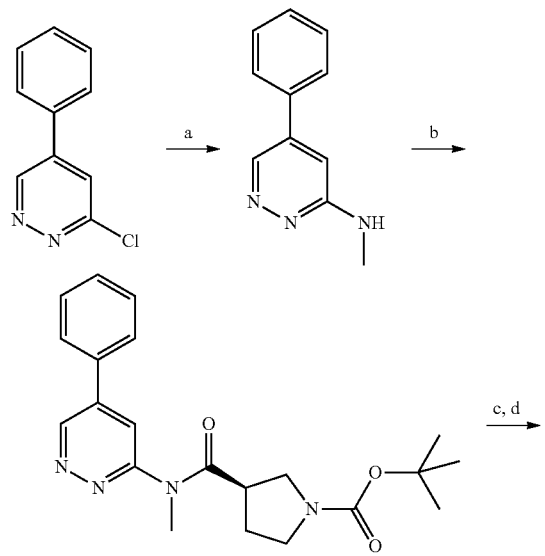

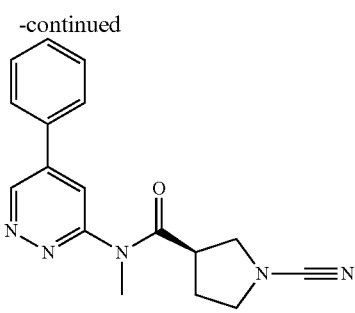

Step a.

To a stirred solution of 3-chloro-5-phenylpyridazine (0.6 g, 3.05 mmol) in methyl amine (40% in water) (1 ml) was added copper powder (0.19 g, 3.05 mmol) at rt. The reaction mixture was heated at 100° C. for 18 h. The resulting reaction mixture cooled to rt, poured into water (20 ml) and extracted with EtOAc (3×20 ml). The combined organic phase was washed with brine (20 ml), dried over Na₂SO₄, filtered and concentrated under reduced pressure. The resulting crude material was purified by flash chromatography (22% EtOAc in hexane) yielding N-methyl-5-phenylpyridazin-3-amine (0.4 g, 2.16 mmol). LCMS: Method C, 1.40 min, MS: ES+185.8.

Step b.

To a stirred solution of DMF (0.099 g, 1.39 mmol) in DCM (1 ml) was added pyridine (0.11 g, 1.39 mmol) dropwise at 0° C. The reaction mixture was stirred for 15 min before adding oxalyl chloride (0.176 g, 1.39 mmol) dropwise at 0° C. The reaction mixture was stirred at rt for 30 min before addition of (R)-1-(tert-butoxycarbonyl)pyrrolidine-3-carboxylic acid (CAS Number 72925-16-7; 0.3 g, 1.39 mmol) at 0° C. The reaction mixture was stirred for 15 min before adding a solution of N-methyl-5-phenylpyridazin-3-amine (0.206 g, 1.12 mmol) and TEA (0.42 g, 4.17 mmol) in THF (1 ml) at 0° C. The reaction mixture was stirred at rt for 4 h. The resulting reaction mixture was poured into water (10 ml) and extracted with EtOAc (3×20 ml). The combined organic phase was washed with brine (20 ml), dried over Na₂SO₄, filtered and concentrated under reduced pressure. The resulting crude material was purified by flash chromatography (1.5% MeOH in DCM) yielding tert-butyl (R)-3-(methyl(5-phenylpyridazin-3-yl)carbamoyl)pyrrolidine-1-carboxylate (0.19 g, 0.50 mmol). LCMS: Method C, 2.04 min, MS: ES+383.43.

Steps c, d.

The title compound was synthesised from the intermediate above using a procedure similar to that described for Example 1, steps d, e. LCMS: Method B, 3.21 min, MS: ES+308.27; ¹H NMR (400 MHz, DMSO-d6) δ ppm 9.62 (d, J=2.0 Hz, 1H), 8.20 (d, J=2.4 Hz, 1H), 7.98 (dd, J=1.6 Hz, 7.6 Hz, 2H), 7.58-7.63 (m, 3H), 3.44-3.53 (m, 3H), 3.43 (s, 3H), 3.30-3.32 (m, 2H), 2.03-2.08 (m, 2H).

Example 33 1-Cyano-3-fluoro-N-methyl-N-(5-phenylisoxazol-3-yl)pyrrolidine-3-carboxamide

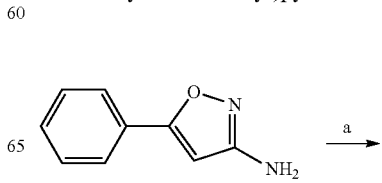

-continued

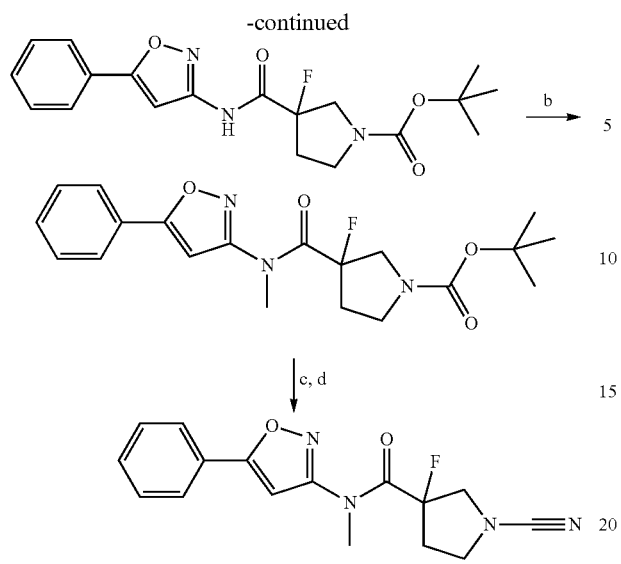

Step a.

To a solution of 1-(tert-butoxycarbonyl)-3-fluoropyrrolidine-3-carboxylic acid (CAS Number 1001754-59-1; 0.050 g, 0.214 mmol) in DCM (2 ml) was added 5-phenylisoxazol-3-amine (CAS Number 6455-31-8; 0.034 g, 0.214 mmol) and pyridine (0.19 ml, 2.36 mmol) at 0° C. The reaction mixture was stirred for 5 min before adding POCl₃ (0.2 ml, 2.14 mmol) dropwise at 0° C. The reaction mixture was stirred at 0° C. for 3 h. The resulting reaction mixture was poured into saturated NaHCO₃ solution (70 ml) and extracted with DCM (3×50 ml). The combined organic phase was dried over Na₂SO₄, filtered and concentrated under reduced pressure yielding tert-butyl 3-fluoro-3-((5-phenylisoxazol-3-yl)carbamoyl)pyrrolidine-1-carboxylate (0.080 g, 0.213 mmol). LCMS: Method C, 2.55 min, MS: ES+376.3. This material was used directly for the next step without further purification.

Step b.

To a solution of tert-butyl 3-fluoro-3-((5-phenylisoxazol-3-yl)carbamoyl)pyrrolidine-1-carboxylate (0.040 g, 0.106 mmol) in DMF (2 ml) was added K₂CO₃ (0.044 g, 0.319 mmol) at 0° C. The reaction mixture was stirred for 5 min before adding methyl iodide (0.015 g, 0.106 mmol) at 0° C. The reaction mixture was stirred at 0° C. for 3 h. The resulting reaction mixture was poured into cold water (70 ml) and extracted with EtOAc (3×50 ml). The combined organic phase was dried over Na₂SO₄, filtered and concentrated under reduced pressure yielding tert-butyl 3-fluoro-3-(methyl(5-phenylisoxazol-3-yl)carbamoyl)pyrrolidine-1-carboxylate (0.045 g, 0.115 mmol). LCMS: Method A, 5.46 min, MS: ES+289.97 (M−100). This material was used directly for the next step without further purification.

Steps c, d, e.

The title compound was synthesised from the intermediate above using a procedure similar to that described for Example 4, steps d, e, f. LCMS: Method A, 4.53 min, MS: ES+314.98, ¹H NMR (400 MHz, DMSO-d6) δ ppm 7.88-7.91 (m, 2H), 7.55-7.59 (m, 3H), 7.35 (s, 1H), 3.98-4.09 (m, 1H), 3.82-3.92 (m, 1H), 3.64-3.70 (m, 1H), 3.48-3.54 (m, 1H), 3.37 (s, 3H), 2.56-2.71 (m, 1H), 2.45-2.50 (m, 1H).

Example 34 (trans)-1-Cyano-4-(hydroxymethyl)-N-methyl-N-(5-phenylthiazol-2-yl)pyrrolidine-3-carboxamide

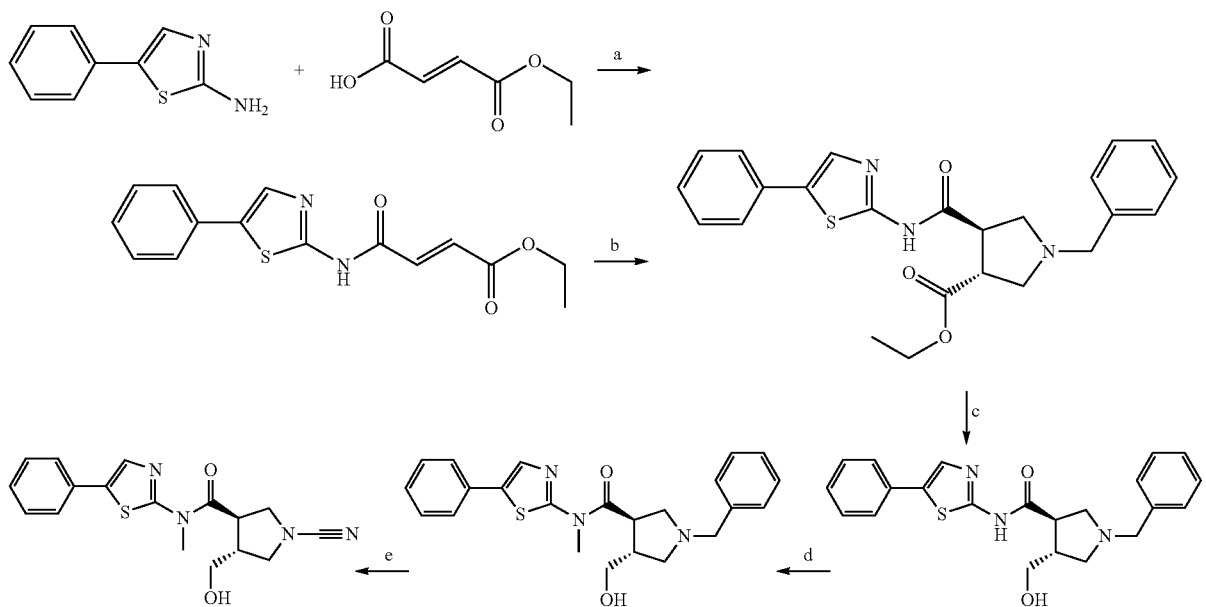

Step a.

To a stirred solution of ethyl fumarate (CAS Number 2459-05-4; 5.0 g, 34.7 mmol) in THF (50 ml) were added EDC.HCl (7.3 g, 38.2 mmol) and HOBt (2.6 g, 17.4 mmol) at rt. The reaction mixture was stirred at rt for 30 min. 2-Amino-5-phenylthiazole (CAS Number 39136-63-5; 6.1 g, 34.7 mmol) was added portion wise to the reaction mixture. The reaction mixture was stirred at rt for 1.5 h. The resulting reaction mixture was poured into water (600 ml). The obtained precipitates were filtered under vacuum and dried yielding ethyl (E)-4-oxo-4-((5-phenylthiazol-2-yl)amino)but-2-enoate (12.35 g, quantitative). This material was used for the next step without further purification. LCMS: Method C, 2.16 min, MS: ES+303.23; ¹H NMR (400 MHz, DMSO-d6) δ ppm 12.82 (br s, 1H), 7.98 (s, 1H), 7.64 (d, J=7.2 Hz, 2H), 7.44 (t, J=7.6 Hz, 2H), 7.31-7.35 (m, 1H), 7.28 (d, J=15.6 Hz, 1H), 6.84 (d, J=15.6 Hz, 1H), 4.23 (q, J=7.2 Hz, 2H), 1.26 (t, J=7.6 Hz, 3H).

Step b.

A mixture of ethyl (E)-4-oxo-4-((5-phenylthiazol-2-yl) amino)but-2-enoate (3.8 g, 12.6 mmol), paraformaldehyde (9.6 g, 2.5 vol. w/w) and N-benzyl glycine (4.15 g, 25.2 mmol) in toluene (200 ml) was refluxed in a Dean Stark apparatus for 3 h. The resulting reaction mixture was cooled to rt, poured into water (200 ml) and extracted with EtOAc (2×150 ml). The combined organic phase was separated, dried over Na$_2$SO$_4$, filtered and concentrated under reduced pressure. The resulting crude material was purified by flash chromatography (40% EtOAc in hexane) yielding trans-ethyl-1-benzyl-4-((5-phenylthiazol-2-yl)carbamoyl)pyrrolidine-3-carboxylate (2.1 g, 4.83 mmol). This material was used for the next step without further purification. LCMS: Method C, 1.85 min, MS: ES+436.43.

Step c.

To a stirred solution of trans-ethyl-1-benzyl-4-((5-phenylthiazol-2-yl)carbamoyl)pyrrolidine-3-carboxylate (2.08 g, 4.78 mmol) in THF (20 ml) was added lithium aluminium hydride solution in THF (1M, 4.78 ml, 4.78 mmol) at 0° C. The reaction mixture was stirred at rt for 15 min. The resulting reaction mixture was quickly poured into EtOAc (100 ml). The obtained mixture was poured into water (80 ml) and filtered through celite hyflow. The organic phase was separated and the aqueous phase was re-extracted with EtOAc (80 ml). The combined organic phase was separated, dried over Na$_2$SO$_4$, filtered and concentrated under reduced pressure. The resulting crude material was purified by column chromatography (2% MeOH in DCM) yielding trans-1-benzyl-4-(hydroxymethyl)-N-(5-phenylthiazol-2-yl)pyrrolidine-3-carboxamide (0.37 g, 0.94 mmol). LCMS: Method C, 1.78 min, MS: ES+394.33.

Step d.

To a stirred solution of trans-1-benzyl-4-(hydroxymethyl)-N-(5-phenylthiazol-2-yl)pyrrolidine-3-carboxamide (0.35 g, 0.89 mmol) in DCM (10 ml) were added tetrabutylammonium iodide (0.033 g, 0.089 mmol), 10% aqueous NaOH solution (0.5 ml) and dimethyl sulfate (0.112 g, 0.89 mmol) at rt. The reaction mixture was stirred at rt for 3 h. The resulting reaction mixture was poured into water (100 ml) and extracted with DCM (3×30 ml). The combined organic phase was separated, dried over Na$_2$SO$_4$, filtered and concentrated under reduced pressure. The resulting crude material was purified by column chromatography (2% MeOH in DCM) yielding trans-1-benzyl-4-(hydroxymethyl)-N-methyl-N-(5-phenylthiazol-2-yl)pyrrolidine-3-carboxamide (0.166 g, 0.41 mmol). LCMS: Method C, 1.75 min, MS: ES+408.3.

Step e.

To a stirred solution of trans-1-benzyl-4-(hydroxymethyl)-N-methyl-N-(5-phenylthiazol-2-yl)pyrrolidine-3-carboxamide (0.14 g, 0.34 mmol) in THF (4 ml) was added K$_2$CO$_3$ (0.047 g, 0.34 mmol) at 0° C. Cyanogen bromide (0.054 g, 0.51 mmol) was added to the reaction mixture at 0° C. The reaction mixture was stirred at rt for 45 min. The resulting reaction mixture was poured into water (30 ml) and extracted with EtOAc (2×20 ml). The combined organic phase was separated, dried over Na$_2$SO$_4$, filtered and concentrated under reduced pressure. The resulting crude material was purified by column chromatography (2.5% MeOH in DCM) yielding trans-1-cyano-4-(hydroxymethyl)-N-methyl-N-(5-phenylthiazol-2-yl)pyrrolidine-3-carboxamide (0.057 g, 0.17 mmol). LCMS: Method B, 3.48 min, MS: ES+343.22; $^1$H NMR (400 MHz, DMSO-d6) δ ppm 8.05 (s, 1H), 7.57 (d, J=7.2 Hz, 2H), 7.46 (t, J=8.0 Hz, 2H), 7.33-7.37 (m, 1H), 4.88 (t, J=5.2 Hz, 1H), 3.73 (s, 3H), 3.63-3.70 (m, 2H), 3.50-3.58 (m, 2H), 3.40-3.44 (m, 1H), 3.26-3.29 (m, 1H), 3.01-3.06 (m, 1H), 2.60-2.65 (m, 1H).

Example 35 3-(5-(1-Benzyl-1H-pyrazol-5-yl)indoline-1-carbonyl)-3-fluoropyrrolidine-1-carbonitrile Synthesis According to General Scheme 3

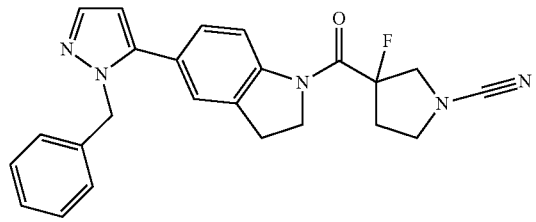 [SMILES: N#CN1CCC(F)(C(=O)N2CCc3cc(-c4ccnn4Cc4ccccc4)ccc32)C1]

Step a.

A solution of 5-bromoindoline (4.5 g, 19.3 mmol), 1-(tert-butoxycarbonyl)-3-fluoropyrrolidine-3-carboxylic acid (CAS Number 1001754-59-1; 3.82 g, 19.3 mmol), T3P (13.51 g, 21.2 mmol, 50% purity), TEA (5.35 ml, 38.6 mmol) in DCM (100 ml) was degassed and purged with N$_2$ and then the mixture was stirred at rt for 3 h. The reaction was concentrated under reduced pressure to give a residue, which was purified by flash silica gel chromatography (ISCO®; 220 g SepaFlash® silica flash column, eluting with 35-65% EtOAc/PE gradient @ 60 ml/min) to afford tert-butyl 3-(5-bromoindoline-1-carbonyl)-3-fluoropyrrolidine-1-carboxylate (7.97 g, 15.7 mmol, 81.5% yield) as a white solid. $^1$H NMR (400 MHz, CDCl$_3$) δ ppm 8.10-8.05 (d, 1H), 7.34-7.31 (m, 2H), 4.40-4.21 (m, 2H), 4.20-3.48 (m, 4H), 3.21-3.18 (m, 2H), 2.85-2.50 (m, 1H), 2.40-2.32 (m, 1H), 1.47 (s, 9H).

Step b.

To a solution of tert-butyl 3-(5-bromoindoline-1-carbonyl)-3-fluoropyrrolidine-1-carboxylate (0.2 mmol), 1-benzyl-5-(4,4,5,5-tetramethyl-1,3,2-dioxaborolan-2-yl)-1H-pyrazole (0.2 mmol) and Cs$_2$CO$_3$ (0.6 mmol, 3 eq) in 1,4-dioxane (1 ml) and water (0.2 ml) was added Pd(PPh$_3$)$_4$ (0.2 eq) at rt under nitrogen. The reaction mixture was stirred at 100° C. for 16 h. The resulting mixture was concentrated under reduced pressure. The resulting residue was purified by prep-TLC (PE:EtOAc=1:1) yielding tert-butyl 3-(5-(1-benzyl-1H-pyrazol-5-yl)indoline-1-carbonyl)-3-fluoropyrrolidine-1-carboxylate, which was used for next step directly without further purification.

Step c.

To a solution of tert-butyl 3-(5-(1-benzyl-1H-pyrazol-5-yl)indoline-1-carbonyl)-3-fluoropyrrolidine-1-carboxylate in EtOAc (1 ml) was added HCl/EtOAc (4M, 1 ml). The reaction mixture was stirred at rt for 2 h. The resulting mixture was concentrated under reduced pressure. The residue (5-(1-benzyl-1H-pyrazol-5-yl)indolin-1-yl)(3-fluoropyrrolidin-3-yl)methanone was used for next step directly without further purification.

Step d.

To a solution of (5-(1-benzyl-1H-pyrazol-5-yl)indolin-1-yl)(3-fluoropyrrolidin-3-yl)methanone in EtOH (2 ml) was added cyanogen bromide (0.2 mmol) and NaHCO₃ (0.6 mmol). The reaction mixture was stirred at rt for 16 h. The resulting mixture was concentrated under reduced pressure. The crude was purified by preparative reverse phase HPLC (A: 0.078% CH₃COONH₄ in water, B: MeCN) to provide the title compound (39.52 mg, 95.1 tmol). LCMS: Method F, 2.64 min, MS: ES+416.1.

Compounds in Table 1 were synthesised using a procedure similar to that described for Example 35.

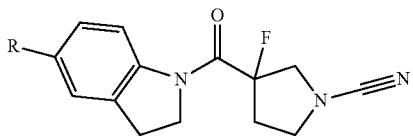

TABLE 1

| Ex | R1 | Name | LCMS Method | LCMS RT (min) | MS ES+ |
|---|---|---|---|---|---|
| 36 | | 3-Fluoro-3-(5-(1-methyl-1H-pyrazol-5-yl)indoline-1-carbonyl)pyrrolidine-1-carbonitrile | D | 3.22 | 340.1 |
| 37 | | 3-Fluoro-3-(5-(4-(4-methylpiperazin-1-yl)phenyl)indoline-1-carbonyl)pyrrolidine-1-carbonitrile | E | 2.40 | 434.1 |
| 38 | | 3-Fluoro-3-(5-(4-(4-methylpiperazine-1-carbonyl)phenyl)indoline-1-carbonyl)pyrrolidine-1-carbonitrile | E | 2.28 | 462.1 |
| 39 | | 3-Fluoro-3-(5-(1-methyl-1H-indazol-5-yl)indoline-1-carbonyl)pyrrolidine-1-carbonitrile | E | 2.98 | 390.1 |
| 40 | | 3-Fluoro-3-(5-(2-fluoro-5-methylphenyl)indoline-1-carbonyl)pyrrolidine-1-carbonitrile | F | 2.94 | 368.1 |
| 41 | | 3-Fluoro-3-(5-(5-methyl-1H-indazol-4-yl)indoline-1-carbonyl)pyrrolidine-1-carbonitrile | F | 2.52 | 390.1 |
| 42 | | N-(3-(1-(1-Cyano-3-fluoropyrrolidine-3-carbonyl)indolin-5-yl)phenyl)cyclopropanesulfonamide | E | 2.90 | 455.0 |
| 43 | | 3-Fluoro-3-(5-(6-methoxypyridin-3-yl)indoline-1-carbonyl)pyrrolidine-1-carbonitrile | E | 2.67 | 367.1 |

Example 44 (R)-1-Cyano-N-(5-(4-cyanophenyl)pyridin-2-yl)-N-ethylpyrrolidine-3-carboxamide

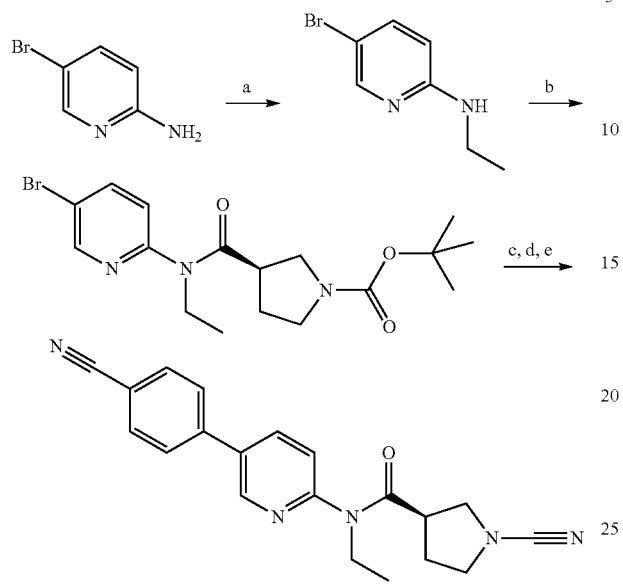

Step a.
To a solution of 5-bromopyridin-2-amine (CAS Number 1072-97-5; 0.6 g, 3.47 mmol) in ethanol (10 ml) was added acetic acid (0.04 g, 0.69 mmol) at 0° C. The resulting reaction mixture was stirred at 0° C. for 2 h. NaCNBH$_3$ (0.27 g, 4.32 mmol) was added to the reaction mixture at 0° C. and stirred at rt for a further 1 h. The resulting reaction mixture was concentrated under reduced pressure, poured into water (20 ml) and extracted with DCM (2×20 ml). The combined organic phase was dried over Na$_2$SO$_4$, filtered and concentrated under reduced pressure. The resulting residue was purified by flash chromatography (10% EtOAc in hexane) yielding 5-bromo-N-ethylpyridin-2-amine (0.35 g, 1.74 mmol). LCMS: Method C, 1.47 min, MS: ES+201.0, 203.0; $^1$H NMR (400 MHz, DMSO-d6) δ ppm 8.00 (d, J=2.4 Hz, 1H), 7.48 (dd, J=2.4 Hz, 8.8 Hz, 1H), 6.71-6.73 (m, 1H), 6.42 (d, J=9.2 Hz, 1H), 3.17-3.24 (m, 2H), 1.10 (t, J=7.2 Hz, 3H).

Step b.
A solution of methyl 5-bromo-N-ethylpyridin-2-amine (0.20 g, 1.00 mmol) and (R)-(–)-N-BOC-pyrrolidine-3-carboxylic acid (CAS Number 72925-16-7; 0.23 g, 1.10 mmol) in DCM was added pyridine (0.869 g, 11.0 mmol) at 0° C. POCl$_3$ (0.612 g, 4.0 mmol) was added to the reaction mixture at 0° C. The reaction mixture was stirred at 0° C. for 30 min. The resulting reaction mixture was poured into saturated NaHCO$_3$ solution (50 ml) and extracted with DCM (2×20 ml). The combined organic phase was dried over Na$_2$SO$_4$, filtered and concentrated under reduced pressure. The resulting residue was purified by flash chromatography (25% EtOAc in hexane) yielding tert-butyl (R)-3-((5-bromopyridin-2-yl)(ethyl)carbamoyl)pyrrolidine-1-carboxylate (0.28 g, 0.705 mmol). LCMS: Method C, 2.49 min, MS: ES+398, 400.

Steps c, d, e.
The title compound was synthesised from the intermediate above using a procedure similar to that described for Example 31, steps b, c, d. LCMS: Method A, 4.04 min, MS: ES+344.98; $^1$H NMR (400 MHz, DMSO-d6) δ ppm 8.94 (d, J=2.4 Hz, 1H), 8.34 (dd, J=2.4 Hz, 8.4 Hz, 1H), 7.98-8.04 (m, 4H), 7.63 (d, J=8.4 Hz, 1H), 3.81-3.88 (m, 2H), 3.41-3.48 (m, 3H), 3.26-3.30 (m, 1H), 3.15-3.18 (m, 1H), 1.93-2.04 (m, 2H), 1.08 (t, J=6.8 Hz, 3H).

Example 45 N-(Benzo[d]thiazol-2-ylmethyl)-1-cyano-N-methylpyrrolidine-3-carboxamide Synthesis According to General Scheme 4

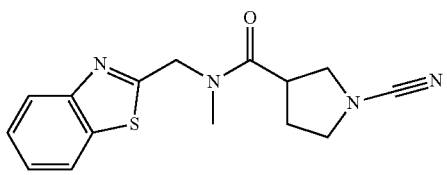 [SMILES: CN(Cc1nc2ccccc2s1)C(=O)C1CCN(C#N)C1]

Step a.
To a solution of 1-(tert-butoxycarbonyl)pyrrolidine-3-carboxylic acid (0.2 mmol) in DCM (1 ml) was added HATU (0.2 mmol). The reaction mixture was stirred at 0° C. for 20 min before addition of 1-(benzo[d]thiazol-2-yl)-N-methylmethanamine (0.2 mmol) and DIPEA (0.6 mmol) at rt. The reaction was stirred for 16 h. The resulting mixture was concentrated under reduced pressure. The residue was purified by prep-TLC (PE:EtOAc=1:2) yielding tert-butyl 3-((benzo[d]thiazol-2-ylmethyl)(methyl)carbamoyl)pyrrolidine-1-carboxylate. MS: ES+376.4.

Step b.
To a solution of tert-butyl 3-((benzo[d]thiazol-2-ylmethyl)(methyl)carbamoyl)pyrrolidine-1-carboxylate in EtOAc (1 ml) was added HCl/EtOAc (4 M, 1 ml). The reaction mixture was stirred at rt for 2 h. The resulting mixture was concentrated under reduced pressure. The residue N-(benzo[d]thiazol-2-ylmethyl)-N-methylpyrrolidine-3-carboxamide was used for next step directly without further purification.

Step c.
To a solution of N-(benzo[d]thiazol-2-ylmethyl)-N-methylpyrrolidine-3-carboxamide in EtOH (2 ml) was added cyanogen bromide (0.2 mmol) and NaHCO$_3$ (0.6 mmol). The reaction mixture was stirred at rt for 16 h. The resulting mixture was concentrated under reduced pressure. The crude was purified by preparative reverse phase HPLC (A: 0.078% CH$_3$COONH$_4$ in water, B: MeCN) to afford N-(benzo[d]thiazol-2-ylmethyl)-1-cyano-N-methylpyrrolidine-3-carboxamide (31.7 mg, 105.5 gmol). LCMS: Method G, 2.64 min, MS: ES+301.1.

Example 46 1-Cyano-N-methyl-N-((3-phenylisoxazol-5-yl)methyl)pyrrolidine-3-carboxamide

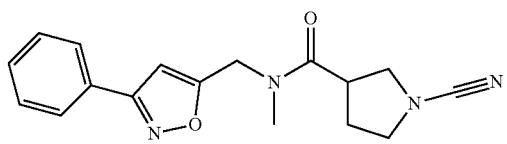 [SMILES: CN(Cc1cc(-c2ccccc2)no1)C(=O)C1CCN(C#N)C1]

Synthesised using a procedure similar to that described for Example 45. LCMS: Method E, 2.51 min, MS: ES+311.1.

Example 47 1-Cyano-N-methyl-N-((2-phenylthiazol-4-yl)methyl)pyrrolidine-3-carboxamide

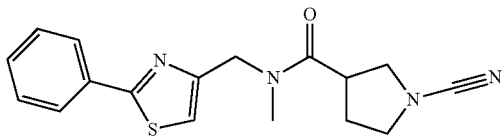 [SMILES: CN(Cc1csc(-c2ccccc2)n1)C(=O)C1CCN(C#N)C1]

Synthesised using a procedure similar to that described for Example 45. LCMS: Method E, 2.69 min, MS: ES+327.0.

Example 48 (cis)-4-Oxo-5-(5-phenylthiazol-2-yl)hexahydropyrrolo[3,4-c]pyrrole-2(1H)-carbonitrile

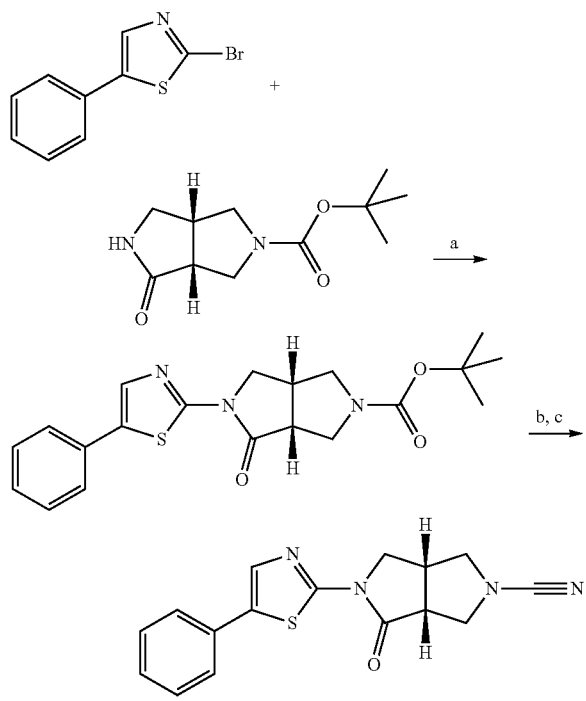

Step a.

To a solution of 2-bromo-5-phenylthiazole (CAS Number 133311-51-0; 0.25 g, 0.84 mmol) in 1,4-dioxane (60 ml) was added cis-4-oxo-hexahydro-pyrrolo[3,4-c]pyrrole-2-carboxylic acid tert-butyl ester (CAS Number-1251003-89-0; 0.17 g, 0.753 mmol), CuI (0.032 g, 0.167 mmol), $K_3PO_4$ (0.709 g, 3.35 mmol) and N,N-dimethylethylenediamine (0.015 g, 0.167 mmol) at rt. The reaction mixture was heated at 100° C. for 4 h. The resulting reaction mixture was poured into water (100 ml) and extracted with EtOAc (2×50 ml). The combined organic phase was dried over $Na_2SO_4$, filtered and concentrated under reduced pressure. The obtained residue was triturated with n-pentane (2×10 ml) and dried over high vacuum to yielding tert-butyl (cis)-4-oxo-5-(5-phenylthiazol-2-yl)hexahydropyrrolo[3,4-c]pyrrole-2(1H)-carboxylate (0.19 g, 0.493 mmol). LCMS: Method C, 2.40 min, MS: ES+386.33. This material was used directly for the next step without further purification.

Steps b, c.

The title compound was synthesised from the intermediate above using a procedure similar to that described for Example 1, steps d, e. LCMS: Method A, 4.15 min, MS: ES+310.93, $^1$H NMR (400 MHz, DMSO-d6) δ ppm 7.97 (s, 1H), 7.65 (d, J=7.2 Hz, 2H), 7.43 (t, J=7.6 Hz, 2H), 7.33 (t, J=7.2 Hz, 1H), 4.16-4.21 (m, 1H), 4.01-4.04 (m, 1H), 3.64-3.73 (m, 3H), 3.55-3.59 (m, 1H), 3.43-3.47 (m, 1H), 3.21-3.25 (m, 1H).

Example 49 7-([1,1'-Biphenyl]-3-yl)-6-oxo-2,7-diazaspiro[4,4]nonane-2-carbonitrile

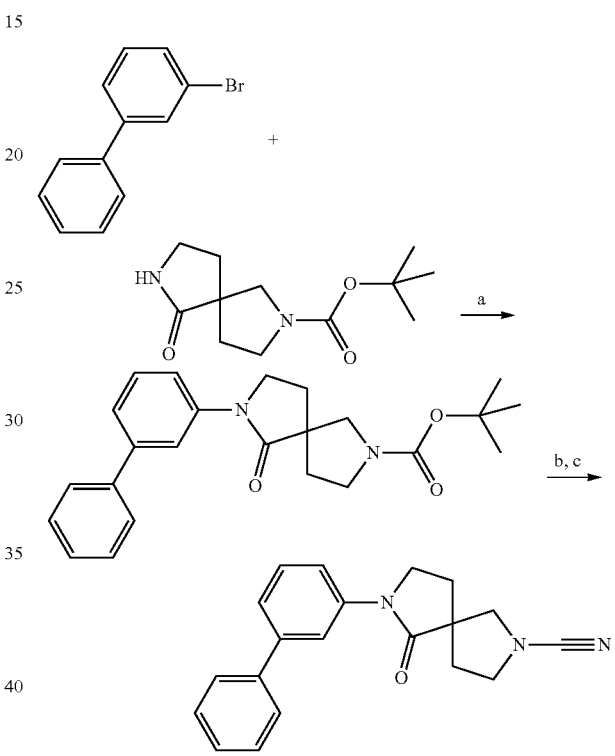

Step a.

To a solution of tert-butyl 6-oxo-2,7-diazaspiro[4.4]nonane-2-carboxylate (CAS Number 1194376-44-7; 0.200 g, 0.83 mmol) in 1,4-dioxane (5 ml) was added 3-bromo-1,1'-biphenyl (CAS Number 2113-57-7; 0.232 g, 0.99 mmol) at rt. Caesium carbonate (0.406 g, 1.25 mmol) was added to the reaction mixture at rt. The resulting reaction mixture was degassed for 15 min before adding Xantphos (0.007 g, 0.012 mmol) and $Pd_2(dba)_3$ (0.011 g, 0.012 mmol) at rt. The resulting reaction mixture was heated at 80° C. for 5 h. The reaction mixture was poured into water (30 ml) and extracted with EtOAc (3×25 ml). The combined organic phase was dried over $Na_2SO_4$, filtered and concentrated under reduced pressure. The residue was purified by flash chromatography (30% EtOAc in hexane) yielding tert-butyl 7-([1,1'-biphenyl]-3-yl)-6-oxo-2,7-diazaspiro[4.4]nonane-2-carboxylate (0.160 g, 0.408 mmol). LCMS: Method B, 5.00 min, MS: ES+337.22 (M−56).

Steps b, c.

The title compound was synthesised from the intermediate above using a procedure similar to that described for Example 1, steps d, e. LCMS: Method B, 4.32 min, MS: ES+318.43; $^1$H NMR (400 MHz, DMSO-d6) δ ppm 7.99 (s, 1H), 7.66-7.70 (m, 3H), 7.45-7.51 (m, 4H), 7.37-7.41 (m, 1H), 3.88-3.98 (m, 2H), 3.35-3.63 (m, 4H), 2.11-2.24 (m, 3H), 1.97-2.09 (m, 1H).

Example 50 (R)-3-(4-(3-Ethylphenyl)indoline-1-carbonyl)pyrrolidine-1-carbonitrile

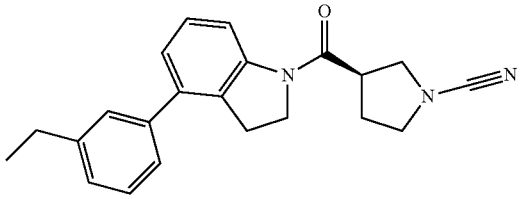 [SMILES: CCc1cccc(-c2cccc3c2CCN3C(=O)[C@@H]2CCN(C#N)C2)c1]

The title compound was synthesised using a procedure similar to that described for Example 10. LCMS: Method A, 5.278 min, MS: ES+346.12; $^1$H NMR (400 MHz, DMSO-d6) δ ppm 8.14 (d, J=8.0 Hz, 1H), 7.35-7.39 (m, 1H), 7.21-7.30 (m, 4H), 7.06 (d, J=8.4 Hz, 1H), 4.16 (t, J=8.4 Hz, 2H), 3.50-3.66 (m, 2H), 3.35-3.48 (m, 3H), 3.20 (t, J=8.4 Hz, 2H), 2.64-2.69 (m, 2H), 2.17-2.25 (m, 1H), 2.02-2.10 (m, 1H), 1.22 (t, J=7.2 Hz, 3H).

Example 51 3-(5-Phenyl-2,3-dihydro-1H-pyrrolo[3,2-b]pyridine-1-carbonyl)pyrrolidine-1-carbonitrile

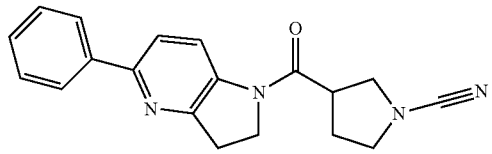 [SMILES: N#CN1CCC(C(=O)N2CCc3nc(-c4ccccc4)ccc32)C1]

The title compound was synthesised using a procedure similar to that described for Example 10. LCMS: Method A, 3.668 min, MS: ES+319.10; $^1$H NMR (400 MHz, DMSO-d6) δ ppm 8.32 (d, J=8.4 Hz, 1H), 8.03 (d, J=7.2 Hz, 2H), 7.78 (d, J=8.4 Hz, 1H), 7.46 (t, J=8.0 Hz, 2H), 7.36-7.40 (m, 1H), 4.26 (t, J=8.8 Hz, 2H), 3.57-3.67 (m, 2H), 3.42-3.52 (m, 3H), 3.32 (t, J=8.8 Hz, 2H), 2.20-2.25 (m, 1H), 2.06-2.11 (m, 1H).

Example 52 Trans-3-methyl-4-(5-phenyl-2,3-dihydro-1H-pyrrolo[2,3-b]pyridine-1-carbonyl)-pyrrolidine-1-carbonitrile

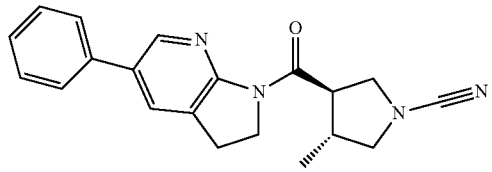 [SMILES: C[C@H]1CN(C#N)C[C@@H]1C(=O)N1CCc2cc(-c3ccccc3)cnc21]

The title compound was synthesised as a racemic mixture using a procedure similar to that described for Example 17, using (3R,4R)-rel-1-(tert-butoxycarbonyl)-4-methylpyrrolidine-3-carboxylic acid (CAS Number 1253791-53-5) in step d. LCMS: Method A, 4.512 min, MS: ES+333.15; $^1$H NMR (400 MHz, DMSO-d6) δ ppm 8.47 (s, 1H), 8.01 (s, 1H), 7.70 (d, J=7.6 Hz, 2H), 7.48 (t, J=8.4 Hz, 2H), 7.37-7.40 (m, 1H), 4.36-4.38 (m, 1H), 4.03-4.09 (m, 2H), 3.80-3.84 (m, 1H), 3.48-3.58 (m, 2H), 3.09-3.14 (m, 3H), 2.55-2.60 (m, 1H), 1.09 (d, J=6.8 Hz, 3H).

Example 53 (S)-3-Fluoro-3-(5-phenylindoline-1-carbonyl)pyrrolidine-1-carbonitrile Example 54 (R)-3-Fluoro-3-(5-phenylindoline-1-carbonyl)pyrrolidine-1-carbonitrile

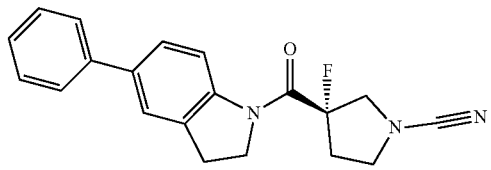

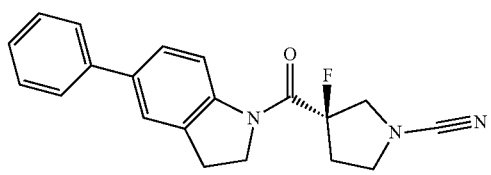

The title compounds were synthesised as a racemic mixture using a procedure similar to that described for Example 35, using 1-(tert-butoxycarbonyl)-3-fluoropyrrolidine-3-carboxylic acid (CAS Number 1001754-59-1) in step a. The enantiomers were separated by preparative chiral SFC; mobile phase: (A) 60% Liquid Carbon dioxide and (B) 40% IPA:MeCN (50:50), column: Chiralcel OX-H 250×21.0 mm, 5 micron, column flow was 70.0 ml/min, ABPR 100 bar, to provide:

Example 53

LCMS: Method A, 4.613 min, MS: ES+336.10; Chiral SFC: Method X, 2.48 min; $^1$H NMR (400 MHz, DMSO-d6) δ ppm 8.13 (d, J=8.4 Hz, 1H), 7.63-7.67 (m, 3H), 7.53 (d, J=8.0 Hz, 1H), 7.43-7.47 (m, 2H), 7.34-7.36 (m, 1H), 4.31-4.35 (m, 2H), 4.00-4.07 (m, 2H), 3.70-3.73 (m, 1H), 3.59-3.62 (m, 1H), 3.24 (t, J=8.0 Hz, 2H), 2.55-2.67 (m, 2H).

Example 54

LCMS: Method A, 4.618 min, MS: ES+336.10; Chiral HPLC: Method X, 3.37 min; $^1$H NMR (400 MHz, DMSO-d6) δ ppm 8.13 (d, J=8.4 Hz, 1H), 7.63-7.67 (m, 3H), 7.53 (d, J=8.0 Hz, 1H), 7.43-7.47 (m, 2H), 7.34-7.36 (m, 1H), 4.31-4.35 (m, 2H), 4.00-4.07 (m, 2H), 3.70-3.73 (m, 1H), 3.59-3.62 (m, 1H), 3.24 (t, J=8.0 Hz, 2H), 2.55-2.67 (m, 2H).

Example 55 (S)-3-(5-(3-Chlorophenyl)-2,3-dihydro-1H-pyrrolo[2,3-b]pyridine-1-carbonyl)-3-fluoropyrrolidine-1-carbonitrile Example 56 (R)-3-(5-(3-Chlorophenyl)-2,3-dihydro-1H-pyrrolo[2,3-b]pyridine-1-carbonyl)-3-fluoropyrrolidine-1-carbonitrile

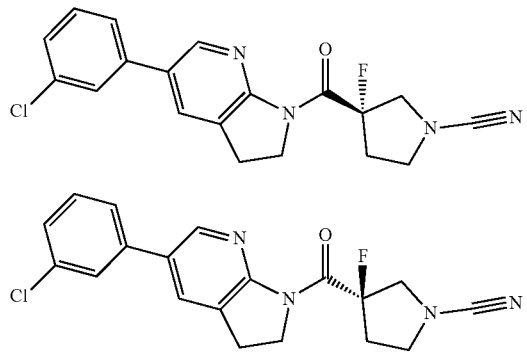

The title compounds were synthesised as a racemic mixture using a procedure similar to that described for Example 17, using 1-(tert-butoxycarbonyl)-3-fluoropyrrolidine-3-carboxylic acid (CAS Number 1001754-59-1) in step d. The enantiomers were separated by preparative chiral SFC; mobile phase: (A) 80% Liquid Carbon dioxide and (B) 20% IPA:MeCN (50:50), column: Chiralpak AD-H 250×21.0 mm, 5 micron, column flow was 80.0 ml/min, ABPR 100 bar, to provide:

Example 55

LCMS: Method A, 4.332 min, MS: ES+371.10; Chiral SFC: Method Y, 4.63 min; $^1$H NMR (400 MHz, DMSO-d6) δ ppm 8.53 (s, 1H), 8.07 (s, 1H), 7.79 (s, 1H), 7.67-7.69 (m, 1H), 7.44-7.52 (m, 2H), 4.12-4.27 (m, 4H), 3.72-3.74 (m, 1H), 3.60-3.62 (m, 1H), 3.15-3.19 (m, 2H), 2.67-2.85 (m, 2H).

Example 56

LCMS: Method A, 4.340 min, MS: ES+371.10; Chiral SFC: Method Y, 7.02 min; $^1$H NMR (400 MHz, DMSO-d6) δ ppm 8.53 (s, 1H), 8.07 (s, 1H), 7.79 (s, 1H), 7.67-7.69 (m, 1H), 7.44-7.52 (m, 2H), 4.12-4.27 (m, 4H), 3.72-3.74 (m, 1H), 3.60-3.62 (m, 1H), 3.15-3.19 (m, 2H), 2.67-2.85 (m, 2H).

Example 57 3-Fluoro-3-(5-(pyridin-3-yl)indoline-1-carbonyl)pyrrolidine-1-carbonitrile

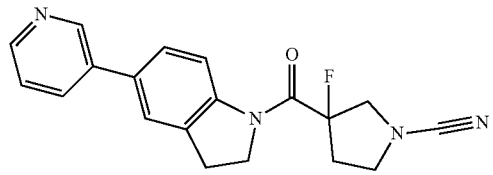 [SMILES: N#CN1CCC(F)(C(=O)N2CCc3cc(-c4cccnc4)ccc32)C1]

The title compound was synthesised as a racemic mixture using a procedure similar to that described for Example 35, using 1-(tert-butoxycarbonyl)-3-fluoropyrrolidine-3-carboxylic acid (CAS Number 1001754-59-1) in step a. LCMS: Method A, 3.428 min, MS: ES+337.10; $^1$H NMR (400 MHz, DMSO-d6) δ ppm 8.89 (s, 1H), 8.54-8.55 (m, 1H), 8.16 (d, J=8.4 Hz, 1H), 8.07 (d, J=8.0 Hz, 1H), 7.71 (s, 1H), 7.61 (d, J=8.8 Hz, 1H), 7.35-7.48 (m, 1H), 4.32-4.35 (m, 2H), 4.00-4.11 (m, 2H), 3.70-3.74 (m, 1H), 3.57-3.63 (m, 1H), 3.25 (t, J=8.0 Hz, 2H), 2.58-2.68 (m, 2H).

Example 58 3-Fluoro-3-(5-(1-isobutyl-1H-pyrazol-5-yl)indoline-1-carbonyl)pyrrolidine-1-carbonitrile

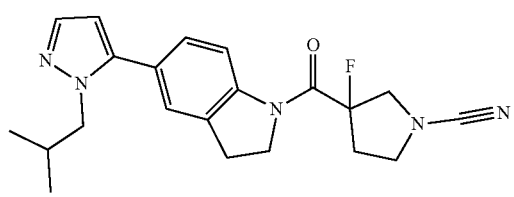 [SMILES: CC(C)Cn1nccc1-c1ccc2c(c1)CCN2C(=O)C1(F)CCN(C#N)C1]

The title compound was synthesised using a procedure similar to that described for Example 57. LCMS: Method A, 4.170 min, MS: ES+382.15; $^1$H NMR (400 MHz, DMSO-d6) δ ppm 8.14 (d, J=8.0 Hz, 1H), 7.49 (s, 1H), 7.39 (s, 1H), 7.31 (d, J=8.0 Hz, 1H), 6.31 (d, J=1.6 Hz, 1H), 4.31-4.34 (m, 2H), 3.93-4.07 (m, 5H), 3.70-3.71 (m, 1H), 3.59-3.61 (m, 1H), 3.16-3.25 (m, 2H), 1.99-2.03 (m, 2H), 0.68 (d, J=6.8 Hz, 6H).

Example 59 3-(5-(1-Benzyl-1H-pyrazol-4-yl)indoline-1-carbonyl)-3-fluoropyrrolidine-1-carbonitrile

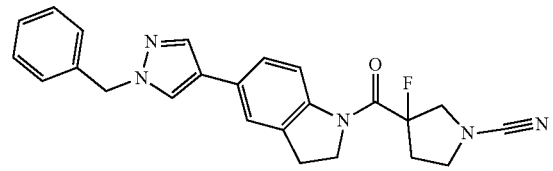 [SMILES: N#CN1CCC(F)(C(=O)N2CCc3cc(-c4cnn(Cc5ccccc5)c4)ccc32)C1]

The title compound was synthesised using a procedure similar to that described for Example 57. LCMS: Method A, 4.152 min, MS: ES+416.15; $^1$H NMR (400 MHz, DMSO-d6) δ ppm 8.24 (s, 1H), 8.03 (d, J=8.4 Hz, 1H), 7.89 (s, 1H), 7.52 (s, 1H), 7.43 (d, J=8.0 Hz, 1H), 7.26-7.37 (m, 5H), 5.33 (s, 2H), 4.27-4.30 (m, 2H), 3.97-4.09 (m, 2H), 3.68-3.73 (m, 1H), 3.55-3.62 (m, 1H), 3.15-3.19 (m, 2H), 2.54-2.66 (m, 2H).

Example 60 (S)-3-(5-(1H-indazol-4-yl)-2,3-dihydro-1H-pyrrolo[2,3-b]pyridine-1-carbonyl)-pyrrolidine-1-carbonitrile Synthesis According to General Scheme 3

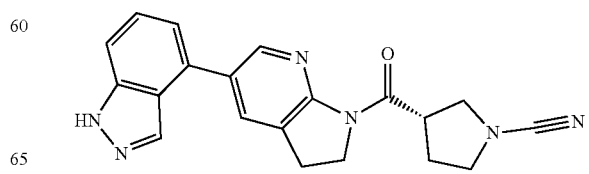

Step a.

To a solution of (S)-1-(tert-butoxycarbonyl)pyrrolidine-3-carboxylic acid (CAS Number 140148-70-5; 0.500 g, 2.32 mmol) in DCM (25 ml) was added DIPEA (0.65 ml, 3.87 mmol) and HBTU (1.1 g, 2.91 mmol) at rt. The reaction mixture was stirred at rt for 30 min before addition of 5-bromo-2,3-dihydro-1H-pyrrolo[2,3-b]pyridine (CAS Number 115170-40-6; 0.383 g, 1.94 mmol) at rt. The reaction mixture was stirred at rt for 6 h. The resulting mixture was poured into saturated NaHCO₃ solution (50 ml) and extracted with EtOAc (3×15 ml). The combined organic phase was washed with brine solution (2×20 ml), dried over Na₂SO₄, filtered and concentrated under reduced pressure. The resulting residue was purified by column chromatography (40-50% EtOAc in n-hexane) yielding tert-butyl (S)-3-(5-bromo-2,3-dihydro-1H-pyrrolo[2,3-b]pyridine-1-carbonyl)pyrrolidine-1-carboxylate (0.600 g, 1.515 mmol). LCMS: Method C, 2.370 min, MS: ES+396.38, 398.38

Step b.

To a stirred solution of tert-butyl (S)-3-(5-bromo-2,3-dihydro-1H-pyrrolo[2,3-b]pyridine-1-carbonyl)pyrrolidine-1-carboxylate (0.400 g, 1.013 mmol) in 1,4-dioxane:water (9:1, 25 ml) was added Cs₂CO₃ (0.998 g, 3.073 mmol) and indazole-4-boronic acid pinacol ester (CAS Number 885618-33-7; 0.300 g, 1.23 mmol) at rt. The reaction mixture was degassed for 20 min before addition of PdCl₂(dppf) (0.075 g, 0.102 mmol) at rt. The resulting reaction mixture was heated at 100° C. for 8 h. The resulting mixture was poured into saturated NaHCO₃ solution (50 ml) and extracted with EtOAc (3×20 ml). The combined organic phase was washed with brine solution (2×25 ml), dried over Na₂SO₄, filtered and concentrated under reduced pressure. The resulting residue was purified by column chromatography (65-70% EtOAc in n-hexane) yielding tert-butyl (S)-3-(5-(1H-indazol-4-yl)-2,3-dihydro-1H-pyrrolo[2,3-b]pyridine-1-carbonyl) pyrrolidine-1-carboxylate (0.350 g, 0.808 mmol). LCMS: Method C, 2.040 min, MS: ES+434.63

Steps c, d.

The title compound was synthesised from the intermediate above using a procedure similar to that described for Example 35, steps c, d. LCMS: Method A, 3.257 min, MS: ES+359.10; Chiral SFC: Method Z, 6.07 min; ¹H NMR (400 MHz, DMSO-d6) δ ppm 13.28 (s, 1H), 8.47 (s, 1H), 8.23 (s, 1H), 8.05 (s, 1H), 7.57 (d, J=8.0 Hz, 1H), 7.44 (t, J=8.0 Hz, 1H), 7.26 (d, J=6.8 Hz, 1H), 4.63-4.67 (m, 1H), 4.08 (t, J=8.4 Hz, 2H), 3.70-3.74 (m, 1H), 3.56-3.60 (m, 1H), 3.45-3.49 (m, 2H), 3.17 (t, J=8.4 Hz, 2H), 2.21-2.29 (m, 1H), 2.07-2.15 (m, 1H).

Example 61 (R)-3-(5-(1H-Indazol-4-yl)-2,3-dihydro-1H-pyrrolo[2,3-b]pyridine-1-carbonyl)-pyrrolidine-1-carbonitrile

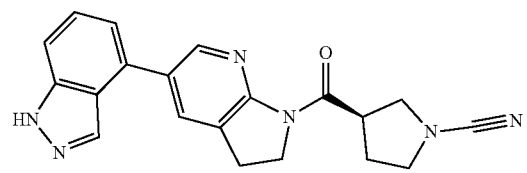 [SMILES: N#CN1CC[C@@H](C(=O)N2CCc3cc(-c4cccc5[nH]ncc45)cnc32)C1]

The title compound was synthesised using a procedure similar to that described for Example 60. LCMS: Method A, 3.239 min, MS: ES+359.15; Chiral SFC: Method Z, 5.22 min; ¹H NMR (400 MHz, DMSO-d6) δ ppm 13.28 (s, 1H), 8.47 (s, 1H), 8.23 (s, 1H), 8.05 (s, 1H), 7.57 (d, J=8.0 Hz, 1H), 7.44 (t, J=8.0 Hz, 1H), 7.26 (d, J=6.8 Hz, 1H), 4.63-4.67 (m, 1H), 4.08 (t, J=8.4 Hz, 2H), 3.70-3.74 (m, 1H), 3.56-3.60 (m, 1H), 3.45-3.49 (m, 2H), 3.17 (t, J=8.4 Hz, 2H), 2.21-2.29 (m, 1H), 2.07-2.15 (m, 1H).

Example 62 3-Fluoro-3-(5-(1-(pyridin-2-ylmethyl)-1H-pyrazol-5-yl)indoline-1-carbonyl)pyrrolidine-1-carbonitrile

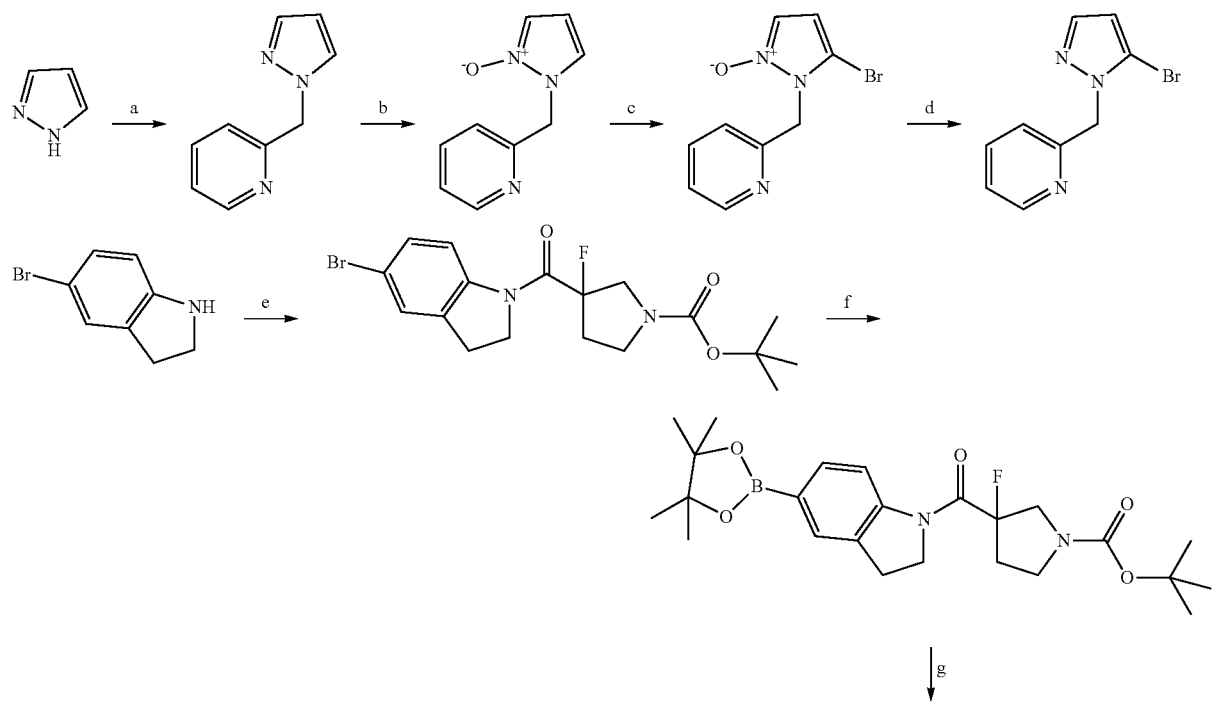

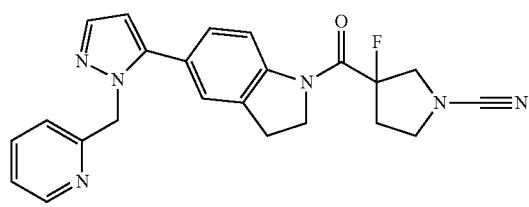 ← h, i 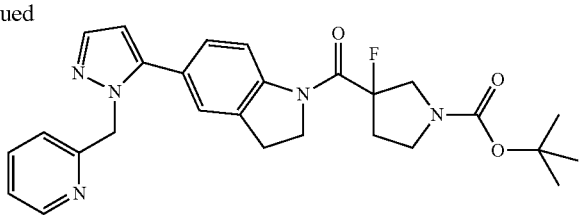

Step a.

To a solution of 1H-pyrazole (0.456 g, 6.70 mmol) in DMF (5 ml) was added $K_2CO_3$ (4.200 g, 30.43 mmol) and 2-chloromethylpyridine HCl (1.00 g, 6.10 mmol) at rt. The reaction mixture was stirred at rt for 16 h. The resulting mixture was poured into water (50 ml) and extracted with EtOAc (3×70 ml). The combined organic phase was washed with cold water (2×50 ml), dried over $Na_2SO_4$, filtered and concentrated under reduced pressure, yielding 2-((1H-pyrazol-1-yl)methyl)pyridine (1.400 g, 8.805 mmol). This material was directly used for next step without any further purification. LCMS: Method C, 1.190 min, MS: ES+160.27

Step b.

To a solution of 2-((1H-pyrazol-1-yl) methyl) pyridine (1.300 g, 8.17 mmol) in DCM (10 ml) was added urea hydrogen peroxide (CAS Number 124-43-6; 1.610 g, 17.11 mmol) at rt. The reaction mixture was cooled to 0° C. Trifluoroacetic anhydride (3.430 g, 16.33 mmol) was drop wise added to the reaction mixture at 0° C. The reaction mixture was stirred at rt for 16 h. The resulting mixture was poured into saturated $Na_2SO_3$ solution (70 ml) and extracted with DCM (3×100 ml). The combined organic phase was dried over $Na_2SO_4$, filtered and concentrated under reduced pressure yielding 1-(pyridin-2-ylmethyl)-1H-pyrazole 2-oxide (0.955 g, 5.457 mmol). This material was directly used for next step without any further purification. LCMS: Method C, 1.041, MS: ES+176.23

Step c.

To a solution of 1-(pyridin-2-ylmethyl)-1H-pyrazole 2-oxide (0.850 g, 4.86 mmol) in DCM (3 ml) was added $K_2CO_3$ (1.340 g, 9.71 mmol) at rt. The reaction mixture was cooled to −78° C. A solution of bromine (0.77 g, 4.86 mmol) in DCM (2 ml) was added dropwise to the reaction mixture at −78° C. The reaction mixture was stirred at −78° C. for 15 min and further stirred at 0° C. for 1 h. The resulting mixture was poured into saturated $Na_2SO_3$ solution (50 ml) and extracted with DCM (3×70 ml). The combined organic phase was dried over $Na_2SO_4$, filtered and concentrated under reduced pressure. The resulting residue was purified by column chromatography (3.5% MeOH in DCM) yielding 5-bromo-1-(pyridin-2-ylmethyl)-1H-pyrazole 2-oxide (0.340 g, 1.34 mmol). This material was directly used for next step without any further purification. LCMS: Method C, 1.407, MS: ES+254.23, 256.23

Step d.

To a solution of 5-bromo-1-(pyridin-2-ylmethyl)-1H-pyrazole 2-oxide (0.310 g, 1.22 mmol) in DCM (3 ml) was added a solution of $PCl_3$ (0.370 g, 2.69 mmol) in DCM (2 ml) at 0° C. The reaction mixture was stirred at 0° C. for 1 h and then heated to 50° C. for 4 h. The resulting mixture was poured into saturated solution of sodium acetate in methanol (50 ml). The resulting mixture was concentrated under reduced pressure. The resulting residue was poured into water (50 ml) and extracted in EtOAc (3×70 ml). The combined organic phase was dried over $Na_2SO_4$, filtered and concentrated under reduced pressure yielding 2-((5-bromo-1H-pyrazol-1-yl) methyl) pyridine (0.320 g, 1.35 mmol). This material was directly used for next step without any further purification. LCMS: Method C, 1.554, MS: ES+238.30, 240.30

Step e.

To a solution of 5-bromoindoline (5.000 g, 25.24 mmol) in DMF (25 ml) was added 1-(tert-butoxycarbonyl)-3-fluoropyrrolidine (CAS Number 1001754-59-1; 5.860 g, 25.26 mmol) at 0° C. The reaction mixture was then treated with HATU (14.30 g, 37.63 mmol) and DIPEA (9.78 g, 75.6 mmol) at 0° C. The reaction mixture was stirred at 0° C. for 10-15 min and then at rt for a further 2 h. The resulting mixture was poured into ice-cold water (150 ml). The resulting precipitates were collected by filtration and washed with water (3×50 ml). The obtained solid material was dried under high vacuum yielding tert-butyl 3-(5-bromoindoline-1-carbonyl)-3-fluoropyrrolidine-1-carboxylate (10.00 g, 24.27 mmol). This material was directly used for next step without any further purification. LCMS: Method C, 2.510, MS: ES+413.40, 415.40

Step f.

To a solution of tert-butyl 3-(5-bromoindoline-1-carbonyl)-3-fluoropyrrolidine-1-carboxylate (1.000 g, 2.43 mmol) and bis(pinacolato)diboron (0.801 g, 3.15 mmol) in 1,4-dioxane (5 ml) was added KOAc (0.715 g, 7.28 mmol) at rt. The reaction mixture was degassed for 15 min before addition of $PdCl_2(dppf)$ (0.177 g, 0.242 mmol) at rt. The reaction mixture was heated at 95° C. for 1 h. The resulting mixture was cooled to rt, poured into water (70 ml) and extracted with EtOAc (3×100 ml). The combined organic phase was dried over $Na_2SO_4$, filtered and concentrated under reduced pressure yielding tert-butyl 3-fluoro-3-(5-(4,4,5,5-tetramethyl-1,3,2-dioxaborolan-2-yl)indoline-1-carbonyl)-pyrrolidine-1-carboxylate (1.80 g, quantitative yield). This material wasused directly in the next step without any further purification. LCMS: Method C, 2.677, MS: ES+461.60

Step g.

To a solution of 2-((5-bromo-1H-pyrazol-1-yl)methyl) pyridine (step d; 0.300 g, 1.27 mmol) and tert-butyl 3-fluoro-3-(5-(4,4,5,5-tetramethyl-1,3,2-dioxaborolan-2-yl) indoline-1-carbonyl)-pyrrolidine-1-carboxylate (0.699 g, 1.52 mmol) in DMF:water (9:1, 5 ml) was added $K_2CO_3$ (0.349 g, 2.53 mmol) at rt. The reaction mixture was degassed for 15 min before addition of $PdCl_2(dppf)$ (0.046 g, 0.062 mmol) at rt. The reaction mixture was heated at 110° C. for 1 h. The resulting mixture was poured into water (40 ml) and extracted with EtOAc (3×50 ml). The combined organic phase was washed with ice cold water (2×50 ml), dried over $Na_2SO_4$, filtered and concentrated under reduced pressure. The obtained residue was purified by flash column chromatography (3% MeOH in DCM) yielding tert-butyl 3-fluoro-3-(5-(1-(pyridin-2-ylmethyl)-1H-pyrazol-5-yl)indoline-1-carbonyl)-pyrrolidine-1-carboxylate (0.300 g, 0.610 mmol). LCMS: Method C, 2.070, MS: ES+492.70

Steps h, i.

The title compound was synthesised from the intermediate above using a procedure similar to that described for Example 1, steps d, e. LCMS: Method A, 3.377 min, MS: ES+417.15; $^1$H NMR (400 MHz, DMSO-d6) δ ppm 8.55 (d, J=4.4 Hz, 1H), 8.28 (s, 1H), 8.04 (d, J=8.4 Hz, 1H), 7.92 (s, 1H), 7.79 (t, J=7.6 Hz, 1H), 7.55 (s, 1H), 7.45 (d, J=8.0 Hz, 1H), 7.31-7.34 (m, 1H), 7.11 (d, J=7.6 Hz, 1H), 5.44 (s, 2H), 4.27-4.29 (m, 2H), 3.98-4.09 (m, 2H), 3.69-3.73 (m, 1H), 3.58-3.62 (m, 1H), 3.18 (t, J=8.0 Hz, 2H), 2.54-2.67 (m, 2H).

Example 63 3-Fluoro-3-(5-(1-(pyridin-3-ylmethyl)-H-pyrazol-5-yl)indoline-1-carbonyl)pyrrolidine-1-carbonitrile

The title compound was synthesised using a procedure similar to that described for Example 62. LCMS: Method A, 3.236 min, MS: ES+417.15; $^1$H NMR (400 MHz, DMSO-d6) δ ppm 8.55 (d, J=1.2 Hz, 1H), 8.51-8.52 (m, 1H), 8.30 (s, 1H), 8.03 (d, J=8.4 Hz, 1H), 7.92 (s, 1H), 7.69 (d, J=7.6 Hz, 1H), 7.37-7.44 (m, 3H), 5.39 (s, 2H), 4.27-4.30 (m, 2H), 3.98-4.09 (m, 2H), 3.68-3.73 (m, 1H), 3.55-3.62 (m, 1H), 3.18 (t, J=8.0 Hz, 2H), 2.53-2.62 (m, 2H).

Example 64 3-(5-(1-(2-Chlorobenzyl)-1H-pyrazol-5-yl)indoline-1-carbonyl)-3-fluoropyrrolidine-1-carbonitrile

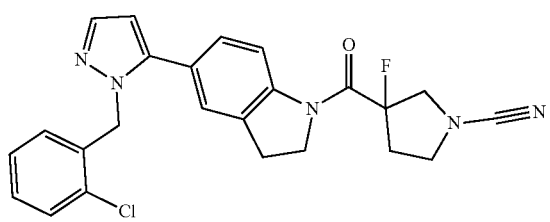 [SMILES: N#CN1CCC(F)(C(=O)N2CCc3cc(-c4ccnn4Cc4ccccc4Cl)ccc32)C1]

The title compound was synthesised using a procedure similar to that described for Example 62. LCMS: Method A, 4.373 min, MS: ES+450.10; $^1$H NMR (400 MHz, DMSO-d6) δ ppm 8.08 (d, J=8.4 Hz, 1H), 7.61 (d, J=1.6 Hz, 1H), 7.43-7.45 (m, 1H), 7.35 (s, 1H), 7.24-7.32 (m, 3H), 6.69-6.72 (m, 1H), 6.48 (d, J=2.0 Hz, 1H), 5.44 (s, 2H), 4.28-4.32 (m, 2H), 3.97-4.08 (m, 2H), 3.67-3.73 (m, 1H), 3.55-3.62 (m, 1H), 3.17 (t, J=8.0 Hz, 2H), 2.53-2.68 (m, 2H).

Example 65 3-(5-(1-(3-Chlorobenzyl)-1H-pyrazol-5-yl)indoline-1-carbonyl)-3-fluoropyrrolidine-1-carbonitrile

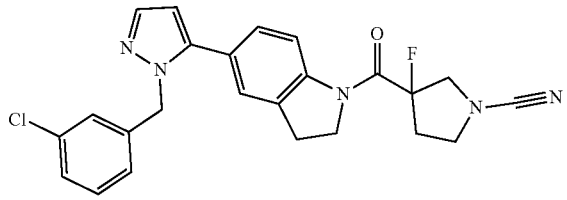 [SMILES: N#CN1CCC(F)(C(=O)N2CCc3cc(-c4ccnn4Cc4cccc(Cl)c4)ccc32)C1]

The title compound was synthesised using a procedure similar to that described for Example 62. LCMS: Method A, 4.454 min, MS: ES+450.15; $^1$H NMR (400 MHz, DMSO-d6) δ ppm 8.09 (d, J=8.4 Hz, 1H), 7.60 (d, J=1.6 Hz, 1H), 7.31-7.34 (m, 3H), 7.25 (d, J=8.4 Hz, 1H), 7.02 (s, 1H), 6.90-6.92 (m, 1H), 6.45 (d, J=1.6 Hz, 1H), 5.40 (s, 2H), 4.29-4.33 (m, 2H), 3.98-4.09 (m, 2H), 3.68-3.73 (m, 1H), 3.55-3.62 (m, 1H), 3.19 (t, J=8.4 Hz, 2H), 2.54-2.66 (m, 2H).

Example 66 3-(5-(1-(4-Chlorobenzyl)-1H-pyrazol-5-yl)indoline-1-carbonyl)-3-fluoropyrrolidine-1-carbonitrile

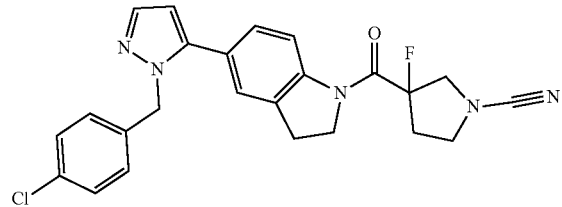 [SMILES: N#CN1CCC(F)(C(=O)N2CCc3cc(-c4ccnn4Cc4ccc(Cl)cc4)ccc32)C1]

The title compound was synthesised using a procedure similar to that described for Example 62. LCMS: Method A, 4.422 min, MS: ES+450.15; $^1$H NMR (400 MHz, DMSO-d6) δ ppm 8.09 (d, J=8.4 Hz, 1H), 7.58 (d, J=1.6 Hz, 1H), 7.34-7.36 (m, 3H), 7.25 (d, J=8.4 Hz, 1H), 7.00 (d, J=8.0 Hz, 2H), 6.44 (d, J=1.6 Hz, 1H), 5.38 (s, 2H), 4.29-4.32 (m, 2H), 3.98-4.09 (m, 2H), 3.68-3.73 (m, 1H), 3.56-3.62 (m, 1H), 3.19 (t, J=8.4 Hz, 2H), 2.54-2.69 (m, 2H).

Example 67 N-Benzyl-1-(1-cyano-3-fluoropyrrolidine-3-carbonyl)indoline-5-carboxamide

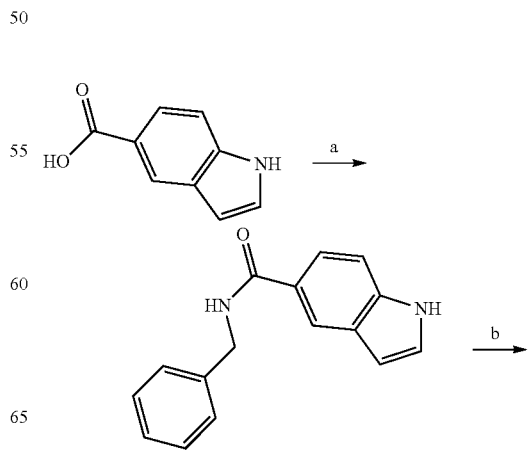

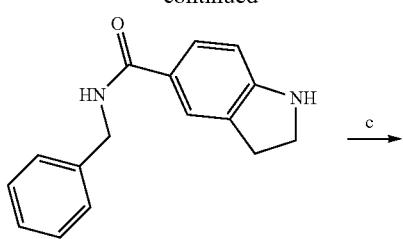

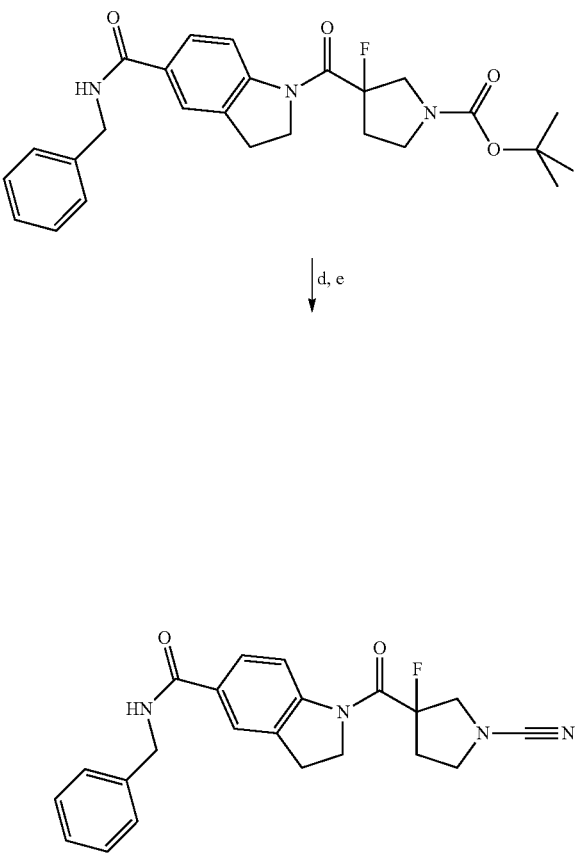

Step a.

To a solution of 1H-indole-5-carboxylic acid (CAS Number 1670-81-1; 0.700 g, 4.35 mmol) in DMF (10 ml) was added HATU (3.300 g, 8.68 mmol) at rt. The reaction mixture was stirred at rt for 10 min before addition of phenylmethanamine (0.930 g, 8.695 mmol) and DIPEA (2.22 g, 13.0 mmol) at rt. The reaction mixture was stirred at rt for 1 h. The resulting mixture was poured into ice-cold water (150 ml) and extracted with EtOAc (3×100 ml). The combined organic phase was dried over $Na_2SO_4$, filtered and concentrated under reduced pressure. The resulting residue was purified by column chromatography (50% EtOAc in hexane) yielding N-benzyl-1H-indole-5-carboxamide (0.600 g, 2.40 mmol). LCMS: Method C, 1.846 min, MS: ES+251.3

Step b.

To a solution of N-benzyl-1H-indole-5-carboxamide (0.600 g, 2.40 mmol) in glacial acetic acid (15 ml) was portion wise added $NaCNBH_3$ (0.452 g, 7.19 mmol) at 0° C. The reaction mixture was stirred at rt for 2 h. The resulting mixture was basified with saturated $NaHCO_3$ solution and extracted with DCM (2×100 ml). The combined organic phase was dried over $Na_2SO_4$, filtered and concentrated under reduced pressure. The resulting residue was purified by column chromatography (70% EtOAc in hexane) yielding N-benzylindoline-5-carboxamide (0.350 g, 1.388 mmol). LCMS: Method C, 1.543 min, MS: ES+253.40

Step c.

To a mixture of N-benzylindoline-5-carboxamide (0.100 g, 0.396 mmol), 1-(tert-butoxycarbonyl)-3-fluoropyrrolidine-3-carboxylic acid (CAS Number 1001754-59-1; 0.138 g, 0.595 mmol) and DCC (0.163 g, 0.793 mmol) in a microwave tube was added DMF (4 drops). The reaction mixture was irradiated under microwave at 150° C. for 30 min. The resulting mixture was diluted with EtOAc (25 ml), and precipitates were removed by filtration, washing with EtOAc (25 ml). The combined filtrate was washed with water (70 ml) and brine (100 ml). The combined organic phase was dried over $Na_2SO_4$, filtered and concentrated under reduced pressure. The resulting residue was purified by column chromatography (80% EtOAc in hexane) yielding tert-butyl 3-(5-(benzylcarbamoyl)-indoline-1-carbonyl)-3-fluoropyrrolidine-1-carboxylate (0.18 g, quantitative yield). LCMS: Method C, 2.167 min, MS: ES+468.64

Steps d, e.

The title compound was synthesised from the intermediate above using a procedure similar to that described for Example 1, steps d, e. LCMS: Method A, 3.639 min, MS: ES+393.15; $^1$H NMR (400 MHz, DMSO-d6) δ ppm 8.98 (t, J=6.0 Hz, 1H), 8.09 (d, J=8.8 Hz, 1H), 7.83 (s, 1H), 7.79 (d, J=8.4 Hz, 1H), 7.31-7.35 (m, 4H), 7.22-7.26 (m, 1H), 4.47 (d, J=6.0 Hz, 2H), 4.31-4.34 (m, 2H), 3.98-4.01 (m, 2H), 3.68-3.73 (m, 1H), 3.56-3.62 (m, 1H), 3.21 (t, J=8.0 Hz, 2H), 2.55-2.67 (m, 2H).

Example 68 (R)-1-(1-Cyanopyrrolidine-3-carbonyl)-4-(3-ethylphenyl)-N-methylindoline-6-carboxamide

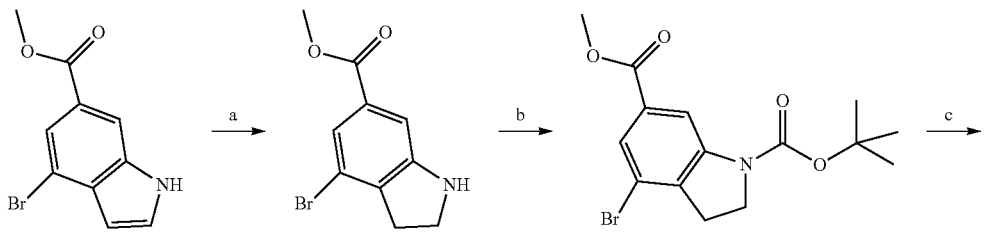

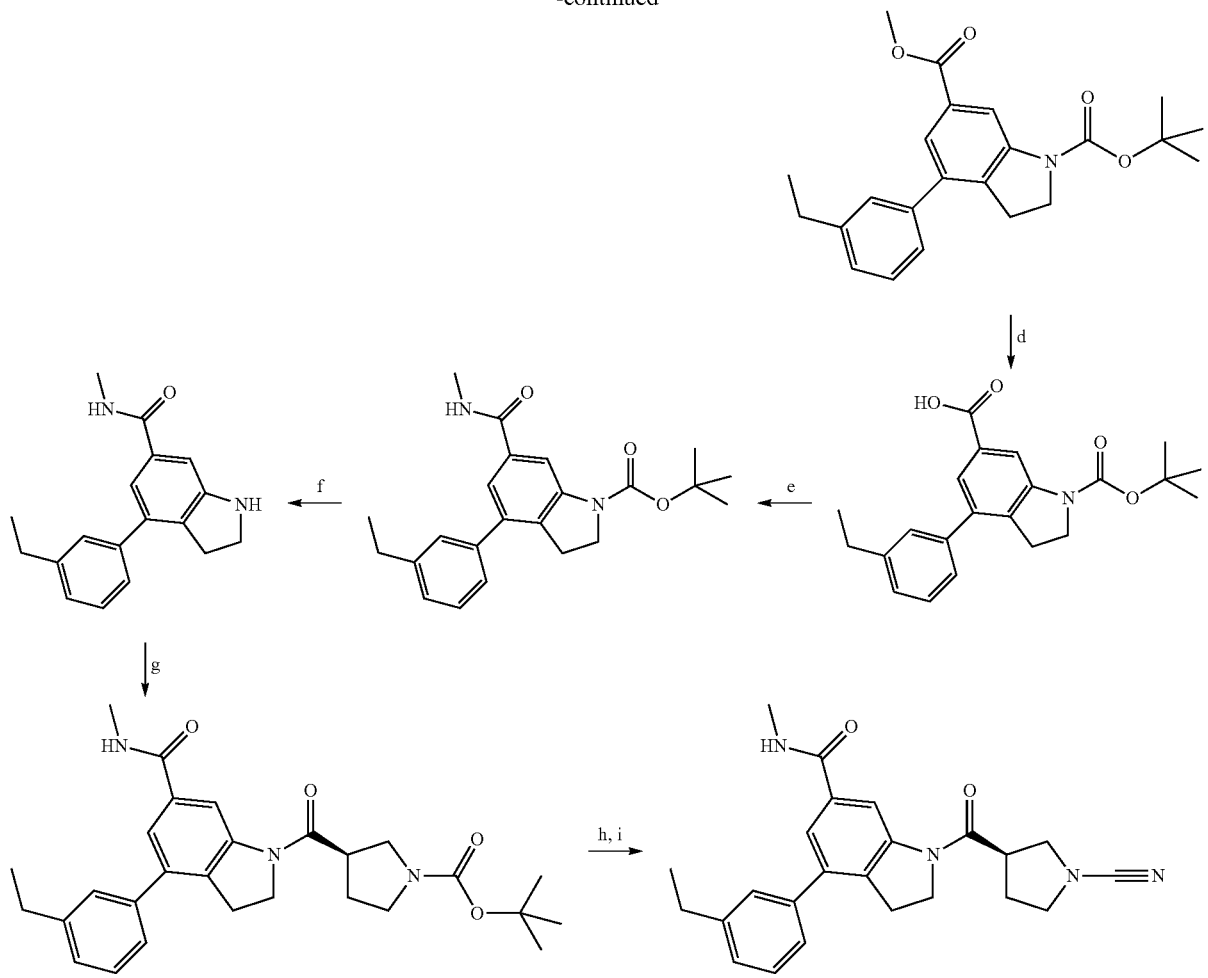

Step a.

To a solution of methyl 4-bromo-1H-indole-6-carboxylate (CAS Number 882679-96-1; 3.000 g, 11.86 mmol) in TFA (14 ml) was added triethylsilane (4.13 g, 35.6 mmol) dropwise at rt. The reaction mixture was heated at 60° C. for 1 h. The resulting mixture was evaporated under vacuum. The resulting residue was diluted with saturated NaHCO$_3$ solution (150 ml) and extracted with EtOAc (2×100 ml). The combined organic phase was washed with brine solution (75 ml), dried over Na$_2$SO$_4$, filtered and concentrated under reduced pressure to yielding methyl 4-bromoindoline-6-carboxylate as thick yellow oil (2.40 g, 9.37 mmol). This material was used directly in next step without further purification. LCMS: Method C, 2.209 min, MS: ES+256.21; 258.21

Step b.

To a solution of methyl 4-bromoindoline-6-carboxylate (2.40 g, 9.37 mmol) in THF (20 ml) were added TEA (1.14 ml, 11.3 mmol) followed by BOC-anhydride (2.46 g, 11.3 mmol) at rt. The reaction mixture was stirred at rt for 16 h. The reaction mixture was poured into water (100 ml) and extracted with EtOAc (2×100 ml). The combined organic phase was collected, dried over Na$_2$SO$_4$, filtered and concentrated under reduced pressure. The crude material was purified by column chromatography (5-7% EtOAc in hexane) yielding 1-(tert-butyl) 6-methyl 4-bromoindoline-1,6-dicarboxylate (3.00 g, 8.42 mmol). LCMS: Method C, 2.846 min, MS: ES+373.39, 375.39 [M+18].

Step c.

To a stirred solution of 1-(tert-butyl) 6-methyl 4-bromoindoline-1,6-dicarboxylate (1.000 g, 2.82 mmol) and 3-ethylphenylboronic acid (CAS Number 90555-65-0; 0.630 g, 4.22 mmol) in 1,4-dioxane:water (9:1, 10 ml) was added Na$_2$CO$_3$ (0.298 g, 8.45 mmol) at rt. The reaction mixture was degassed for 15 min before addition of PdCl$_2$(dppf) (0.210 g, 0.28 mmol) at rt. The reaction mixture was heated at 100° C. for 2 h then cooled to rt and poured into water (100 ml). The resulting mixture was extracted with EtOAc (2×100 ml). The combined organic phase was washed with brine solution (50 ml), dried over Na$_2$SO$_4$, filtered and concentrated under reduced pressure. The obtained residue was purified by flash column chromatography (2% MeOH in DCM) yielding 1-(tert-butyl) 6-methyl 4-(3-ethylphenyl)indoline-1,6-dicarboxylate (0.800 g, 2.10 mmol). LCMS: Method C, 3.314 min, MS: ES+399.30 [M+18]

Step d.

To a solution of 1-(tert-butyl) 6-methyl 4-(3-ethylphenyl)indoline-1,6-dicarboxylate (0.760 g 1.99 mmol) in THF:water:MeOH (1:1:0.15, 15 ml) was added NaOH (0.240 g, 5.98 mmol) at rt. The reaction mixture was heated at 100° C. for 5 h. The resulting reaction mixture was cooled to rt, diluted with water (50 ml) and extracted with EtOAc (50 ml). The resulting aqueous layer was acidified by 1M HCl (75 ml) and extracted with EtOAc (2×80 ml). The combined organic phase was washed with brine solution (70 ml), dried over Na$_2$SO$_4$, filtered and concentrated under reduced pressure yielding 1-(tert-butoxycarbonyl)-4-(3-ethylphenyl)indoline-6-carboxylic acid (0.650 g, 1.77 mmol). LCMS: Method C, 2.903 min, MS: ES−366.33.

Step e.

To a solution of 1-(tert-butoxycarbonyl)-4-(3-ethylphenyl)indoline-6-carboxylic acid (0.625 g, 1.70 mmol) in THF (7 ml) were added DIPEA (0.58 ml, 3.4 mmol) and HATU (0.970 g, 2.55 mmol) at 0° C. The reaction mixture was stirred at 0° C. for 30 min. Methylamine (2 M solution in THF; 0.94 ml, 1.88 mmol) was added to the reaction mixture at 0° C. The reaction mixture was stirred at rt for 2 h. The resulting mixture was poured into saturated NaHCO$_3$ solution (100 ml) and extracted with EtOAc (2×80 ml). The combined organic phase was washed with brine solution (70 ml), dried over Na$_2$SO$_4$, filtered and concentrated under reduced pressure. The resulting residue was purified by column chromatography (5.2% MeOH in DCM) yielding tert-butyl 4-(3-ethylphenyl)-6-(methylcarbamoyl)-indoline-1-carboxylate (0.600 g, 1.58 mmol). LCMS: Method C, 2.792 min, MS: ES+381.51

Step f.

To a stirred solution of tert-butyl 4-(3-ethylphenyl)-6-(methylcarbamoyl)-indoline-1-carboxylate (0.600 g, 1.58 mmol) in DCM (5 ml) was added TFA (5 ml) at rt. The reaction mixture was stirred at rt for 1 h. The resulting reaction mixture was concentrated under reduced pressure. The obtained residue was co-distilled with diethyl ether (2×5 ml). The obtained residue was triturated using diethyl ether (5 ml) and the resultant solid material was dried under high vacuum yielding 4-(3-ethylphenyl)-N-methylindoline-6-carboxamide TFA salt (0.500 g, 1.13). This material was used directly for next step without further purification. LCMS: Method C, 2.054 min, MS: ES+281.23.

Steps g, h, i.

The title compound was synthesised from the intermediate above using a procedure similar to that described for Example 10, steps d, e, f. LCMS: Method B, 4.418 min, MS: ES+403.06; $^1$H NMR (400 MHz, DMSO-d6) δ ppm 8.59 (s, 1H), 8.45-8.46 (m, 1H), 7.54 (s, 1H), 7.32-7.42 (m, 3H), 7.25-7.27 (m, 1H), 4.20 (t, J=8.4 Hz, 2H), 3.58-3.67 (m, 2H), 3.44-3.52 (m, 3H), 3.24 (t, J=8.4 Hz, 2H), 2.77 (d, J=4.8 Hz, 3H), 2.65-2.71 (m, 2H), 2.19-2.24 (m, 1H), 2.05-2.10 (m, 1H), 1.23 (t, J=7.6 Hz, 3H).

Example 69 (R)-1-(1-Cyanopyrrolidine-3-carbonyl)-N-methyl-4-phenylindoline-6-carboxamide

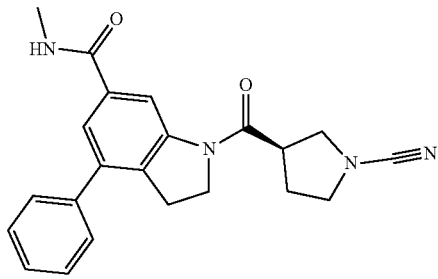 [SMILES: CNC(=O)c1cc(-c2ccccc2)c2c(c1)N(C(=O)[C@@H]1CCN(C#N)C1)CC2]

The title compound was synthesised using a procedure similar to that described for Example 68. LCMS: Method A, 3.785 min, MS: ES+375.05; $^1$H NMR (400 MHz, DMSO-d6) δ ppm 8.63 (s, 1H), 7.56 (s, 1H), 7.46-7.49 (m, 4H), 7.39-7.42 (m, 1H), 4.26 (t, J=8.4 Hz, 2H), 3.68-3.77 (m, 2H), 3.53-3.64 (m, 4H), 3.30 (t, J=8.4 Hz, 2H), 2.93 (s, 3H), 2.31-2.35 (m, 1H), 2.20-2.29 (m, 1H).

Biological Activity of Compounds of the Invention

Abbreviations:

TAMRA carboxytetramethylrhodamine
PCR polymerase chain reaction
PBS phosphate buffered saline
EDTA ethylenediaminetetraacetic acid
Tris 2-amino-2-(hydroxymethyl)-1,3-propanediol
NP-40 Nonidet P-40, octylphenoxypolyethoxyethanol
BSA bovine serum albumin
PNS peripheral nervous system
BH3 Bcl-2 homology domain 3
PTEN phosphatase and tensin homologue In Vitro USP30 Inhibition Assay USP30 Biochemical Kinetic Assay.

Reactions were performed in duplicate in black 384 well plates (small volume, Greiner 784076) in a final reaction volume of 21 μl. USP30 CD (57-517, #64-0057-050 Ubiquigent) was diluted in reaction buffer (40 mM Tris, pH 7.5, 0.005% Tween 20, 0.5 mg/ml BSA, 5 mM beta-mercaptoethanol) to the equivalent of 0, 0.005, 0.01, 0.05, 0.1 and 0.5 μl/well. Buffer was optimised for optimal temperature, pH, reducing agent, salts, time of incubation, and detergent. Reactions were initiated by the addition of 50 nM of TAMRA labelled peptide linked to ubiquitin via an iso-peptide bond as fluorescence polarisation substrate. Reactions were incubated at room temperature and read every 2 min for 120 min. Readings were performed on a Pherastar Plus (BMG Labtech). λ Excitation 540 nm; λ Emission 590 nm.

USP30 Biochemical IC50 Assay

Dilution plates were prepared at 21 times the final concentration (2100 M for a final concentration of 100 μM) in 50% DMSO in a 96-well polypropylene V-bottom plate (Greiner #651201). A typical 8-point dilution series to be 100, 30, 10, 3, 1, 0.3, 0.1, 0.03 M final.

Reactions were performed in duplicate in black 384 well plates (small volume, Greiner 784076) in a final reaction volume of 21 μl. Either 1 μl of 50% DMSO or diluted compound was added to the plate. USP30 was diluted in reaction buffer (40 mM Tris, pH 7.5, 0.005% Tween 20, 0.5 mg/ml BSA, 5 mM beta-mercaptoethanol) to the equivalent of 0.05 l/well and 10 μl of diluted USP30 was added to the compound. Enzyme and compound were incubated for 30 min at room temp. Reactions were initiated by the addition of 50 nM of TAMRA labelled peptide linked to ubiquitin via an iso-peptide bond as fluorescence polarisation substrate. Reactions were read immediately after addition of substrate and following a 2 hr incubation at room temperature. Readings were performed on a Pherastar Plus (BMG Labtech). λ Excitation 540 nm; λ Emission 590 nm.

Activity of Exemplary Compounds in USP30 biochemical IC50 assay

Ranges:

A<0.1 μM;
0.1<B<1 μM;
1<C<10 μM.

| Example No. | IC50 range |
|---|---|
| 1 | C |
| 2 | C |
| 3 | B |
| 4 | C |
| 5 | C |
| 6 | D |
| 7 | C |
| 8 | B |
| 9 | B |
| 10 | B |
| 11 | C |
| 12 | B |
| 13 | B |
| 14 | B |
| 15 | B |
| 16 | B |
| 17 | C |
| 18 | B |
| 19 | B |
| 20 | C |
| 21 | C |
| 22 | B |
| 23 | B |
| 24 | B |
| 25 | B |
| 26 | C |
| 27 | B |
| 28 | C |
| 29 | C |
| 30 | C |
| 31 | C |
| 32 | C |
| 33 | B |
| 34 | B |
| 35 | C |
| 36 | C |
| 37 | B |
| 38 | C |
| 39 | B |
| 40 | A |
| 41 | B |
| 42 | B |
| 43 | B |
| 44 | C |
| 45 | C |
| 46 | C |
| 47 | B |
| 48 | C |
| 49 | B |
| 50 | B |
| 51 | C |
| 52 | B |
| 53 | B |
| 54 | B |
| 55 | B |
| 56 | A |
| 57 | B |
| 58 | C |
| 59 | C |
| 60 | B |
| 61 | C |
| 62 | C |
| 63 | C |
| 64 | C |
| 65 | B |
| 66 | B |
| 67 | C |
| 68 | B |
| 69 | C |

The invention claimed is:

1. A compound of formula I:

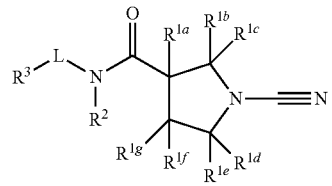

a tautomer thereof, or a pharmaceutically acceptable salt of said compound or tautomer, wherein:

$R^{1b}$, $R^{1c}$, $R^{1d}$ and $R^{1e}$ are each independently selected from hydrogen and optionally, substituted $C_1$-$C_6$ alkyl, or $R^{1b}$ is linked to $R^{1c}$ or $R^{1a}$ to form an optionally substituted $C_3$-$C_6$ cycloalkyl ring, or $R^{1e}$ is linked to $R^{1d}$ or $R^{1f}$ to form an optionally substituted $C_3$-$C_6$ cycloalkyl ring;

$R^{1a}$, $R^{1f}$ and $R^{1g}$ are each independently selected from hydrogen, fluorine, cyano, hydroxyl, amino, optionally substituted $C_1$-$C_6$ alkyl, and optionally substituted $C_1$-$C_6$ alkoxy, or $R^{1a}$ is linked to $R^{1b}$ to form an optionally substituted $C_3$-$C_6$ cycloalkyl ring, or $R^{1a}$ or $R^{1g}$ is linked to $R^2$ to form an optionally further substituted 5 or 6-membered heterocyclyl ring, or $R^{1f}$ is linked to $R^{1e}$ or $R^{1g}$ to form an optionally substituted $C_3$-$C_6$ cycloalkyl ring;

$R^2$ is optionally substituted $C_1$-$C_3$ alkyl, or together with $R^3$ forms an optionally substituted 5 to 10-membered, monocyclic or bicyclic, heterocyclyl or heteroaryl ring, or $R^2$ together with $R^{1g}$ or $R^{1a}$ forms an optionally further substituted 5 or 6-membered heterocyclyl ring;

$R^3$ is an optionally substituted 5 to 10-membered, monocyclic or bicyclic, heteroaryl or aryl ring, or $R^3$ together with $R^2$ forms an optionally substituted 5 to 10-membered, monocyclic or bicyclic, heterocyclyl or heteroaryl ring;

wherein the heterocyclyl ring formed by $R^2$ together with $R^{1g}$ or $R^{1a}$, is optionally substituted by one to four groups, each independently selected from fluorine, chlorine, oxo, cyano, $C_1$-$C_3$ alkyl, and $C_1$-$C_3$ alkoxy;

L represents a covalent bond or an optionally substituted $C_1$-$C_3$ alkylene, or forms part of the heterocyclyl or heteroaryl ring formed by $R^2$ and $R^3$;

$R^3$ or the ring formed by $R^2$ and $R^3$ is substituted with one to four -$Q^1$-$(R^4)_n$ moieties, wherein each occurrence of -$Q^1$($R^4)_n$ is the same or different, wherein;

n is 0 or 1;

$Q^1$ is selected from halogen, cyano, oxo, nitro, —$OR^5$, —$SR^5$, —$NR^5R^6$, —$CONR^5R^6$, $NR^5COR^6$, —$NR^5CONR^6R^7$, —$COR^5$, —$C(O)OR^5$, —$SO_2R^5$, —$SO_2NR^5R^6$, —$NR^5SO_2R^6$, $NR^5SO_2NR^6R^7$, —$NR^5C(O)OR^6$, optionally substituted —$C_1$-$C_6$ alkyl, optionally substituted alkoxy, optionally substituted —$C_2$-$C_6$ alkenyl, a covalent bond, an oxygen atom, a sulphur atom, —SO—, —$SO_2$—, —CO—, —C(O)O—, —$CONR^5$—, —$NR^5$—, —$NR^5CO$—, —$NR^5CONR^6$—, —$SO_2NR^5$—, $NR^5SO_2$—, —$NR^5SO_2NR^6$—, —$NR^5C(O)O$—, —$NR^5C(O)OR^6$—, optionally substituted $C_1$-$C_6$ alkylene, optionally substituted —$C_1$-$C_6$ alkyleneoxy, and optionally substituted —$C_2$-$C_6$ alkenylene;

93

R⁴ is a 3 to 10-membered, monocyclic or bicyclic, heterocyclyl, heteroaryl, aryl or cycloalkyl ring, which is optionally substituted with 1 to 4 groups, each independently selected from halogen, cyano, oxo, nitro, —OR⁸, —SR⁸, —NR⁸R⁹, —CONR⁸R⁹, —NR⁸COR⁹, —NR⁸CONR⁹R¹⁰, —COR⁸, —C(O)OR⁸, —SO₂R⁸, —SO₂NR⁸R⁹, —NR⁸SO₂R⁹, NR⁸SO₂NR⁹R¹⁰, —NR⁸C(O)OR⁹, optionally substituted —C₁-C₆ alkyl, optionally substituted —C₁-C₆ alkoxy, optionally substituted —C₂-C₆ alkenyl, optionally substituted C₂-C₆ alkynyl, C₃-C₁₀ heterocyclyl, C₃-C₁₀ cycloalkyl, C₅-C₁₀ heteroaryl, C₅-C₁₀ aryl, -Q²-R⁸, -Q²-NR⁸CONR⁹R¹⁰, -Q²-NR⁸R⁹, -Q²-COR⁸, -Q²-NR⁸COR⁹, -Q²-NR⁸C(O)OR⁹, -Q²-SO₂R⁸, Q²-CONR⁸R⁹, -Q²-CO₂R⁸, -Q²-SO₂NR⁸R⁹, -Q²-NR⁸SO₂R⁹ and -Q²-NR⁸SO₂NR⁹R¹⁰;

wherein the optional substituents for the heterocyclyl, cycloalkyl, heteroaryl and aryl rings are selected from fluorine, chlorine, oxo, cyano, C₁-C₃ alkyl, and C₁-C₃ alkoxy;

Q² is selected from a covalent bond, an oxygen atom, a sulphur atom, —SO—, —SO₂—, —CO—, optionally substituted C₁-C₆ alkylene, optionally substituted C₁-C₆ alkyleneoxy, and optionally substituted C₂-C₆ alkenylene;

R⁸, R⁹ and R¹⁰ are each independently selected from hydrogen, optionally substituted C₁-C₆ alkyl, optionally substituted C₃-C₁₀ heterocyclyl, optionally substituted C₅-C₁₀ heteroaryl, optionally substituted C₅-C₁₀ aryl, and optionally substituted C₃-C₆ cycloalkyl;

wherein the optional substituents for the heterocyclyl, cycloalkyl, heteroaryl and aryl rings are selected from fluorine, chlorine, oxo, cyano, C₁-C₃ alkyl, and C₁-C₃ alkoxy;

R⁵, R⁶ and R⁷ are each independently selected from hydrogen, optionally substituted C₁-C₆ alkyl, and optionally substituted C₁-C₆ alkylene;

wherein the alkyl, alkoxy, alkenyl, alkynyl, alkylene, alkyleneoxy, and alkenylene groups of R¹ᵃ, R¹ᵇ, R¹ᶜ, R¹ᵈ, R¹ᵉ, R¹ᶠ, R¹ᵍ, R², R⁴, R⁵, R⁶, R⁷, R⁸, R⁹, R¹⁰, L, Q¹, and Q² are optionally substituted with one to four substituents, each independently selected from halogen, hydroxy and cyano; and wherein the cycloalkyl groups of R¹ᵃ, R¹ᵇ, R¹ᶜ, R¹ᵈ, R¹ᵉ, R¹ᶠ, and R¹ᵍ are optionally substituted with one or two substituents, each independently selected from halogen, deutero, cyano, oxo, nitro, amino, hydroxy, C₁-C₃ alkyl and C₁-C₃ alkoxy, wherein the alkyl and alkoxy may be substituted with one or more halogen.

2. The compound according to claim 1, wherein R¹ᵃ is hydrogen or fluorine.

3. The compound according to claim 1, wherein R¹ᵃ, R¹ᵇ, R¹ᶜ, R¹ᵈ, R¹ᵉ, R¹ᶠ and R¹ᵍ each represent hydrogen.

4. The compound according to claim 1, wherein R² is C₁-C₃ alkyl, which is optionally substituted with one or more fluorine.

5. The compound according to claim 1, wherein R² together with R¹ᵃ or R¹ᵍ forms an optionally further substituted 5 or ti-membered heterocyclyl ring.

6. The compound according to claim 1, wherein R³ or the ring formed by R² and R³ is substituted or substituted with one or two -Q¹-(R⁴)ₙ moieties, which are the same or different, and wherein n is 1 for at least one of the moieties.

7. The compound according to claim 1, wherein R³ is an optionally substituted, 5 to 10-membered, nitrogen-containing, monocyclic or bicyclic, heteroaryl ring, or optionally substituted phenyl.

94

8. The compound according to claim 7, wherein R³ is selected from optionally substituted, thiazolyl, pyridinyl, pyridazinyl, benzothiazolyl, isoxazolyl, and phenyl.

9. The compound according to claim 1, wherein R² and R³ together form an optionally substituted, 9 or 10-membered bicyclic, heterocyclyl or heteroaryl, ring.

10. The compound according to claim 9, wherein R² together with R³ form a ring selected from optionally substituted, indolinyl, dihydropyrrolopyridinyl, tetrahydroquinolinyl and dihydrobenzoxazinyl.

11. The compound according to claim 1, wherein when n is 0, Q¹ is selected from halogen, cyano, C₁-C₆ alkyl, and C₁-C₃ alkyl optionally substituted with one or more fluorine; and when n is 1, Q¹ is a covalent bond.

12. The compound according to claim 1, wherein R⁴ is selected from optionally substituted, phenyl, pyridinyl, pyrazolyl and indazolyl.

13. The compound according to claim 12, wherein R⁴ is optionally substituted with one to three substituents selected from halogen, cyano, C₁-C₆ alkyl, C₁-C₆ alkoxy, and NR⁸SO₂R⁹, wherein R⁸ and R⁹ are each independently selected from hydrogen, C₁-C₃ alkyl, and C₃-C₆ cycloalkyl; wherein the alkyl or alkoxy may be optionally substituted with one or more fluorine.

14. The compound according to claim 1, of formula (II):

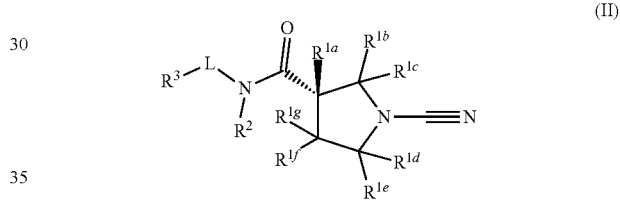

(II)

a tautomer thereof; or a pharmaceutically acceptable salt of said compound or tautomer.

15. A compound of formula I according to claim 1 selected from the group consisting of:
1-cyano-N-ethyl-N-(4-phenylthiazol-2-yl)pyrrolidine-3-carboxamide;
1-cyano-N-ethyl-N-(5-phenylthiazol-2-yl)pyrrolidine-3-carboxamide;
(S)-1-cyano-N-methyl-N-(5-phenylthiazol-2-yl)pyrrolidine-3-carboxamide;
(S)-1-cyano-N-methyl-N-(4-phenylpyridin-2-yl)pyrrolidine-3-carboxamide;
(S)-1-cyano-N-methyl-N-(6-phenylpyridin-2-yl)pyrrolidine-3-carboxamide;
1-cyano-N-isopropyl-N-(5-(pyridin-4-yl)thiazol-2-yl)pyrrolidine-3-carboxamide;
1-cyano-N-isopropyl-N-(4-phenylthiazol-2-yl)pyrrolidine-3-carboxamide;
1-cyano-3-fluoro-N-methyl-N-(5-phenylthiazol-2-yl)pyrrolidine-3-carboxamide;
N-(benzo[d]thiazol-2-yl)-1-cyano-3-fluoro-N-methylpyrrolidine-3-carboxamide;
(S)-3-(4-phenylindoline-1-carbonyl)pyrrolidine-1-carbonitrile;
(R)-3-(6-phenylindoline-1-carbonyl)pyrrolidine-1-carbonitrile;
(S)-3-(5-(3-chlorophenyl)indoline-1-carbonyl)pyrrolidine-1-carbonitrile;
(3S,4S)-3-(5-(2-chlorophenyl)indoline-1-carbonyl)-4-methylpyrrolidine-1-carbonitrile;

3-fluoro-3-(5-phenylindoline-1-carbonyl)pyrrolidine-1-carbonitrile;
3-fluoro-3-(6-phenylindoline-1-carbonyl)pyrrolidine-1-carbonitrile;
3-fluoro-3-(6-phenyl-2,3-dihydro-1H-pyrrolo[2,3-b]pyridine-1-carbonyl)pyrrolidine-1-carbonitrile;
(R)-3-(5-phenylindoline-1-carbonyl)pyrrolidine-1-carbonitrile;
(S)-3-(5-phenylindoline-1-carbonyl)pyrrolidine-1-carbonitrile;
(3S,4S)-3-methyl-4-(5-phenylindoline-1-carbonyl)pyrrolidine-1-carbonitrile;
(3R,4R)-3-methyl-4-(5-phenylindoline-1-carbonyl)pyrrolidine-1-carbonitrile;
(S)-3-(5-phenyl-2,3-dihydro-1H-pyrrolo[2,3-b]pyridine-1-carbonyl)pyrrolidine-1-carbonitrile;
3-fluoro-3-(5-phenyl-2,3-dihydro-1H-pyrrolo[2,3-b]pyridine-1-carbonyl)pyrrolidine-1-carbonitrile;
(S)-3-(6-phenyl-1,2,3,4-tetrahydroquinoline-1-carbonyl)pyrrolidine-1-carbonitrile;
(R)-3-(7-phenyl-3,4-dihydro-2H-benzo[b][1,4]oxazine-4-carbonyl)pyrrolidine-1-carbonitrile;
(R)-3-(6-phenyl-3,4-dihydro-2H-benzo[b][1,4]oxazine-4-carbonyl)pyrrolidine-1-carbonitrile;
(R)-3-(8-phenyl-3,4-dihydro-2H-benzo[b][1,4]oxazine-4-carbonyl)pyrrolidine-1-carbonitrile;
(S)-3-(4-phenyl-2,3-dihydro-1H-pyrrolo[2,3-b]pyridine-1-carbonyl)pyrrolidine-1-carbonitrile;
(S)-3-(4-(3-chlorophenyl)-2,3-dihydro-1H-pyrrolo[2,3-b]pyridine-1-carbonyl)pyrrolidine-1-carbonitrile;
(S)-1-(1-cyanopyrrolidine-3-carbonyl)-5-(1-methyl-1H-pyrazol-4-yl)indoline-6-carbonitrile;
(R)-3-(7-(1H-pyrazol-1-yl)-3,4-dihydro-2H-benzo[b][1,4]oxazine-4-carbonyl)pyrrolidine-1-carbonitrile;
(S)-1-cyano-N-methyl-N-(5-phenylpyridin-2-yl)pyrrolidine-3-carboxamide;
(R)-1-cyano-N-methyl-N-(5-phenylpyridazin-3-yl)pyrrolidine-3-carboxamide;
1-cyano-3-fluoro-N-methyl-N-(5-phenylisoxazol-3-yl)pyrrolidine-3-carboxamide;
(3S,4S)-1-cyano-4-(hydroxymethyl)-N-methyl-N-(5-phenylthiazol-2-yl)pyrrolidine-3-carboxamide;
3-(5-(1-benzyl-1H-pyrazol-5-yl)indoline-1-carbonyl)-3-fluoropyrrolidine-1-carbonitrile;
3-fluoro-3-(5-(1-methyl-1H-pyrazol-5-yl)indoline-1-carbonyl)pyrrolidine-1-carbonitrile;
3-fluoro-3-(5-(4-(4-methylpiperazin-1-yl)phenyl)indoline-1-carbonyl)pyrrolidine-1-carbonitrile;
3-fluoro-3-(5-(4-(4-methylpiperazine-1-carbonyl)phenyl)indoline-1-carbonyl)pyrrolidine-1-carbonitrile;
3-fluoro-3-(5-(1-methyl-1H-indazol-5-yl)indoline-1-carbonyl)pyrrolidine-1-carbonitrile;
3-fluoro-3-(5-(2-fluoro-5-methylphenyl)indoline-1-carbonyl)pyrrolidine-1-carbonitrile;
3-fluoro-3-(5-(5-methyl-1H-indazol-4-yl)indoline-1-carbonyl)pyrrolidine-1-carbonitrile;
N-(3-(1-(1-cyano-3-fluoropyrrolidine-3-carbonyl)indolin-5-yl)phenyl)cyclopropanesulfonamide;
3-fluoro-3-(5-(6-methoxypyridin-3-yl)indoline-1-carbonyl)pyrrolidine-1-carbonitrile;
(R)-1-cyano-N-(5-(4-cyanophenyl)pyridin-2-yl)-N-ethylpyrrolidine-3-carboxamide;
N-(benzo[d]thiazol-2-ylmethyl)-1-cyano-N-methylpyrrolidine-3-carboxamide;
1-cyano-N-methyl-N-((3-phenylisoxazol-5-yl)methyl)pyrrolidine-3-carboxamide;
1-cyano-N-methyl-N-((2-phenylthiazol-4-y)methyl)pyrrolidine-3-carboxamide;
(3aR,6aS)-4-oxo-5-(5-phenylthiazol-2-yl)hexahydropyrrolo[3,4-c]pyrrole-2(1H)-carbonitrile; and
7-([1,1'-biphenyl]-3-yl)-6-oxo-2,7-diazaspiro[4.4]nonane-2-carbonitrile;
a tautomer thereof, or a pharmaceutically acceptable salt of said compound or tautomer.

16. A compound of formula I according to claim 1, selected from the group consisting of:
(R)-3-(4-(3-ethylphenyl)indoline-1-carbonyl)pyrrolidine-1-carbonitrile;
(R)-1-(1-cyanopyrrolidine-3-carbonyl)-N-methyl-4-phenylindoline-6-carboxamide;
(R)-1-(1-cyanopyrrolidine-3-carbonyl)-4-(3-ethylphenyl)-N-methylindoline-6-carboxamide;
(R)-3-(5-(1H-indazol-4-yl)-2,3-dihydro-1H-pyrrolo[2,3-b]pyridine-1-carbonyl)pyrrolidine-1-carbonitrile;
(S)-3-(5-(1H-indazol-4-yl)-2,3-dihydro-1H-pyrrolo[2,3-b]pyridine-1-carbonyl)pyrrolidine-1-carbonitrile;
3-(5-phenyl-2,3-dihydro-1H-pyrrolo[3,2-b]pyridine-1-carbonyl)pyrrolidine-1-carbonitrile;
(trans)-3-methyl-4-(5-phenyl-2,3-dihydro-1H-pyrrolo[2,3-b]pyridine-1-carbonyl)pyrrolidine-1-carbonitrile;
3-fluoro-3-(5-(1-isobutyl-1H-pyrazol-5-yl)indoline-1-carbonyl)pyrrolidine-1-carbonitrile;
3-(5-(1-benzyl-1H-pyrazol-4-yl)indoline-1-carbonyl)-3-fluoropyrrolidine-1-carbonitrile;
3-fluoro-3-(5-(1-(pyridin-2-ylmethyl)-1H-pyrazol-5-yl)indoline-1-carbonyl)pyrrolidine-1-carbonitrile;
N-benzyl-1-(1-cyano-3-fluoropyrrolidine-3-carbonyl)indoline-5-carboxamide;
3-(5-(1-(2-chlorobenzyl)-1H-pyrazol-5-yl)indoline-1-carbonyl)-3-fluoropyrrolidine-1-carbonitrile;
3-(5-(1-(3-chlorobenzyl)-1H-pyrazol-5-yl)indoline-1-carbonyl)-3-fluoropyrrolidine-1-carbonitrile;
3-(5-(1-(4-chlorobenzyl)-1H-pyrazol-5-yl)indoline-1-carbonyl)-3-fluoropyrrolidine-1-carbonitrile;
3-fluoro-3-(5-(1-(pyridin-3-ylmethyl)-1H-pyrazol-5-yl)indoline-1-carbonyl)pyrrolidine-1-carbonitrile;
3-fluoro-3-(5-(pyridin-3-yl)indoline-1H-carbonyl)pyrrolidine-1-carbonitrile;
(R)-3-fluoro-3-(5-phenylindoline-1-carbonyl)pyrrolidine-1-carbonitrile;
(S)-3-fluoro-3-(5-phenylindoline-1-carbonyl)pyrrolidine-1-carbonitrile;
(S)-3-(5-(3-chlorophenyl)-2,3-dihydro-1H-pyrrolo[2,3-b]pyridine-1-carbonyl)-3-fluoropyrrolidine-1-carbonitrile; and
(R)-3-(5-(3-chlorophenyl)-2,3-dihydro-1H-pyrrolo[2,3-b]pyridine-1-carbonyl)-3-fluoropyrrolidine-1-carbonitrile;
a tautomer thereof, or a pharmaceutically acceptable salt of said compound or tautomer.

17. A pharmaceutical composition comprising a compound of formula I as defined in claim 1, a tautomer thereof, or a pharmaceutically acceptable salt of said compound or tautomer, together with one or more pharmaceutically acceptable excipients.

* * * * *

UNITED STATES PATENT AND TRADEMARK OFFICE
CERTIFICATE OF CORRECTION

PATENT NO. : 10,640,498 B2
APPLICATION NO. : 16/070936
DATED : May 5, 2020
INVENTOR(S) : Karl Richard Gibson et al.

Page 1 of 1

It is certified that error appears in the above-identified patent and that said Letters Patent is hereby corrected as shown below:

In the Claims

At Column 92, Line 59, --C1-C6-- should be inserted before "alkoxy."

At Column 93, Line 59, "ti-membered" should be printed as "6-membered."

At Column 93, Line 61, "R3 is substituted" should be printed as "R3 is unsubstituted."

At Column 96, Line 3, "2-phenylthiazol-4-y" should be printed as "2-phenylthiazol-4-yl."

At Column 96, Line 45, "indoline-1H-carbonyl" should be printed as "indoline-1-carbonyl."

Signed and Sealed this
Eighth Day of February, 2022

Drew Hirshfeld
*Performing the Functions and Duties of the
Under Secretary of Commerce for Intellectual Property and
Director of the United States Patent and Trademark Office*